US012744112B2

(12) United States Patent
Kanegawa et al.

(10) Patent No.: US 12,744,112 B2
(45) Date of Patent: Sep. 22, 2026

(54) INFORMATION PROCESSING APPARATUS, INFORMATION PROCESSING METHOD, AND RECORDING MEDIUM

(71) Applicant: SUNTORY HOLDINGS LIMITED, Osaka City (JP)

(72) Inventors: Norimasa Kanegawa, Kyoto (JP); Yuka Kutsumi, Kyoto (JP); Mitsuhiro Zeida, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 273 days.

(21) Appl. No.: 18/275,766

(22) PCT Filed: Feb. 1, 2022

(86) PCT No.: PCT/JP2022/003809
§ 371 (c)(1),
(2) Date: Aug. 3, 2023

(87) PCT Pub. No.: WO2022/168827
PCT Pub. Date: Aug. 11, 2022

(65) Prior Publication Data

US 2024/0296925 A1 Sep. 5, 2024

(30) Foreign Application Priority Data

Feb. 5, 2021 (JP) ................................ 2021-017040
Feb. 5, 2021 (JP) ................................ 2021-017041

(51) Int. Cl.
*G16H 20/00* (2018.01)
*A61B 5/00* (2006.01)
(Continued)

(52) U.S. Cl.
CPC ............ *G16H 20/00* (2018.01); *A61B 5/1118* (2013.01); *A61B 5/42* (2013.01); *A61B 5/7267* (2013.01); *G16H 50/30* (2018.01)

(58) Field of Classification Search
CPC ........ G16H 20/00; G16H 50/30; G16H 20/60; G16H 20/70; G16H 10/60; A61B 5/1118;
(Continued)

(56) References Cited

U.S. PATENT DOCUMENTS

2003/0177177 A1 9/2003 Oka et al.
2015/0148621 A1* 5/2015 Sier ........................ A61B 5/372 600/595

(Continued)

FOREIGN PATENT DOCUMENTS

JP 2003-263504 A 9/2003
JP 2009-233027 A 10/2009

(Continued)

OTHER PUBLICATIONS

Partial supplementary European Search Report dated Nov. 12, 2024, issued in counterpart Application No. 22749699.9. (13 pages).

(Continued)

*Primary Examiner* — Eliza A Lam
(74) *Attorney, Agent, or Firm* — WHDA, LLP

(57) ABSTRACT

An information processing apparatus 100 includes: a learning information acquiring unit 148 that acquires learning information configured using training data having activity information regarding an activity state of a user and a score regarding a health state of the user; a first activity information acquiring unit 144 that acquires first activity information; a score acquiring unit 149 that acquires a score; a second activity information acquiring unit 153 that acquires second activity information in which a score acquired by applying the learning information thereto is different from (Continued)

the score acquired by the score acquiring unit 149; and a recommendation information acquiring unit 157 that acquires recommendation information according to a result of a comparison between the first activity information and the second activity information. Accordingly, it is possible to output information regarding user's health.

14 Claims, 36 Drawing Sheets

(51) Int. Cl.
*A61B 5/11* (2006.01)
*G16H 50/30* (2018.01)

(58) Field of Classification Search
CPC ......... A61B 5/42; A61B 5/7267; A61B 7/003; A61B 7/04; A61B 5/7264; A61B 5/7275
See application file for complete search history.

(56) References Cited

U.S. PATENT DOCUMENTS

2019/0221317 A1 7/2019 Kempanna et al.
2019/0341151 A1 11/2019 Hamada et al.
2020/0135320 A1* 4/2020 Vleugels ................ G16H 20/10
2020/0303074 A1* 9/2020 Mueller-Wolf ...... A61B 5/7275
2021/0045694 A1* 2/2021 Hadley .................. G16H 80/00

FOREIGN PATENT DOCUMENTS

JP 2012-85906 A 5/2012
JP 2012256186 A * 12/2012
JP 2017-41035 A 2/2017
JP 2018-5536 A 1/2018
JP 2019-197269 A 11/2019
KR 20190000194 A 1/2019
WO 2020/041363 A1 2/2020

OTHER PUBLICATIONS

Du, X. et al.; Bowel Sounds Identification and Migrating Motor Complex Detection with Low-Cost Piezoelectric Acoustic Sensing Device; Sensors, 2018, vol. 18, No. 4240, p. 1-12. (12 pages); cited in Extended European Search Report issued on Feb. 11, 2025.

International Search Report dated May 10, 2022, issued in counterpart International Application No. PCT/JP2022/003809, with English Translation. (7 pages).

* cited by examiner

| Parameter identifier | Task identifier | Task name | Task description | Product identifier |
|---|---|---|---|---|
| ⋮ | ⋮ | ⋮ | ⋮ | ⋮ |
| Peristalsis movements | C8876 | Drink a bottle of vegetable juice a day... | Dietary fiber... | 001234 |
| ⋮ | ⋮ | ⋮ | ⋮ | ⋮ |
| Walking | M7890 | Walk at least 6000 steps every day... | Walking... | (NULL) |
| ⋮ | ⋮ | ⋮ | ⋮ | ⋮ |
| Blood pressure | C0123 | Control the amount of salt per day to ... | Excessive salt intake... | 678902 |
| ⋮ | ⋮ | ⋮ | ⋮ | ⋮ |

Fig.15

| Issue identifier | Task identifier | Task name | Task description | Product identifier |
|---|---|---|---|---|
| ⋮ | ⋮ | ⋮ | ⋮ | ⋮ |
| Peristalsis movements | C8876 | OO tea… | OO tea is… | 001234 |
| Peristalsis movements | D1212 | Do abdominal massage | The abdomen… | (NULL) |
| Slightly having diarrhea | M7890 | Walk at least 6000 steps every day… | Walking… | (NULL) |
| Slightly having constipation | C8550 | Dietary fiber… | Cellulose (… | (NULL) |
| Slightly having constipation | C0123 | ~~ drink… | ~~ drink is… | 678902 |
| ⋮ | ⋮ | ⋮ | ⋮ | ⋮ |

Fig.24

| Selection condition | Task identifier | Task name | Task description | Product identifier |
|---|---|---|---|---|
| ⋮ | ⋮ | ⋮ | ⋮ | ⋮ |
| Gut state score < X1 | C8876 | OO tea... | OO tea is... | 001234 |
| Gut movement score < X2 | D1212 | Do abdominal massage | The abdomen... | (NULL) |
| Gut score < X5 | M7890 | Walk at least 6000 steps every day... | Walking... | (NULL) |
| Excretion score < X3 and Gut score < X4 | C8550 | Dietary fiber... | Cellulose (... | (NULL) |
| Excretion score < X2 | C0123 | ~~ drink... | ~~ drink is... | 678902 |
| ⋮ | ⋮ | ⋮ | ⋮ | ⋮ |

Fig.30

INFORMATION PROCESSING APPARATUS, INFORMATION PROCESSING METHOD, AND RECORDING MEDIUM

TECHNICAL FIELD

The present invention relates to an information processing apparatus, an information processing method, and a recording medium for outputting information regarding user's health.

BACKGROUND ART

In recent years, users have become increasingly aware of their own health. Under these circumstances, various devices and services have been provided to support information on health and lifestyle habits. For example, Patent Document 1 below describes the configuration of a health management support system configured to acquire and record health management information on a user and output messages pertaining to health management to the user based on the content of the information.

CITATION LIST

Patent Document

Patent Document 1: JP 2017-041035A

SUMMARY OF INVENTION

Technical Problem

It is an object of the present invention to provide an information processing apparatus, an information processing method, and a recording medium capable of outputting information regarding user's health.

Solution to Problem

An aspect of the present invention is directed to an information processing apparatus including: a learning information acquiring unit that acquires learning information configured using two or more pieces of training data having activity information containing values of two or more parameters regarding an activity state of a user and a score regarding a health state of the user; a first activity information acquiring unit that acquires first activity information containing respective values of the two or more parameters, which are values according to the activity state of the user; a score acquiring unit that acquires a score regarding the health state of the user; a second activity information acquiring unit that acquires, using the learning information, second activity information in which a value of at least one of the two or more parameters is different from that in the first activity information, and in which a score acquired by applying the learning information to the second activity information is different from the score acquired by the score acquiring unit: a recommendation information acquiring unit that acquires recommendation information regarding at least one of the two or more parameters regarding the activity state of the user, according to a result of a comparison between the first activity information and the second activity information; and an output unit that outputs the recommendation information acquired by the recommendation information acquiring unit.

Another aspect of the present invention is directed to an information processing apparatus including: a sound information acquiring unit that acquires sound information regarding living body sounds, which are sounds emanating from a living body, of a user; a task acquiring unit that acquires one or more tasks corresponding to the user, using input information containing the sound information acquired by the sound information acquiring unit and learning information prepared in advance; and a task output unit that outputs information on the tasks acquired by the task acquiring unit.

Advantageous Effects of Invention

According to the information processing apparatus and the like of the present invention, it is possible to output information regarding user's health.

BRIEF DESCRIPTION OF DRAWINGS

FIG. 15 is a diagram showing an example of association information in a specific example of the embodiment.

FIG. 24 is a diagram showing an example of task association information for use in the information processing apparatus in the embodiment.

FIG. 30 is a diagram showing an example of task association information for use in the information processing apparatus in the embodiment.

DESCRIPTION OF EMBODIMENTS

Figure 1:
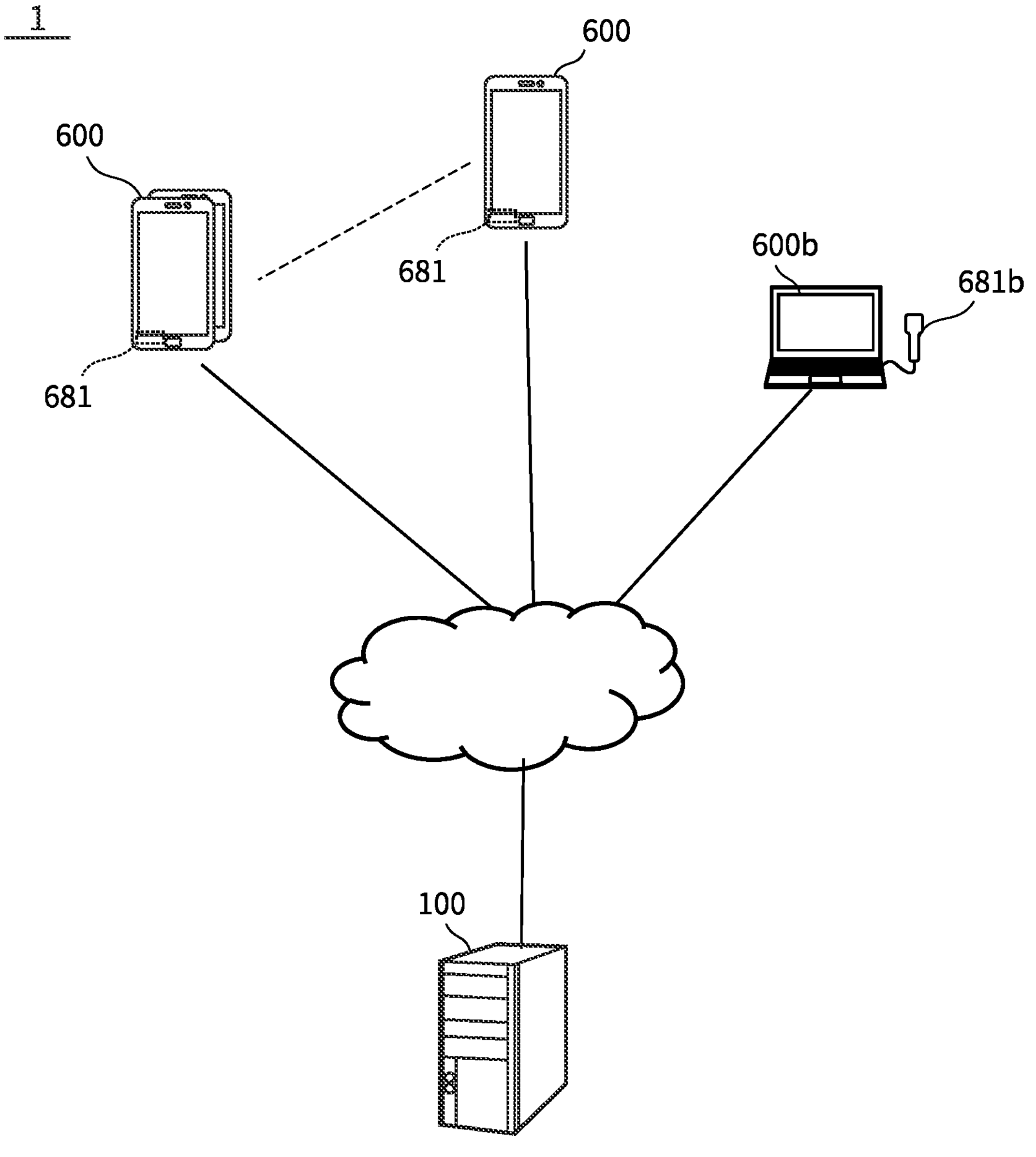
FIG. 1 is a diagram showing the outline of an information processing system according to Embodiment 1 of the present invention.

Below, an embodiment of the information processing apparatus and the like will be described with reference to the drawings. The constituent elements denoted by the same reference numerals in the embodiments perform similar operations, and thus a description thereof may not be repeated.

The terms used below are generally defined as follows. The meanings of these terms do not always have to be interpreted as indicated herein, and have to be interpreted in light of individual explanations below, if any, for example.

An identifier for a matter is a letter, a symbol, or the like for uniquely identifying the matter. The identifier is an ID, for example, but may be any type of information with which the corresponding matter can be identified. That is to say, the identifier may be the name of the matter itself that it indicates, or symbols that are combined so as to uniquely correspond to the matter.

The acquiring may include acquiring a matter that is input by a user or the like, or acquiring information stored in the apparatus or another apparatus (the information may be information stored in advance or information generated through information processing in the apparatus).

The acquiring information stored in another apparatus may include acquiring information stored in the other apparatus via an API or the like, or acquiring the content of a document file provided by the other apparatus (the content includes the webpage content, etc) through scraping or the like. The acquiring may include acquiring information in a different format based on the original information, such as acquiring information through optical character reading of an image file.

Furthermore, a so-called machine learning method may be used to acquire information. A machine learning method may be used as follows, for example. That is to say, a classifier in which a particular type of information for input is taken as input and a type of information that is to be acquired is taken as output is configured using a machine learning method. For example, two or more pairs of information (which may be referred to as "training data") each including information for input and information that is to be output are prepared in advance, the two or more pairs of information are given to a module for configuring a machine learning classifier to configure a classifier, and the configured classifier is accumulated in a storage unit. The classifier may also be said to be a learning model. There is no limitation on the machine learning method, and examples thereof include deep learning, random forests, and SVR. For example, functions in various machine learning frameworks and various existing libraries, such as fastText, tinySVM, random forest, and TnsorFlow, can be used for the machine learning.

Furthermore, the classifier is not limited to those obtained through machine learning. The classifier may be a table indicating the correspondence between an input vector based on information for input or the like and information that is to be output, for example. In this case, information that is to be output corresponding to a feature vector based on information for input may be acquired from the table, or a vector that is close to a feature vector based on the information for input may be generated using two or more input vectors in the table and parameters for weighting each input vector, and information that is to be output corresponding to the input vectors and parameters used for generation may be used to acquire final information that is to be output. The classifier may be a function or the like that represents the relationship between an input vector based on the information for input or the like and information for generating information that is to be output, for example. In this case, for example, information corresponding to a feature vector based on information for input may be obtained using a function, and the obtained information may be used to acquire information that is to be output.

The outputting information is a concept that encompasses display on a display screen, projection using a projector, printing by a printer, output of a sound, transmission to an external apparatus, accumulation in a recording medium, and delivery of a processing result to another processing apparatus or another program. Specifically, for example, this concept encompasses enabling information to be displayed on a webpage, transmission as an email or the like, and outputting information for printing.

The accepting information is a concept that encompasses accepting information input from an input device such as a keyboard, a mouse, or a touch panel, receiving information transmitted from another apparatus or the like via a wired or wireless communication line, and accepting information read from a recording medium such as an optical disk, a magnetic disk, or a semiconductor memory.

The updating various types of information stored in the information processing apparatus or the like is a concept that encompasses changing the stored information, adding new information to the stored information, and deleting the whole or part of the stored information.

Embodiment 1

In Embodiment 1, an information processing apparatus is configured to output information that is regarding an activity state of a user and that will change a score regarding a health state of the user. In particular, the information processing apparatus is configured to be capable of outputting information that is regarding an activity state of a user and that will realize a higher score regarding a health state of the user (corresponding to a higher degree of the user's health). The score may be acquired from health state information regarding the health state of the user. Hereinafter, the configuration of the information processing apparatus configured in this way will be described.

The terms used in Embodiment 1 are generally defined as follows. The meanings of these terms do not always have to be interpreted as indicated herein, and have to be interpreted in light of individual explanations in Embodiment 1, if any, for example.

The activity information is information containing a value of a parameter regarding an activity state of a user. The activity state of a user refers to that including various elements regarding the user's behavior, state, and the like, that is, the user's state that may correspond to the user's daily life. The activity state may be referred to as a life state. The activity state may include various matters such as a matter regarding excretion by a user, a matter regarding food consumed by the user, a matter regarding drink consumed by the user, and a matter regarding an activity status of the user, for example. The matters that correspond to the activity state are not limited to the above-listed matters, and may not, include one or more of these matters. For example, it is possible to use various parameters regarding excretion by the user, such as those indicating the state of excrement (amount, odor, and form (shape, color, etc.)), the time and the interval of excretion, or the like. For example, it is possible to use various parameters regarding food consumed by the user, such as those indicating the time and number of times food was consumed, the content of a meal, the types of food items contained, the types of nutrients contained, the amount, the amount of seasonings, the energy consumed, the method of consumption (e.g., chewing the food well, time spent on the meal, etc), or the like. For example, it is possible to use various parameters regarding drink consumed by the user, such as those indicating the time and number of times drink was consumed, the type of drink, whether it was alcoholic or not, the amount, the energy consumed, the method of consumption (e.g., hot or cold, etc), or the like. For example, as parameters regarding the activity status of the user, it is possible to use parameters other than those regarding eating and drinking or regarding excretion, such as matters related to a status regarding user's lifestyle habits (which refers to behaviors and actions that the user repeatedly performs in daily life), a status of one-time activities, or the like. Specifically, it is possible to use various parameters such as matters regarding sleep duration, sleep quality, exercise (the number of steps, the amount of calories burned, habitual exercise, intensity of exercise, frequency of exercise, time of specific exercise, whether or not the user meditated and its duration, etc.), or the like. In the activity information, information containing a value of a parameter regarding excretion by a user may be specifically referred to as excretion-related information, information containing a value of a parameter regarding food consumed by a user or a value of a parameter regarding drink consumed by a user may be specifically referred to as eating-and-drinking information, and information containing a value of a parameter regarding an activity status of a user may be specifically referred to as activity status information. In other words, it can be said that the activity information may contain each of excretion-elated information, eating-and-drinking information, and activity status information, for example. However, there is no limitation to this, and the activity information may contain information regarding other elements or information regarding only some of these elements. The information on each element of the activity information (excretion-related information, eating-and-drinking information, activity status information, etc.) may contain detailed information on the element. The values that may be contained in the activity information may be indicated as an absolute value for each parameter, a relative value with respect to a predetermined threshold value set for each parameter, or a value indicating whether the value is more or less than a predetermined threshold value, for example.

A task prepared in advance with respect to an activity state of a user may be used as a parameter regarding the activity state of the user. The task can be defined as an action or behavior that the user has to work on, or a state that the user has to have achieved as a result of working on the action or behavior. Such tasks may be categorized into those regarding food, those regarding an activity status, and the like, for example. The tasks may contain elements regarding a predetermined amount (such as, but not limited to, time, number of times, frequency, and load level) that the user has to work on. When a task is used as a parameter regarding an activity state of a user in this manner, the value of the parameter may include whether or not the task is set as a matter to be performed, whether or not the task has been performed, the progress status and degree of accomplishment regarding the execution of the task, or the like. A value of one task can be treated as being related to a value of another parameter to which the task is related, and vice versa. For example, the fact that a user has executed the task of jogging a given distance may be treated as activity information indicating the amount of calories burned by the user in exercising, or the fact that a user has executed the task of consuming milk may be treated as activity information indicating the amount of calories or nutrients consumed by the user.

The health state information is information regarding a health state of a user, and is information containing values of various parameters regarding user's health, for example. The health state of the user may be matters regarding the user's type and characteristics, for example, and specific examples thereof include matters such as the user's height, weight, age, sex, body fat percentage, muscle mass, pulse rate, respiratory rate, blood pressure, and the like, and whether the user is suffering from a given disease. The health state information may be information input by a user or the like in advance, information acquired by a wearable terminal or the like worn by the user or a portable terminal or the like held by the user, or information acquired from an external database or the like in which user information is recorded, for example.

The score regarding a health state of the user is a value that expresses the degree of the user's health in a scoring format, for example. For example, a higher score may indicate that the user is healthier. Alternatively, a lower score may indicate that the user is healthier. The score may be a value expressed in the form of a rank, or a statement of health state or the like may be used as the score.

The excretion-related information is information regarding the user's excretion status. As described above, the excretion-related information may include values of parameters from various viewpoints such as the time of excretion, amount, odor, and form (shape, color, etc.) of excrement. More specifically, for example, in this embodiment, the excretion-related information includes a value indicated by known Bristol Stool Form Scale (alternatively referred to as the "Bristol scale" hereinafter). The Bristol scale indicates the physiological transit time through the gastrointestinal tract and can be said to indirectly express the state of the guts. Labels corresponding to the values expressed by the Bristol scale (e.g., "banana", "sausage" "mushy", etc.) may be used as the excretion-related information. The excretion-related information may be information resulting from the evaluation of excretion by an evaluator such as a user (information involving the subjectivity of the evaluator) or information resulting from measurement or evaluation by an evaluation device or the like.

The eating-and-drinking information is information regarding the user's eating-and-drinking status. As described above, the eating-and-drinking information may include information from various viewpoints such as the amount of water consumed, the amount of alcohol consumed, and the content of a meal. The eating-and-drinking information may be conceptually divided into food information regarding food and eating habits and drink information regarding drink consumption. More specifically, for example, in this embodiment, the eating-and-drinking information includes, but is not limited to, at least one of information regarding the amount of water consumed, information regarding whether or not alcohol was consumed or the amount of alcohol consumed, information regarding whether or not a meal was taken or the content of a meal, and information regarding whether or not a particular group of food was consumed or the amount thereof consumed. The particular group of food refers to food that belongs to a particular group among the groups classified as meat, dairy products, vegetables, and the like, for example, but the viewpoint and granularity of such "group" classification are not limited to this. One or both of the food information and the drink information may include those related to so-called supplements (health foods). The eating-and-drinking information is, but is not limited to, information that is input by an evaluator such as a user who performed evaluation of the eating-and-drinking status. For example, the eating-and-drinking information may be information resulting from measurement or evaluation by an evaluation device or the like. For example, the types and amounts of food or drink consumed may have different effects on digestive motility.

The activity status information is information regarding the user's activity status. The activity status herein refers to a status related to lifestyle habits (i.e., actions and behaviors that the user repeatedly performs in daily life) excluding the eating-and-drinking status. That is to say, the activity status information may include information regarding lifestyle habits excluding the eating-and-drinking information. In this embodiment, the activity status information includes, but is not limited to, at least one of sleep information regarding sleep (sleep duration, sleep quality, etc.) and exercise information regarding exercise (the number of steps, the amount of calories burned, whether or not a user engages in habitual exercise, intensity of exercise, frequency of exercise, etc.). For example, the activity status information may include information regarding whether or not a user smokes, smoking history, and the like. The activity status information may be information acquired by an activity tracker installed in a device (e.g., a wearable terminal or other portable terminal, etc.) that the user carries around or wears, or information input by an evaluator such as a user who performed evaluation, for example.

The abdominal sounds refer to sounds emanating from the abdomen of a user. The abdominal sounds may include gut sounds emanating from the intestines, for example. The abdominal sounds may include sounds emanating due to blood flow in the abdomen (e.g., abdominal aortic sounds) and sounds emanating from organs such as the stomach.

The sound information refers to information obtained based on abdominal sounds. The sound information may be the recorded abdominal sound data itself, or data obtained by processing or editing the data.

FIG. 1 is a diagram showing the outline of an information processing system 1 according to Embodiment 1 of the present invention.

In this embodiment, the information processing system 1 includes an information processing apparatus 100 and terminal apparatuses 600. The information processing apparatus 100 and the terminal apparatuses 600 can communicate with each other via a network such as a local area network or the Internet, for example. The configuration of the information processing system 1 is not limited to this. There is no limitation on the number of each type of apparatuses included in the information processing system 1, and other apparatuses may be included in the information processing system 1.

Users of the information processing system 1 can use the information processing system 1 using the terminal apparatuses 600. In FIG. 1, portable information terminal apparatuses such as so-called smartphones, each of which has a built-in microphone 681, are shown as the terminal apparatuses 600, for example, but the terminal apparatuses 600 are not limited to such portable information terminal apparatuses. For example, terminal apparatuses 600*b* that are personal computers (PC) such as laptop computers may be used, or other apparatuses such as tablet-type information terminal apparatuses may be used. An external microphone 681*b* may be used as the microphone. In the following examples, it is assumed that portable information terminal apparatuses such as smartphones are used as the terminal apparatuses 600, but there is no limitation to this.

Figure 2:
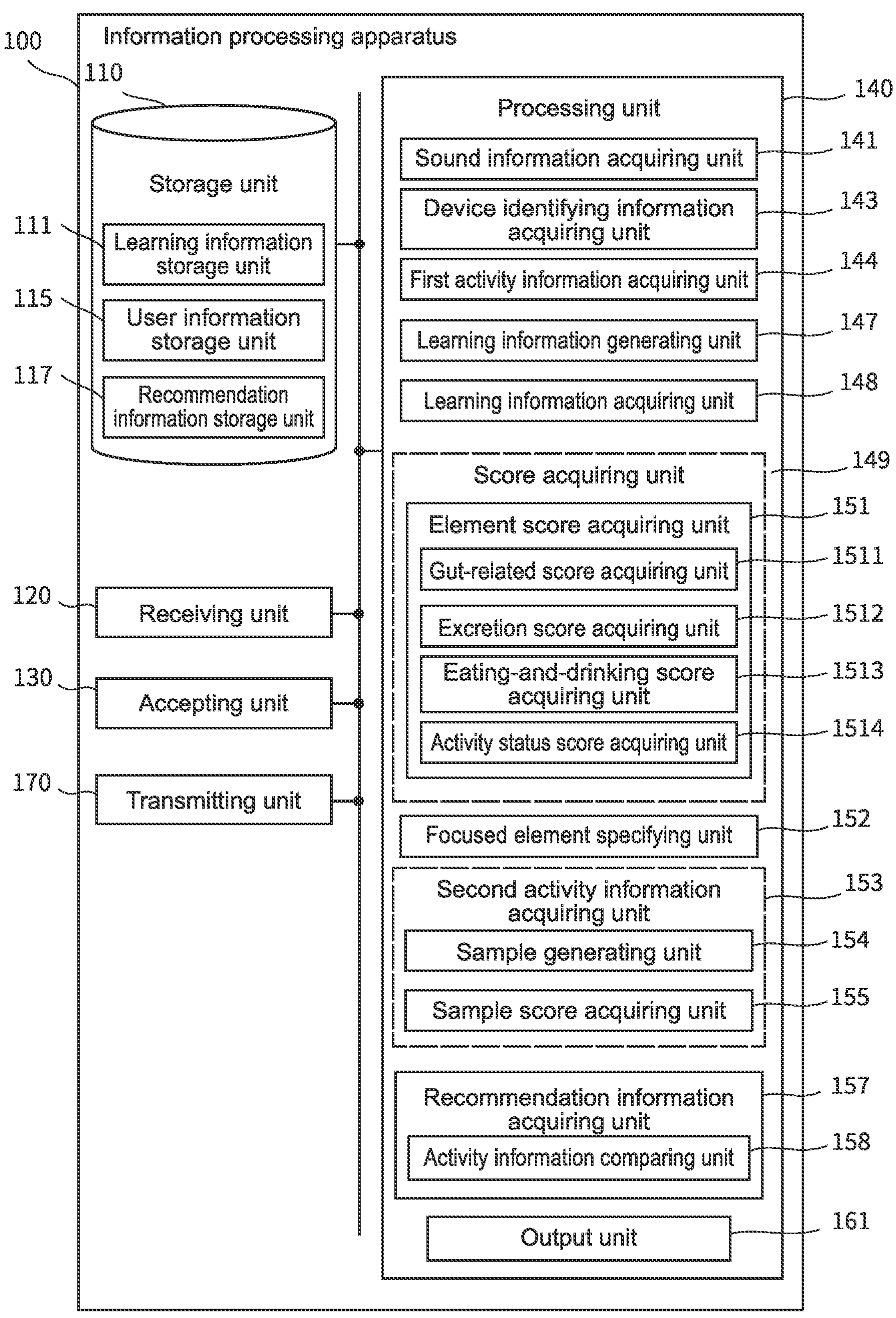
FIG. 2 is a block diagram of an information processing apparatus in the embodiment.
Figure 3:
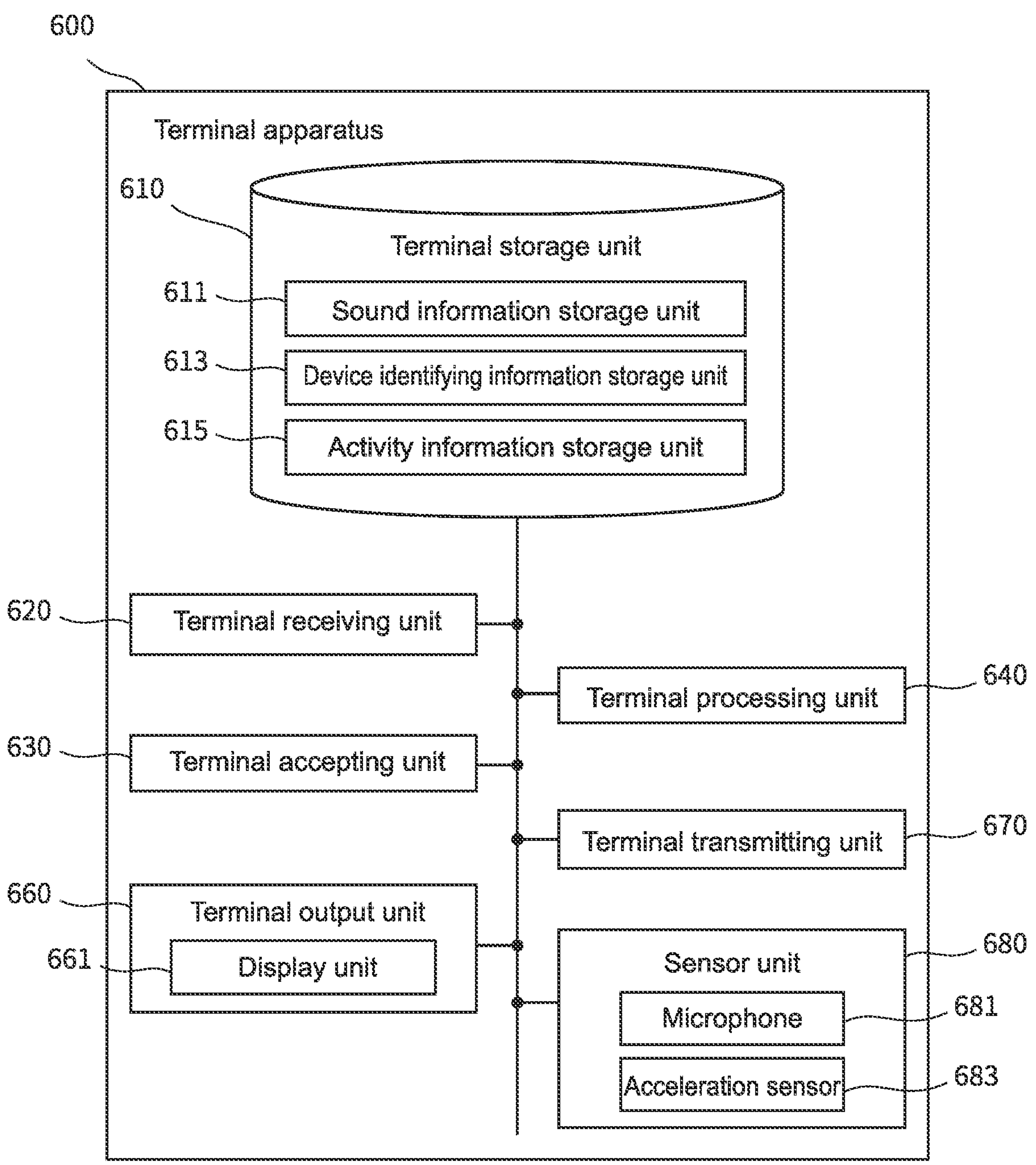
FIG. 3 is a block diagram of a terminal apparatus in the embodiment.

FIG. 2 is a block diagram of the information processing apparatus 100 in the embodiment. FIG. 3 is a block diagram of a terminal apparatus 600.

As shown in FIG. 2, the information processing apparatus 100 includes a storage unit 110, a receiving unit 120, an accepting unit 130, a processing unit 140, and a transmitting unit 170. The information processing apparatus 100 is a server apparatus, for example.

The storage unit 110 includes a learning information storage unit 111, a user information storage unit 115, and a recommendation information storage unit 117.

Learning information for acquiring scores (hereinafter simply referred to as "learning information") that has been acquired in advance is stored in the learning information storage unit 111. In this embodiment, the learning information is generated such that activity information containing values of two or more parameters regarding an activity state of a user is taken as information that is to be input and a score regarding a health state of the user is taken as information that is to be output.

Furthermore, in this embodiment, learning information for sound information (alternatively referred to as "second learning information" hereinafter) that has been acquired in advance is stored in the learning information storage unit 111. The second learning information is generated such that, learning input information containing sound information is taken as information that is to be input and a value of a predetermined output indicator regarding an activity state of the guts is taken as information that is to be output.

In this embodiment, the learning information and the second learning information are generated using a so-called machine learning method. The learning information and the second learning information are generated by a learning information generating unit 147 and stored in the learning information storage unit 111, for example, as described later, but there is no limitation to this. That is to say, for example, the learning information or the second learning information generated by an apparatus that is different from the information processing apparatus 100 may be stored in the learning information storage unit 111. For example, one of the learning information and the second learning information may be generated by the learning information generating unit 147, and the other may be generated by an apparatus that is different from the information processing apparatus 100. The learning information is not limited to those generated using a machine learning method. The learning information may be a table indicating the correspondence between an input vector based on information for input or the like and information that is to be output, a function representing the relationship between an input vector based on the information for input or the like and information for generating information that is to be output, or the like, as with the above-described classifier.

In this embodiment, the learning information is prepared for each user. That is to say, each piece of learning information is stored in the learning information storage unit 111 in association with a user identifier for identifying a user.

Furthermore, in this embodiment, multiple pieces of second learning information are prepared. The pieces of second learning information are each stored in the learning information storage unit 111 in association with device identifying information. The device identifying information is information corresponding to the sound information contained in the learning input used to generate the second learning information, and is information for identifying the type and the like of a device used to acquire, that is, record abdominal sounds corresponding to the sound information, for example. The device identifying information may also be said to be information for identifying a method used to record abdominal sounds, for example. The device may mean a microphone used to record abdominal sounds, or an apparatus set including the microphone, for example. Specific examples of the device identifying information include, but are not limited to, a symbol for identifying the model of a device used to record abdominal sounds and a symbol for identifying the type of a device used to record abdominal sounds (e.g., whether a smartphone's built-in microphone was used or an external microphone was used), for example. Any symbol with which the origin of the learning input information, such as the recording method or the processing method of recorded abdominal sounds (e.g., whether or not a filter was applied, type, sound quality adjustment, etc.), can be identified at some granularity can be used as the device identifying information.

User information is stored in the user information storage unit 115. In this embodiment, the user information is information for associating a user identifier, which is an identifier for identifying a user who uses the information processing system 1, and information regarding the user. The user information may contain various types of information. For example, the user information may contain information transmitted from the terminal apparatus 600 that is used by the user, information on the user acquired by the information processing apparatus 100 as described later, and the like. The information transmitted from the terminal apparatus 600 that is used by the user corresponds to sound information, device identifying information, activity information, and the like as described later, as well as the user's health state information, for example. The information on the user acquired by the information processing apparatus 100 corresponds to information regarding the frequency of gut sounds, a gut state estimation result, element scores, a score, and the like as described later, for example. User information transmitted from other external apparatuses and the like may be stored in the user information storage unit 115.

In this embodiment, association information that is used to output recommendation information is stored in the recommendation information storage unit 117. Recommendation information for a user is information indicating a matter the user has to pay attention to with respect to the activity state. In this embodiment, the recommendation information is set as indicating a matter the user is to execute, and contains information that identifies a task to be performed. The association information is information indicating the correspondence between a parameter identifier for identifying each of two or more parameters and task identifiers for identifying two or more tasks, for example. In this embodiment, in the association information, one or at least two task identifiers related to each of multiple parameters are associated with a parameter identifier indicating that parameter. The correspondence between parameters and tasks is set in advance, for example. For example, if the user's continuous execution of a task can be equated with causing a change in the value of one or at least two specific parameters in the user's activity information, the task can be taken as corresponding to the parameters. Specifically, for example, a task such as "drink one bottle of milk a day" is associated with a parameter such as "the amount of dairy products consumed". For example, a task such as "walk at least 6000 steps" may be associated with a parameter such as "amount of calories burned" or a parameter such as "number of steps". For example, a parameter such as "number of steps" may be associated with a task such as "walk at least 6000 steps" as well as a task such as "walking at least 30 minutes" or "walking up stairs". If a recommendation information acquiring unit 157 is configured to output recommendation information without using the association information as described later, the recommendation information storage unit 117 does not have to be provided.

In this embodiment, it is sufficient that the two or more parameters include at least any of those for drink consumption regarding consumption of drink, food consumption regarding consumption of food, lifestyle habits regarding activities other than eating and drinking, and exercise information regarding exercise.

The receiving unit 120 receives information transmitted from another apparatus. The receiving unit 120 accumulates the received information in the storage unit 110, for example. In this embodiment, the user inputs information using the terminal apparatus 600 and transmits the information to the information processing apparatus 100, for example. The receiving unit 120 can accumulate each piece of transmitted information in the storage unit 110 in association with a user identifier. In this embodiment, it is also possible to receive sound information transmitted from each terminal apparatus 600 and accumulate the sound information in the storage unit 110 in association with a user identifier, as will be described later. In the case of receiving these pieces of information from the terminal apparatus 600, the receiving unit 120 can specify a user identifier of the user pertaining to the transmission based on the transmitted information.

The accepting unit 130 accepts information input using an input, part (not shown) connected to the information processing apparatus 100. The accepting unit 130 accumulates the accepted information in the storage unit. 110, for example. The information may be input by any part such as a numeric keypad, a keyboard, a mouse, or a menu screen. The accepting unit 130 may accept information input through an input operation performed using a reading apparatus (e.g., a code reader, etc.) connected to the information processing apparatus 100 (e.g., including information read by the apparatus).

The accepting unit 130 may be taken to accept the information received by the receiving unit 120, as information input to the information processing apparatus 100. That is to say, the input of information to the information processing apparatus 100 may be interpreted to mean that these pieces of information are indirectly input to the information processing apparatus 100 by the user via the terminal apparatus 600 or the like, or directly input to the information processing apparatus 100 by the user using an input part. The input of information to the information processing apparatus 100 may also be taken to mean that the information is given to the information processing apparatus 100 by the user executing a program that automatically generates information or giving various types of information to a program and causing the program to function.

The processing unit 140 includes a sound information acquiring unit 141, a device identifying information acquiring unit 143, a first activity information acquiring unit 144, a learning information generating unit 147, a learning information acquiring unit 148, a score acquiring unit 149, a second activity information acquiring unit 153, a recommendation information acquiring unit 157, and an output unit 161. The processing unit 140 performs various types of processing. The various types of processing are processing that is performed by the constituent units of the processing unit 140 as follows, for example.

The sound information acquiring unit 141 acquires sound information on a user. In this embodiment, the sound information acquiring unit 141 acquires sound information from abdominal sounds of the user, which was transmitted from the terminal apparatus 600 of the user and received by the receiving unit 1120.

The device identifying information acquiring unit 143 acquires device identifying information corresponding to the sound information. In this embodiment, the device identifying information is, but is not limited to, information transmitted from the terminal apparatus 600 of the user in association with sound information. The device identifying information acquiring unit 143 may be configured to acquire device identifying information stored in advance in the storage unit 110 as information for identifying the terminal apparatus 600 of the user.

The first activity information acquiring unit 144 acquires first activity information containing respective values of the two or more parameters, which are values according to the activity state of the user. In this embodiment, the first activity information includes, but is not limited to, excretion-related information, eating-and-drinking information, and activity status information (i.e., exercise information or sleep information). The first activity information acquiring unit 144 acquires the information stored in the user information storage unit 115, for example. Furthermore, the first activity information acquiring unit 144 may acquire the user's health state information from the user information storage unit 115 or the like.

The learning information generating unit 147 generates learning information using a machine learning method. A machine learning method can be used as follows, for example. That is to say, a learning model in which activity information of a user is taken as input and a score acquired for the user is taken as output is configured using a machine learning method. For example, two or more pairs of learning input information and an output value are prepared in advance, the two or more pairs of information are given to a module for configuring a learning model for machine learning to configure a learning model, and the configured learning model is accumulated in the learning information storage unit 111 as learning information. That is to say, the learning information generating unit 147 generates learning information using two or more pieces of training data having activity information containing values of two or more parameters regarding an activity state of a user and a score regarding a health state of the user.

Furthermore, the learning information generating unit 147 generate, second learning information using a machine learning method. A machine learning method can be used as follows, for example. That is to say, a learning model in which learning input information containing sound information is taken as input and a value (output value) of a predetermined output indicator regarding an activity state of the guts is taken as output, is configured using a machine learning method. For example, two or more pairs of learning input information and an output value are prepared in advance, the two or more pairs of information are given to a module for configuring a learning model for machine learning to configure a learning model, and the configured learning model is accumulated in the learning information storage unit 111 as second learning information. It is sufficient that combinations of learning input information and an output value are prepared in advance. It is also possible to re-generate learning information at a predetermined point in time using a combination of sound information and an output value newly acquired by the information processing apparatus.

There is no limitation on the machine learning method, and examples thereof include deep learning such as convolutional neural networks (CNN), random forests, and SVR. For example, functions in various machine learning frameworks and various existing libraries, such as fastText, tinySVM, random forest, and TensorFlow, can be used for the machine learning.

In this embodiment, the learning information generating unit 147 generates learning information for a user (i.e., a target user) corresponding to a score acquired by the score acquiring unit 149 as described later, using training data having activity information of the user and the score. The learning information generating unit 147 accumulates the generated learning information in the learning information storage unit 111 in association with a user identifier of the user. Accordingly, learning information for each user is stored in the learning information storage unit 111. The learning information generating unit 147 may be configured to generate second learning information for each user and accumulate it in the learning information storage unit 111 in association with a user identifier in a similar manner. The learning information and the second learning information are not limited to those generated for a specific user. The information may be generated such that it can be used in common for multiple users, and, at this time, for example, the information may be generated such that it can be used in common for multiple users who can be equated with each other with respect to a predetermined attribute. Such learning information and the like can be configured using various methods, such as by using pieces of training data respectively regarding multiple users all at once.

The learning information acquiring unit 148 acquires learning information and second learning information. In this embodiment, if the second activity information acquiring unit 153 performs processing using learning information, the learning information acquiring unit 148 acquires learning information corresponding to a user identifier of the target user, from the learning information storage unit 111. If the score acquiring unit 149 performs processing using second learning information as described later, the learning information acquiring unit 148 acquires second learning information from the learning information storage unit 111. In this case, the learning information acquiring unit 148 preferably acquires second learning information corresponding to the device identifying information acquired by the device identifying information acquiring unit 143, from the learning information storage unit 111. If second learning information is generated for each user, it is also possible to acquire second learning information corresponding to a user identifier of a user for which processing using the second learning information is to be performed.

The learning information acquiring unit 148 may be configured to acquire the learning information and the second learning information stored in another apparatus that is different from the information processing apparatus 100, form the other apparatus. For example, if the learning information and the second learning information stored in the other apparatus are always used, the information processing apparatus 100 does not have to include the learning information storage unit 111.

The score acquiring unit 149 includes an element score acquiring unit 151. The element score acquiring unit 151 includes a gut-related score acquiring unit 1511, an excretion score acquiring unit 1512, an eating-and-drinking score acquiring unit 1513, and an activity status score acquiring unit 1514.

In this embodiment, the score acquiring unit 149 acquires health state information regarding a health state of a user. The health state information may be information input by a user or the like in advance, information acquired by a wearable terminal or the like worn by the user or a portable terminal or the like held by the user, or information stored in an external database or the like in which user information is recorded, for example, as described above.

In this embodiment, the score acquiring unit 149 acquires a score regarding a health state of the user, using the acquired health state information and the first activity information acquired by the first activity information acquiring unit 144. In this embodiment, the score is constituted by element scores respectively for two or more evaluation elements regarding the health state of the user. In this embodiment, the score acquiring unit 149 is configured to be capable of acquiring the score using the element scores acquired by the element score acquiring unit 151. That is to say, the element score acquiring unit 151 acquires the element scores respectively using the gut-related score acquiring unit 1511, the excretion score acquiring unit 1512, the eating-and-drinking score acquiring unit 1513, and the activity status score acquiring unit 1514. The element score acquiring unit 151 causes the constituent units to acquire element scores respectively for two or more evaluation elements based on the input information, as will be described later. The two or more evaluation elements may be gut-related elements, such as excretion, drink, food, an activity status, and the like, for example. That is to say, in this embodiment, for example, a gut movement score, a gut state score, an excretion score regarding excretion by a user, a food score regarding food consumed by the user, a drink score regarding drink consumed by the user, and an activity status score regarding an activity status of the user, and the like are used as the element scores. The scores are numerical values representing the state or degree of goodness of a matter of interest, symbols indicating a grade, or the like, and is information easily understandable for users.

In this embodiment, specifically, for example, an element score based on sound information from abdominal sounds of a user is acquired as one of the element scores. That is to say, it can be said that the score acquiring unit 149 is configured to acquire a score based on sound information.

In this embodiment, the score acquiring unit 149 acquires second learning information configured using two or more pieces of training data having input information containing the sound information and output information regarding a predetermined output indicator regarding an activity state of the guts. The score acquiring unit 149 acquires second learning information stored in from the learning information storage unit 111, for example, but there is no limitation to this. The score acquiring unit 149 acquires the score based on output information acquired by applying the second learning information to input information containing the sound information acquired by the sound information acquiring unit 141. In this embodiment, the score acquiring unit 149 acquires a value of a predetermined output indicator using the acquired second learning information, and acquires a score using the value of the output indicator. The processing for acquiring a value of a predetermined output indicator is performed by the gut-related score acquiring unit 1611 described later, for example. For example, at least one of the bowel movement state and the number of peristalsis movements of the guts per unit time is used as the predetermined output indicator. The number of peristalsis movements of the guts may also be said to be the frequency of gut sounds at a predetermined level or greater (alternatively referred to simply as the "frequency of gut sounds" hereinafter).

The gut-related score acquiring unit 1511 acquires a gut state score regarding a bowel movement state (normal, diarrhea, constipation, etc.) and a gut movement score regarding peristalsis movements (frequency, etc.) of the guts, using the sound information acquired by the sound information acquiring unit 141 and the second learning information. In this embodiment, the gut-related score acquiring unit 1511 inputs the sound information acquired by the sound information acquiring unit 141 to the second learning information using a machine learning method, thereby acquiring a value of an output indicator. Then, the gut-related scores (a gut state score and a gut movement score) are acquired based on the value of the output indicator.

In this embodiment, the sound information that is used by the learning information generating unit 147 as learning input information and the sound information that is input by the gut-related score acquiring unit 1511 are spectrograms obtained by representing, in a predetermined form, results of Fourier transform analysis or fast Fourier transform analysis performed on the sound data (which may be processed) obtained by recording abdominal sounds. The sound information may be sound data (which may be processed) itself or data converted to other formats. The sound information that is used by the learning information generating unit 147 as learning input information and the sound information that is input by the gut-related score acquiring unit 1511 may be prepared by the processing unit 140. Sound information in the form of a spectrogram may be prepared in advance by a device other than the information processing apparatus 100, such as a device that recorded abdominal sounds, and transmitted to the information processing apparatus 100.

The learning information generating unit 147 and the gut-related score acquiring unit 1511 may be configured to use learning input information containing user information such as health state information, in accordance with generation and use of the second learning information. In this case, the second learning information that is generated may be stored in the learning information storage unit 111, for each type by which users can be classified according to the user information, in association with an identifier for identifying the type. It is sufficient that the gut-related score acquiring unit 1511 is configured to acquire second learning information of a type corresponding to an identifier specified based on the user information, from the learning information storage unit 111, and acquire a gut-related score using the second learning information. Accordingly, more accurate output results can be obtained.

The excretion score acquiring unit 1512 acquires an excretion score based on the excretion-related information.

The eating-and-drinking score acquiring unit 1513 acquires a drink score and a food score based on the eating-and-drinking information.

The activity status score acquiring unit 1514 acquires an activity status score based on the activity status information.

These units of the element score acquiring unit 151 acquire element scores based on output indicator values or various types of activity information, according to whether or not an output indicator value or the content of various types of activity information satisfies a predetermined condition, for example. The predetermined condition may be set for each element and for each viewpoint of the element. For example, an element score can be acquired by reflecting a first predetermined point in the element score if a predetermined condition is satisfied or by reflecting a second predetermined point in the element score if the predetermined condition is not satisfied. Specifically, for example, in the case in which the frequency of gut sounds is obtained as an output indicator value, if the frequency of the gut sounds is within a predetermined range, a first predetermined point may be added to a gut movement score serving as the base, or otherwise a second predetermined point may be subtracted from the gut movement score serving as the base.

The constituent units of the element score acquiring unit 151 accumulate each acquired element score in the user information storage unit 115 in association with a user identifier.

The constituent units of the element score acquiring unit 151 may compare an output indicator value or the content of various types of activity information with a predetermined reference, and calculate an element score by using a predetermined calculation formula according to the comparison result. Also, multiple threshold values serving as a reference may be prepared, and a predetermined point corresponding to a condition range that an output indicator value or the content of various types of activity information matches may be reflected in the element score. Also, multiple evaluation viewpoints (viewpoints for comparison with a reference value, etc,) may be provided for each element such as an intestinal movement, a gut state, excretion, drink, food, or an activity status, and a predetermined point may be reflected in the element score according to a result of comparison with a reference value for each viewpoint. The corresponding point may be reflected in the element score based on information (e.g., an n-dimensional look-up table) that maps the points to be reflected, in advance, in a space composed of multiple viewpoint axes.

The constituent units of the element score acquiring unit 151 may acquire an element score based on element scores acquired in the past for the user and stored in the user information storage unit 115, output indicator values or various types of activity information in the past, or the like. For example, it is also possible to acquire a current element score by reflecting a current point in an element score acquired in the past. It is also possible to acquire an element score using an average value or the like of output indicator values or various types of activity information in a past predetermined period and current output indicator values or various types of activity information. It is also possible to acquire an element score using points (by adding the points, etc.) respectively specified for a predetermined number of past output indicator values or various types of activity information and current output indicator values or various types of activity information.

The constituent units of the element score acquiring unit 151 may set factors such as conditions set for acquiring such element scores, a reference value for use in comparison, an element score serving as the base, a point that is to be reflected in the element score, and a method for reflecting a point in the element score (addition, subtraction, multiplication, etc.) as appropriate based on the user's health state information. That is to say, the constituent units of the element score acquiring unit 151 may acquire an element score based on the user's health state information. Specifically, for example, the constituent units of the element score acquiring unit 151 may be configured to acquire an element score by applying different factors according to the user's sex and age.

In this embodiment, the score acquiring unit 149 acquires a score using the gut movement score and the gut state score acquired by the gut-related score acquiring unit 1511, the excretion score acquired by the excretion score acquiring unit 1612, the drink score and the food score acquired by the eating-and-drinking score acquiring unit 1513, and the activity status score acquired by the activity status score acquiring unit 1514 in this manner. The score may be acquired by applying element scores to a predetermined calculation formula and performing calculation using a predetermined method such as addition or multiplication, for example. The score may be acquired by using a learning model configured using a machine learning method such that element scores are taken as input and a score is taken as output, for example. The element scores may be changed from the value acquired by the constituent units of the element score acquiring unit 151, such as being normalized or otherwise as necessary, and used to obtain a score.

The score acquiring unit 149 accumulates the acquired score in the user information storage unit 115 in association with a user identifier.

The score acquiring unit 149 may acquire a current score based on scores acquired in the past for the user and stored in the user information storage unit 115. For example, it is also possible to acquire a current score by reflecting a point according to the current element scores in a score serving as the base based on the past score.

The score acquiring unit 149 may change a predetermined method used to acquire such a score, as appropriate based on the user's health state information. Specifically, for example, the score acquiring unit 149 may be configured to acquire a score by performing calculation or the like using element scores according to different methods according to the user's sex, age, height, weight, medical history, results of predetermined questionnaires, and the like. That is to say, the score acquiring unit 149 may acquire a score using a method corresponding to the user's health state information.

In this embodiment, the focused element specifying unit 152 compares a past score acquired for a user (past score) and a new score newly acquired by the score acquiring unit 149 for the same user (new score). Then, the focused element specifying unit 152 determines whether or not the comparison result satisfies a predetermined condition. Furthermore, the focused element specifying unit 162 specifies one or more evaluation elements to be focused on, out of the two or more evaluation elements, according to the determination result. The specifying may be rephrased as making it possible to distinguish that evaluation element from other evaluation elements, by setting a flag or the like. The terms"past" and "new" may be expressed based on a past point in time. The predetermined condition may be that the new score is a value (lower score) indicating that the condition is worse than that indicated by the past score, that the difference between the new score and the past score is greater than a predetermined threshold value, that the ratio between the new score and the past score is greater than a predetermined threshold value, or a combination thereof, for example. Such a condition may be referred to as a condition regarding the relationship between the size of the difference between the scores and the predetermined value. Also, the predetermined condition may be that the difference between the element score in the new score and the element score in the past score is greater than a predetermined threshold value, that the element score in the new score is a value (lower score) indicating that the condition is worse than that indicated, by the element sore in the past score, that the ratio of the two element scores is greater than a predetermined threshold value, or a combination thereof, for example. Such a condition may be referred to as a condition regarding the relationship between the size of the difference between the element scores and the predetermined value. In this embodiment, for example, if a condition regarding the relationship between the size of the difference between the element scores and the predetermined value is satisfied for an evaluation element, the evaluation element is specified.

The focused element specifying unit 152 may be configured not to specify any evaluation element in the case in which the result of the comparison between the scores does not satisfy the predetermined condition.

The second activity information acquiring unit 153 includes a sample generating unit 154 and a sample score acquiring unit 155. The second activity information acquiring unit 153 acquires second activity information, using the learning information acquired by the learning information acquiring unit 148.

In this embodiment, the second activity information is activity information in which a value of at least one of the two or more parameters is different from that in the first activity information acquired by the first activity information acquiring unit 144. The score acquired by applying the learning information to the second activity information is different from the score acquired by the score acquiring unit 149 using the first activity information acquired by the first activity information acquiring unit 144. In other words, the second activity information acquiring unit 153 acquires, using the learning information, second activity information in which a value of at least one of the two or more parameters is different from that in the first activity information, and in which a score acquired by applying the learning information to the second activity information is different from the score acquired by the score acquiring unit 149.

In particular, in this embodiment, the second activity information acquiring unit 153 acquires second activity information in which a focused element score that is regarding the evaluation element specified by the focused element specifying unit 152 and that constitutes a score acquired by applying the learning information to the second activity information is different from the focused element score that constitutes the score acquired by the score acquiring unit 149. For example, if one element score is lower in a new score than in a past score, the focused element specifying unit 152 specifies that evaluation element. Thus, the second activity information acquiring unit 153 acquires second activity information in which a score with the element score different from that in the score acquired by the score acquiring unit 149 is acquired.

In this embodiment, the second activity information acquiring unit 153 causes the sample score acquiring unit 155 to acquire the score using activity information (referred to as sample activity information) generated by the sample generating unit 154 and serving as a candidate for second activity information, and determines whether or not to acquire the sample activity information as the second activity information, based on the score and the score acquired by the score acquiring unit 149.

That is to say, the sample generating unit 154 generates sample activity information by changing values of selected one or more parameters with respect to the first activity information. The values can be changed in various ways. For example, the values can be increased or decreased by a predetermined value or by a predetermined percentage with respect to the first activity information. The sample score acquiring unit 155 acquires the score by applying the learning information acquired by the learning information acquiring unit 148 to the sample activity information. The thus acquired score may be referred to as "sample score" for the sake of convenience.

The second activity information acquiring unit 153 compares the sample score and the score acquired by the score acquiring unit 149, and acquires the sample activity information as the second activity information based on the comparison result. For example, as a result of comparing both scores, if a condition regarding the relationship between the change in the focused element score and the predetermined value is satisfied, such as the difference between the focused element scores for the evaluation element specified by the focused element specifying unit 152 being a predetermined value or greater or being within the range of a predetermined value, the second activity information acquiring unit 153 acquires the sample activity information as the second activity information.

The second activity information acquiring unit 153 may acquire the sample activity information as the second activity information, according to a result of a comparison between the sample score and the score acquired by the score acquiring unit 149, regardless of each element score. If the second activity information is acquired according to the overall comparison result regardless of the comparison result of each element score, the focused element specifying unit 152 does not have to be provided. The acquisition of the second activity information according to the overall comparison result may be performed only when none of the focused elements are specified by the focused element specifying unit 152, or may be performed every time.

In this embodiment, the second activity information acquiring unit 153 may acquire the sample activity information as the second activity information only in the case in which the focused element score in the sample score is a value indicating that the user's state or status is more ideal for the corresponding evaluation element. In other words, the second activity information acquiring unit 153 may acquire second activity information in which a focused element score of a score acquired by applying the learning information thereto is higher than the focused element score of the score acquired by the score acquiring unit 149. The second activity information acquiring unit 153 may acquire second activity information in which a score acquired by applying the learning information thereto is higher than the score acquired by the score acquiring unit 149.

There is no limitation on the method using which the second activity information acquiring unit 153 acquires second activity information. For example, the second activity information acquiring unit 153 may be configured to acquire one of the pieces of first activity information acquired in the past, and, if a score acquired by applying the learning information acquired by the learning information acquiring unit 148 to this piece of first activity information is higher than the wore acquired by the score acquiring unit 149, acquire the first activity information as the second activity information. This may be expressed as the sample activity information is generated based on the first activity information acquired in the past. For example, the sample generating unit 154 may generate sample activity information by changing values of selected one or more parameters with respect to the first activity information, based on the first activity information acquired for the user in the past. For example, the sample activity information may be generated by changing values of parameters corresponding to the past activity or state. If the second activity information is acquired in this manner, recommendation information that is easy for individual users to reflect in their future activities can be output.

The recommendation information acquiring unit 157 includes an activity information comparing unit 158. The activity information comparing unit 158 compares the first activity information acquired by the first activity information acquiring unit 144 and the second activity information acquired by the second activity information acquiring unit 153. The recommendation information acquiring unit 157 acquires recommendation information regarding at least one of the two or more parameters regarding the activity state of the user, according to a result of the comparison between the first activity information and the second activity information.

More specifically, in this embodiment, the activity information comparing unit 158 acquires parameter identifiers of one or more parameters whose values differ between the first activity information and the second activity information, for example. If a condition regarding the size of the difference between the values of the first activity information and the second activity information is satisfied for a parameter, the activity information comparing unit 158 acquires a parameter identifier of the parameter, for example. Various conditions can be set as the condition regarding the size of the difference between the values, such as that the difference between the values is greater than a predetermined value or that the ratio of one to the other is greater than a predetermined value, for example. If a predetermined condition is satisfied for one or more parameters whose values differ between the first activity information and the second activity information, the activity information comparing unit 18 may acquire parameter identifiers of the parameters. For example, if a parameter has values that differ between the first activity information and the second activity information and the relationship between a value of the parameter in the first activity information and a predetermined value is in a predetermined state, the activity information comparing unit 158 may acquire a parameter identifier of the parameter. The predetermined state is, for example, but not, limited to, being large, being small, the difference thereof being a predetermined value or greater, or the ratio thereof being a predetermined value or greater.

The recommendation information acquiring unit 157 acquires a task identifier corresponding to the parameter identifier acquired by the activity information comparing unit 158, by referring to the association information stored in the recommendation information storage unit 117. The recommendation information acquiring unit 157 acquires recommendation information, using the acquired task identifier and information corresponding thereto. For example, information indicating the content or description of the task specified with a task identifier or the like is configured and acquired as the recommendation information. Such information can be configured using information stored the storage unit 110 in advance in association with a task identifier, for example, but the configuring method is not limited to this. The acquiring recommendation information may mean acquiring only a task identifier as the recommendation information, for example.

In this embodiment, in the case of acquiring a task identifier corresponding to the parameter identifier acquired by the activity information comparing unit 158, the recommendation information acquiring unit 157 may acquire a corresponding task identifier out of the task identifiers of tasks previously executed by the user. In this case, it is also possible to acquire a corresponding task identifier out of the task identifiers of tasks previously executed by the user but, are not being currently executed. Such processing can be realized by accumulating history information that enables retrieval of task identifiers of tasks executed in the past in the user information storage unit 115 for each user, and referring to this history information, but the realizing method is not limited to this.

Furthermore, the recommendation information acquiring unit 157 may be configured to output recommendation information without using association information. For example, the recommendation information acquiring unit 157 may be configured to acquire information on the parameter identifier acquired by the activity information comparing unit 158 or a parameter thereof, as the recommendation information. The information to be recommendation information for a parameter can be configured using information stored the storage unit 110 in advance in association with the parameter identifier, for example, but the configuring method is not limited to this. The recommendation information may be information obtained by combining a task identifier corresponding a parameter identifier and other information as appropriate. Even when a parameter identifier or information on the parameter is used as the recommendation information, it is possible to make users aware of their own activities that may affect their scores. The recommendation information acquiring unit 157 may use information corresponding to a difference for at least one parameter, as the recommendation information, according to a result of the comparison between the first activity information and the second activity information. For example, the recommendation information may be configured such that the difference between the actual value, which is the first activity information, and the target value, which is the second activity information, with respect to the value indicating the performance of a predetermined activity, is the task to be achieved by the user.

In this embodiment, the recommendation information acquiring unit 157 is preferably configured to output recommendation information containing information regarding an order of significance of an influence given on the score, regarding at least two parameters out of the two or more parameters regarding the activity state of the user, using the first activity information and the two or more pieces of second activity information. That is to say, the activity information comparing unit 158 compares the first activity information with two or more pieces of second activity information having different values for parameters that differ from each other, and acquires one or more parameter identifiers for each. The recommendation information acquiring unit 157 orders (ranks) the acquired two or more parameter identifiers according to a result of a comparison between the sample score corresponding to each piece of second activity information and the score acquired by the score acquiring unit 149 (which may be a result of a comparison between element scores), and acquires recommendation information according to the order. For example, the recommendation information acquiring unit 157 orders the parameter identifiers such that the rank of the parameter identifier acquired for the second activity information with a larger difference in score is higher. The recommendation information acquiring unit 157 acquires recommendation information in which information on the rank is associated with information such as each parameter identifier or a task identifier corresponding thereto, for example. This makes it possible for the user to know the order in which the multiple parameters and corresponding tasks and other information have a large influence on the score, and thus to know the priority level when working on or being aware of them. It is also possible to perform a sensitivity analysis of the influence of each parameter value on the score, and use the results of the sensitivity analysis to assign an order to the parameter identifiers. The recommendation information may contain information that specifies the order of output such that the information such as the multiple parameters is output by the output unit 161 in the specified order.

The output unit 161 outputs the recommendation information acquired by the recommendation information acquiring unit 157. The output unit 161 outputs the score acquired by the score acquiring unit 149, but may not output the score. The output unit 161 may also output information (e.g., an identifier) on an evaluation element specified by the focused element specifying unit 152. When outputting a score and information on an evaluation element, the recommendation information and the score may be output on the same occasion or on separate occasions. For example, recommendation information acquired in response to a score may be output after a predetermined time after the score or the like is output. In this embodiment, the output unit 161 outputs the recommendation information by transmitting it to the terminal apparatuses 600, but there is no limitation to this. For example, the output may be performed by displaying the recommendation information in text or images on a display screen included in the information processing apparatus 100.

The transmitting unit 170 transmits information via a network to another apparatus constituting the information processing system 1. The transmitting unit 170 transmits information to the terminal apparatus 600, for example. In other words, the transmitting unit 170 outputs information to the terminal apparatus 600, for example.

Next, the configuration of the terminal apparatus 600 will be described.

As shown in FIG. 3, the terminal apparatus 600 includes a terminal storage unit 610, a terminal receiving unit 620, a terminal accepting unit 630, a terminal processing unit 640, a terminal output unit 660, a terminal transmitting unit 670, and a sensor unit 680. The terminal output unit 660 includes a display unit 661. The sensor unit 680 includes a microphone 681 and an acceleration sensor 683.

The terminal storage unit 610 includes a sound information storage unit 611, a device identifying information storage unit 613, and an activity information storage unit 615.

Sound information recorded using the sensor unit 680 of the terminal apparatus 600 is accumulated in the sound information storage unit 611. The sound information, which is transmitted by the terminal transmitting unit 670 to the information processing apparatus 100, may be deleted from the sound information storage unit 611 when the transmission is completed, retained as it is until a predetermined period elapses, or retained permanently until a deletion operation is performed by the user.

Device identifying information is stored in the device identifying information storage unit 613. The device identifying information is, but is not limited to, information with which the model of the terminal apparatus 600 can be identified. Different information may not be writable to the device identifying information storage unit 613.

Activity information is accumulated in the activity information storage unit 615. The activity information, which is transmitted by the terminal transmitting unit 670 to the information processing apparatus 100, may be deleted from the activity information storage unit 615 when the transmission is completed, retained as it is until a predetermined period elapses, or retained permanently until a deletion operation is performed by the user. The users health state information may also be stored in the activity information storage unit 615 and transmitted by the terminal transmitting unit 670 to the information processing apparatus 100.

The activity information that is accumulated in the activity information storage unit 615 may contain information input by the user or information based thereon. These pieces of information may be information accepted by the terminal accepting unit 630 or information acquired by the terminal processing unit 640 through calculation or the like based on the information accepted by the terminal accepting unit 630, for example.

Furthermore, the activity information that is accumulated in the activity information storage unit 615 may contain a measured value or information based thereon. These pieces of information may be information measured by the sensor unit 680 or information acquired by the terminal processing unit 640 through calculation or the like based on the information measured by the sensor unit 680, for example. Also, it may be information obtained through measurement or the like by a sensor apparatus communicably connected to the terminal apparatus 600 and transmitted to the terminal apparatus 600.

The terminal receiving unit 620 receives information transmitted from the information processing apparatus 100 or other apparatuses, via a network. The terminal receiving unit 620 accumulates the received information in the terminal storage unit 610, for example, such that it can be retrieved by the terminal processing unit 640 and the like.

The terminal accepting unit 630 accepts various operations input to the terminal apparatus 600 by the user who uses the terminal apparatus 600. The operations are performed using an input apparatus (not shown), for example, but there is no limitation to this. The terminal accepting unit 630 may accept an input operation by voice input using the microphone 681, for example.

The terminal processing unit 640 performs various information processing operations using the constituent units of the terminal apparatus 600.

The terminal output unit 660 outputs information by displaying it on the display unit 661, which is a display device, for example. The method for outputting information is not limited to this, and may also be performed by outputting voice or the like from a speaker or the like.

The terminal transmitting unit 670 transmits information acquired by the terminal processing unit 640 or the like, via a network, for example.

The sensor unit 680 may include a barometric pressure sensor and the like, as well as the microphone 681 and the acceleration sensor 683, for example. The sensor unit 68) performs recording using the microphone 681 and measurement of measurement matters, and outputs information such as obtained sound data and measured value. The obtained information is accumulated in the terminal storage unit 610, for example. In this example, the measured value is, but is not limited to, a value indicating changes in acceleration acquired by the acceleration sensor, a value indicating changes in atmospheric pressure acquired by the barometric pressure sensor, or the like, for example. The sensor unit 680 may include a pulse sensor, an illuminance sensor, a camera, and a location information sensor that can identify the position by GPS or the like, for example. The sensor unit 680 may be a timer or the like that measures the passage of time. In this embodiment, the sensor unit 680 functions as an activity tracker for acquiring information regarding the user's level of activity such as the amount of calories burned and the number of steps and information regarding the users lifestyle habits such as the user's wake-up time, bedtime, and commuting time. For example, information regarding the user's living environment such as the area in which the user lives, the climate, the noise environment, and the like may be acquired based on the measured values obtained by the sensor unit 680, and accumulated in the terminal storage unit 610.

Next, an example of an operation of the information processing apparatus 100 performed when a user uses the information processing system 1 according to this embodiment will be described. In this embodiment, the user can use the information processing system 1 by causing a predetermined application to work on the terminal apparatus 600 while accessing the information processing apparatus 100 via the terminal apparatus 600 or receiving information transmitted from the information processing apparatus 100, for example. The predetermined application may be a dedicated application that operates using information transmitted from the information processing apparatus 100, a web browser on which a web application provided by the information processing apparatus 100 is displayed in a usable manner, or the like, for example.

In this embodiment, the information processing system 1 is typically used as follows. That is to say, the user regularly records his or her own abdominal sounds using the terminal apparatus 600. The term "regularly" could mean daily, before or after every meal, or weekly, for example. Then, sound information is transmitted from the terminal apparatus 600 to the information processing apparatus 100, and a score is acquired by the information processing apparatus 100. The information processing apparatus 100 acquires recommendation information using the acquired score, and transmits (outputs) it to the terminal apparatus 600. The terminal apparatus 600 receives the recommendation score, and the terminal output unit 660 displays it on a display device. This allows the user to easily recognize tasks to work on and matters to be aware of regarding his or her health state based on information regarding his or her own guts and other activity information. The user can improve his or her health state by referring to the recommendation information and performing daily activities. In the case in which the information processing system 1 operates in this manner, the information processing apparatus 100 performs various operations as follows, for example. These operations are performed by the processing unit 140 executing control operations and the like while using the constituent units.

The storage unit 110 and the terminal storage unit 610 described above are preferably non-volatile recording media, but may alternately be realized by volatile recording media. The pieces of information respectively acquired by their corresponding apparatuses are respectively stored in these units, but there is no limitation on the procedure in which information is stored therein. For example, information and the like may be stored therein via a recording medium, information and the like transmitted via a communication line or the like may be stored therein, or information and the like input via an input device may be stored therein.

Furthermore, the processing unit 140 and the terminal processing unit 640 described above may be realized typically by MPUs, memories, or the like. Typically, the processing procedure of the processing unit 140 and the terminal processing unit 640 is realized by software, and the software is stored in a recording medium such as a ROM. The processing procedure may be realized by hardware (dedicated circuits).

Furthermore, information that can be accepted by the accepting unit 130 or the terminal accepting unit 630 may be input by any part such as a numeric keypad, a keyboard, a mouse, or a menu screen. The accepting unit 130 and the terminal accepting unit 630 may be realized by a device driver for an input part such as a numeric keypad or a keyboard, control software for a menu screen, or the like.

Furthermore, the receiving unit 120 and the terminal receiving unit 620 are typically realized by wireless or wired communication parts, but may also be realized by broadcast receiving parts.

Furthermore, the transmitting unit 170 and the terminal transmitting unit 670 are typically realized by wireless or wired communication parts, for example, but may also be realized by broadcasting parts.

Figure 4:
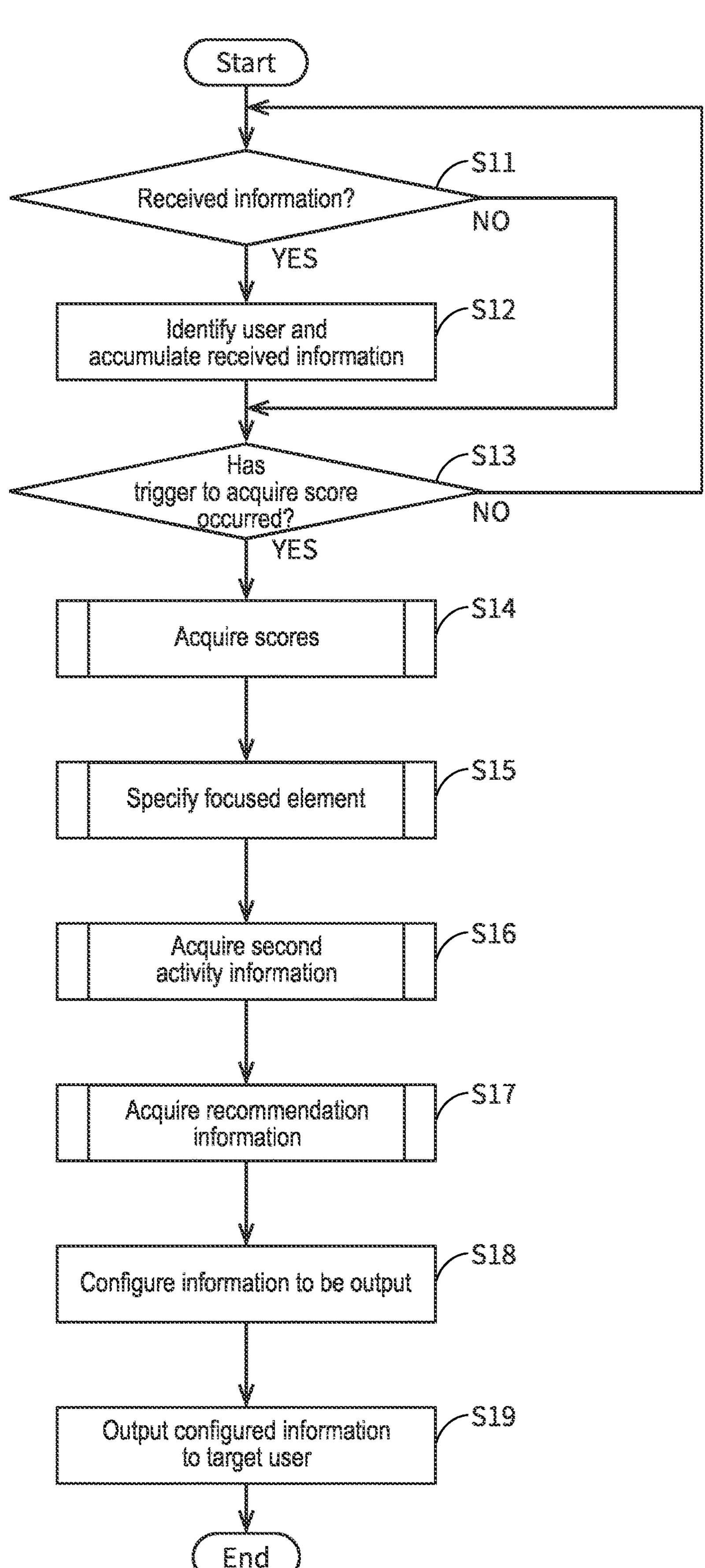
FIG. 4 is a flowchart showing an example of an operation of the information processing apparatus in the embodiment.

FIG. 4 is a flowchart showing an example of an operation of the information processing apparatus 100 in the embodiment.

(Step S11) The processing unit 140 determines whether or not information transmitted from the terminal apparatus 600 or the like has been received by the receiving unit 120. If it is determined that the information has been received, the procedure advances to step S12, or otherwise the procedure advances to step S13.

(Step S12) The processing unit 140 identifies the user based on the received information, and accumulates the received information in the user information storage unit 115 in association with a user identifier. For example, when activity information, sound information, device identifying information, or the like is transmitted from the terminal apparatus 600 in association with a user identifier, the processing unit 140 accumulates the received information in the user information storage unit 115 in association with the user identifier.

(Step S13) The processing unit 140 determines whether or not a trigger to acquire a score has occurred. In other words, the processing unit 140 determines whether or not the conditions for starting acquisition of a score have been satisfied. If it is determined that the trigger has occurred, the procedure advances to step S14. Otherwise, the procedure returns to step S11.

For example, the above-mentioned trigger may be a user's instruction to acquire a score through the terminal apparatus 600 (transmission of predetermined information corresponding to the instruction) or the like, but the trigger is not limited to this. For example, the trigger may be fulfillment of various conditions such as arrival of a predetermined time or new receipt of sound information or other activity information.

(Step S14) The processing unit 140 causes the score acquiring unit 149 to perform score acquiring processing. The score acquiring processing will be described later. Through the score acquiring processing, a score and element scores are acquired and accumulated in the user information storage unit 115.

(Step S15) The processing unit 140 causes the focused element specifying unit 152 to perform focused element specifying processing. The focused element specifying processing will be described later. If one or more evaluation elements to be focused on are specified through the focused element specifying processing, information (e.g., flag information) with which that fact can be identified is accumulated in the user information storage unit 115.

(Step S16) The processing unit 140 causes the second activity information acquiring unit 153 to perform processing for acquiring second activity information. The processing for acquiring second activity information will be described later. Through the processing for acquiring second activity information, second activity information is acquired and accumulated in the user information storage unit 115.

(Step S17) The processing unit 140 causes the recommendation information acquiring unit 157 to perform recommendation information acquiring processing. The recommendation information acquiring processing will be described later. Through the recommendation information acquiring processing, recommendation information is acquired and accumulated in the user information storage unit 115.

(Step S18) The processing unit 140 causes the output unit 161 to configure information that is to be output, using the acquired score or the like and the recommendation information. In this embodiment, information for showing a radar chart using the score, the recommendation information, and the element scores is configured, but there is no limitation to this. The output unit 161 may be configured to configure and output information indicating the element scores as a graph in other formats, or configured not to output information regarding the element scores.

Figure 5:
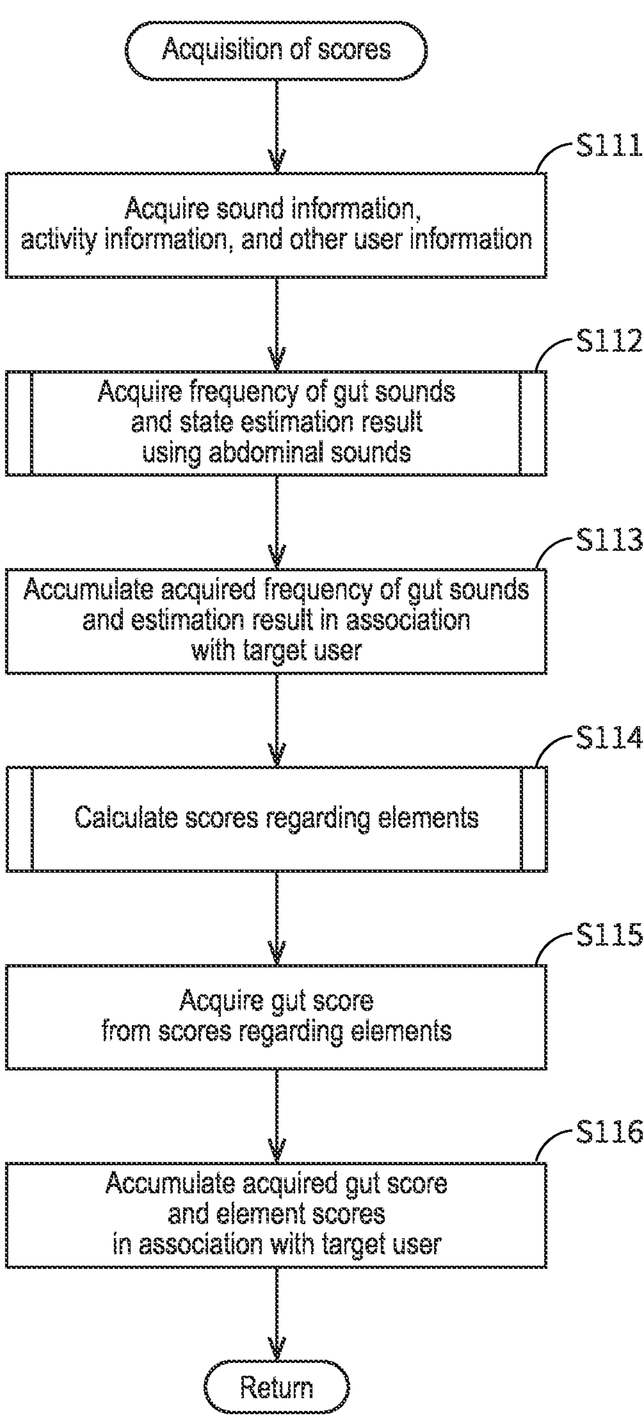
FIG. 5 is a flowchart showing an example of score acquiring processing of the information processing apparatus in the embodiment.

(Step S19) The processing unit 140 causes the output unit 161 to output the configured information to the target user. That is to say, the processing unit 140 causes the transmitting unit 170 to output the information configured by the output unit 161, to the terminal apparatus 600 that is used by the user whose scores are to be calculated. Accordingly, the terminal apparatus 600 that received the information can perform display regarding the score and the recommendation information, FIG. 5 is a flowchart showing an example of the score acquiring processing of the information processing apparatus 100 in the embodiment.

(Step S111) The score acquiring unit 149 acquires sound information, activity information, past user information, and the like regarding a target user from the user information storage unit 115 based on the user identifier of the user. The score acquiring unit 149 may acquire health state information.

(Step S112) The score acquiring unit 149 performs processing for acquiring the frequency of gut sounds and a gut state estimation result using the sound information. Hereinafter, this processing may be referred to as abdominal sound usage processing. The abdominal sound usage processing will be described later in detail.

(Step S113) The score acquiring unit 149 accumulates information such as the acquired frequency of gut sounds and gut state estimation result, in the user information storage unit 115 in association with the user identifier of the target user.

(Step S114) The score acquiring unit 149 causes the element score acquiring unit 151 to perform processing for acquiring a score regarding each element. Hereinafter, this processing may be referred to as element score acquiring processing. In this embodiment, gut-related score acquiring processing, excretion score acquiring processing, food score acquiring processing, drink score acquiring processing, and activity status score acquiring processing are performed as the element score acquiring processing. Each element score acquiring processing will be described later in detail.

(Step S116) When the element scores are obtained, the score acquiring unit 149 acquires a score from the element scores. At this time, the score acquiring unit 149 acquires a score using a predetermined method such as addition or multiplication of the element scores as described above, for example, but there is no limitation to this.

(Step S116) The score acquiring unit 149 accumulates the acquired score and element scores in the user information storage unit 115 in association with the user identifier of the target user. Subsequently, the procedure returns to the processing in FIG. 4.

Figure 6:
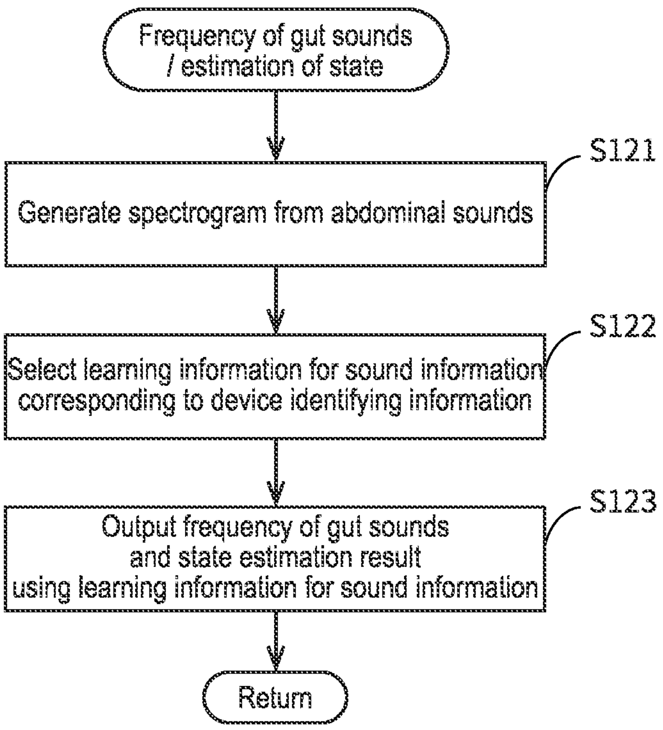
FIG. 6 is a flowchart showing an example of abdominal sounds usage processing of the information processing apparatus in the embodiment.

FIG. 6 is a flowchart showing an example of the abdominal sound usage processing of the information processing apparatus 100 in the embodiment.

(Step S121) The score acquiring unit 149 generates a spectrogram from sound information, which is sound data obtained by recording abdominal sounds.

(Step S122) The score acquiring unit 149 selects, as learning information for sound information that is to be used, learning information for sound information corresponding to the device identifying information corresponding to the sound information, out of the learning information for sound information stored in the learning information storage unit 111.

(Step S123) The score acquiring unit 149 inputs the sound information to the learning information for sound information, and outputs an output indicator value. In this embodiment, the frequency of gut sounds contained in the abdominal sounds and a gut state estimation result are output. Subsequently, the procedure returns to the processing shown in FIG. 5.

In a case in which the sound information stored in the user information storage unit 115 is a spectrogram such as a case in which the sound information transmitted from the terminal apparatus 600 is a spectrogram, the processing in step S121 may not be performed.

Figure 7:
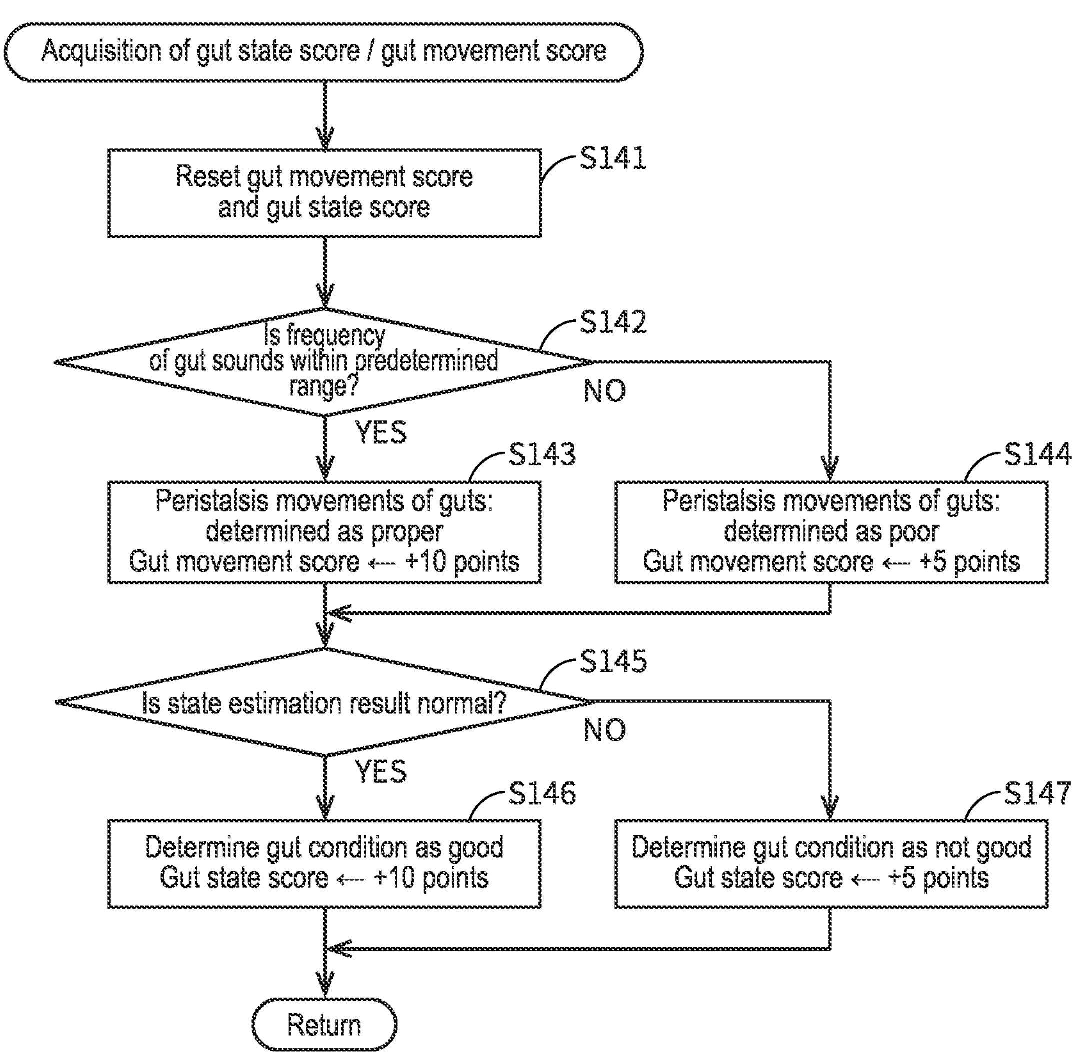
FIG. 7 is a flowchart showing an example of gut-related score acquiring processing of the information processing apparatus in the embodiment.

FIG. 7 is a flowchart showing an example of the gut-related score acquiring processing of the information processing apparatus 100 in the embodiment.

(Step S140 The gut-related score acquiring unit 1511 resets the gut movement score and the gut state score respectively to initial values (e.g., zero).

(Step S142) The gut-related score acquiring unit 1511 determines whether or not the frequency of gut sounds is within a predetermined range. If it is determined that the frequency is within the predetermined range, the procedure advances to step S143, or otherwise the procedure advances to step S144.

The state in which the frequency of gut sounds is within a predetermined range can be set to a state in which the number of gut sounds greater than a predetermined level during a predetermined length of time is or more and less than 20, for example, but the number and the like are not limited to this.

(Step S143) The gut-related score acquiring unit 1611 adds 10 points to the gut movement score. That is to say, the gut-related score acquiring unit 1511 determines that the peristalsis movements of the guts are in a proper state. The procedure advances to step S145.

(Step S144) The gut-related score acquiring unit 1511 adds 5 points to the gut movement score. That is to say, the gut-related score acquiring unit 1511 determines that the peristalsis movements of the guts are in a poor state. The procedure advances to step S145.

(Step S145) The gut-related score acquiring unit 1511 determines whether or not the gut state estimation result is "normal". If it is determined as being within a predetermined range, the procedure advances to step S143, or otherwise the procedure advances to step S144. If the gut state estimation result is "diarrhea" or "constipation", the procedure advances to step S147.

(Step S146) The gut-related score acquiring unit 1511 adds 10 points to the gut state score. That is to say, the gut-related score acquiring unit 1511 determines that the gut condition is in a good state.

(Step S147) The gut-related score acquiring unit 1511 adds 5 points to the gut state score. That is to say, the gut-related score acquiring unit 1511 determines that the peristalsis movements of the guts are in a proper state.

When step S146 or step S147 is ended, the gut-related score acquiring unit 1511 acquires a gut movement score and a gut state score as a result of the above-described processing, and the procedure returns to FIG. 5.

Figure 8:
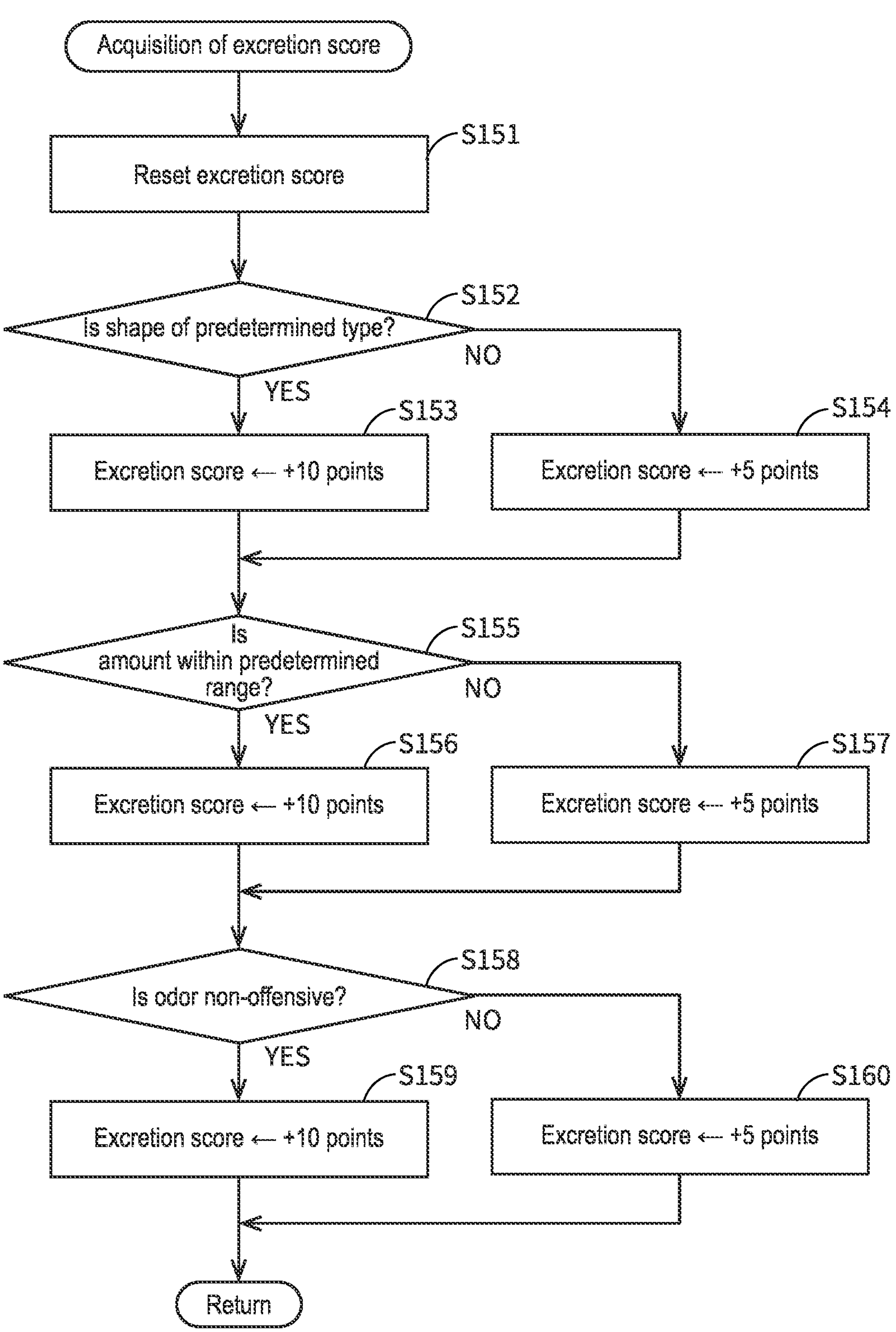
FIG. 8 is a flowchart showing an example of excretion core acquiring processing of the information processing apparatus in the embodiment.

FIG. 8 is a flowchart showing an example of the excretion score acquiring processing of the information processing apparatus 100 in the embodiment.

(Step S151) The excretion score acquiring unit 1512 resets the excretion score to an initial value (e.g., zero).

(Step S152) The excretion score acquiring unit 1512 determines whether or not the shape of excrement corresponds to a predetermined type. For example, if the label value of the Bristol Scale contained in the excretion related information is a predetermined value (e.g., a predetermined word such as "banana" or "sausage"), it can be determined that the shape of excrement corresponds to a predetermined type. If it is determined that the shape of excrement corresponds to the predetermined type, the procedure advances to step S153, or otherwise the procedure advances to step S154.

(Step S153) The excretion score acquiring unit 1512 adds 10 points to the excretion score. The procedure advances to step S155.

(Step S154) The excretion score acquiring unit 1512 adds 5 points to the excretion score. The procedure advances to step S155.

(Step S155) The excretion score acquiring unit 1512 determines whether or not the amount of excrement is within a predetermined range. For example, the user's input value contained in the excretion-related information and indicating the amount of excrement can be used as the amount of excrement. For example, the predetermined range can be set to, but is not limited to, a range from 0 to 200 grams. If it is determined that the amount of excrement is within the predetermined range, the procedure advances to step S156, or otherwise the procedure advances to step S157.

(Step S156) The excretion score acquiring unit 1512 adds 10 points to the excretion score. The procedure advances to step S158.

(Step S157) The excretion score acquiring unit 1512 adds 5 points to the excretion score. The procedure advances to step S158.

(Step S158) The excretion score acquiring unit 1512 determines whether or not the odor of excrement is non-offensive. For example, the user's input value contained in the excretion-related information and indicating the odor of excrement can be used as the odor of excrement. If it is determined that the odor of excrement is non-offensive, the procedure advances to step S159, or otherwise the procedure advances to step S160.

(Step S159) The excretion score acquiring unit 1512 adds 10 points to the excretion score.

(Step S160) The excretion score acquiring unit 1512 adds 5 points to the excretion score.

When step S159 or step S160 is ended, the excretion score acquiring unit 1512 acquires an excretion score as a result of the above-described processing, and the procedure returns to FIG. 5.

Figure 9:
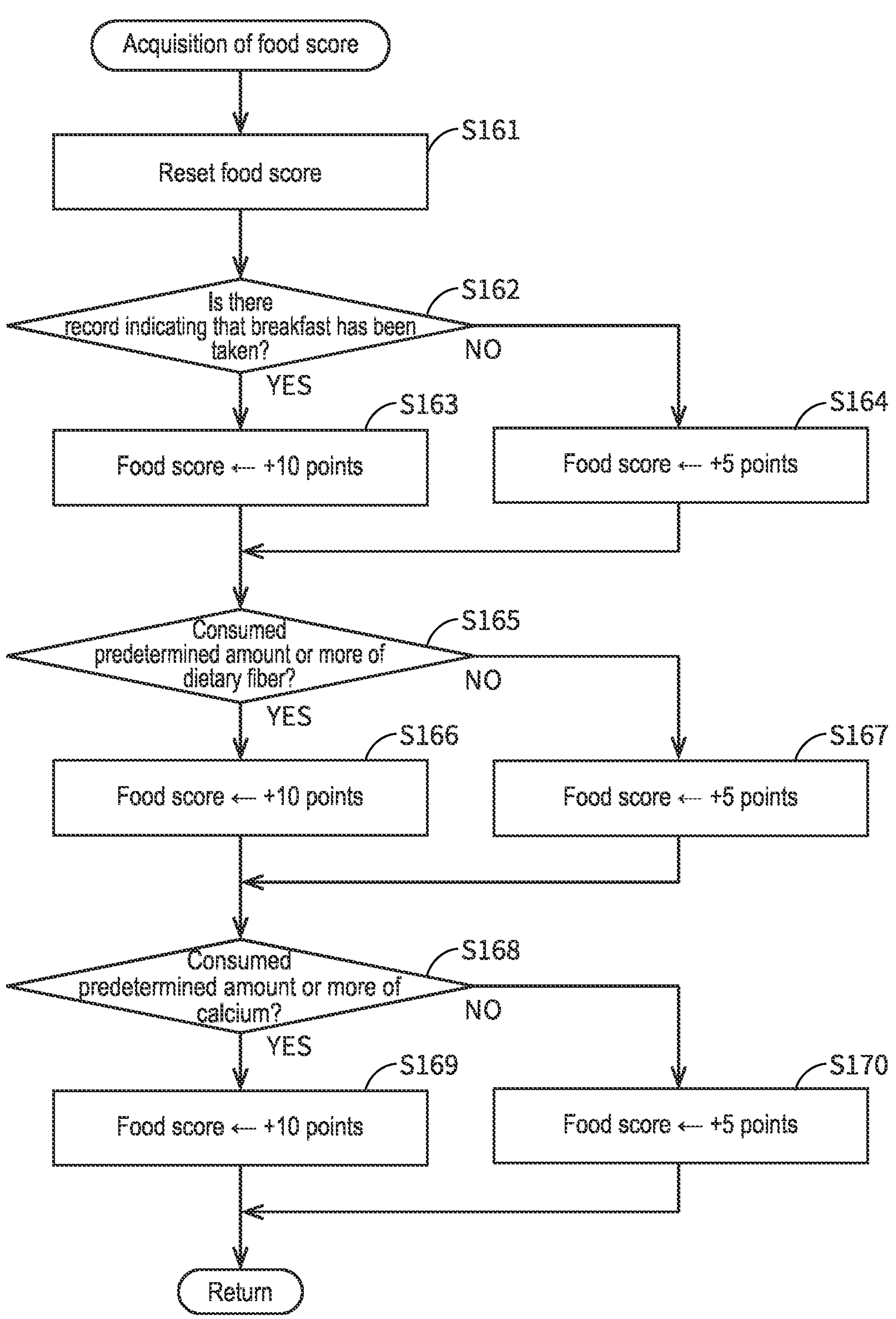
FIG. 9 is a flowchart showing an example of food score acquiring processing of the information processing apparatus in the embodiment.

FIG. 9 is a flowchart showing an example of the food score acquiring processing of the information processing apparatus 100 in the embodiment.

(Step S161) The eating-and-drinking score acquiring unit 1613 resets the food score to an initial value (e.g., zero).

(Step S162) The eating-and-drinking score acquiring unit 1513 determines whether or not the user has taken the breakfast. For example, this determination can be made based on whether or not there is an input value contained in the food information and indicating that the user has taken the breakfast, or the like. If it is determined that the user has taken the breakfast, the procedure advances to step S163, or otherwise the procedure advances to step S164.

(Step S163) The eating-and-drinking score acquiring unit 1513 adds points to the food score. The procedure advances to step S165.

(Step S164) The eating-and-drinking score acquiring unit 1513 adds 5 points to the food score. The procedure advances to step S165.

(Step S165) The eating-and-drinking score acquiring unit 1513 determines whether or not the user has consumed a predetermined amount or more of dietary fiber. For example, this determination can be made using a value obtained by calculating the dietary fiber equivalent based on information contained in the food information and indicating the content of a meal. For example, the predetermined amount can be set to, but is not limited to, 12 grams. An upper limit may be set. If it is determined that the user has consumed the predetermined amount or more of dietary fiber, the procedure advances to step S166, or otherwise the procedure advances to step S167.

(Step S166) The eating-and-drinking score acquiring unit 1613 adds points to the food score. The procedure advances to step S168.

(Step S167) The eating-and-drinking score acquiring unit 1513 adds 5 points to the food score. The procedure advances to step S168.

(Step S168) The eating-and-drinking score acquiring unit 1513 determines whether or not the user has consumed a predetermined amount or more of calcium. For example, this determination can be made using a value obtained by calculating the calcium equivalent based on information contained in the food information and indicating the content of a meal. For example, the predetermined amount can be set to, but is not limited to, 160 milligrams. An upper limit may be set. If it is determined that the user has consumed the predetermined amount or more of calcium, the procedure advances to step S169, or otherwise the procedure advances to step S160.

(Step S169) The eating-and-drinking score acquiring unit 1513 adds points to the food score.

(Step S170) The eating-and-drinking score acquiring unit 1513 adds 5 points to the food score.

When step S169 or step S170 is ended, the eating-and-drinking score acquiring unit 1513 acquires a food score as a result of the above-described processing, and the procedure returns to FIG. 5.

Figure 10:
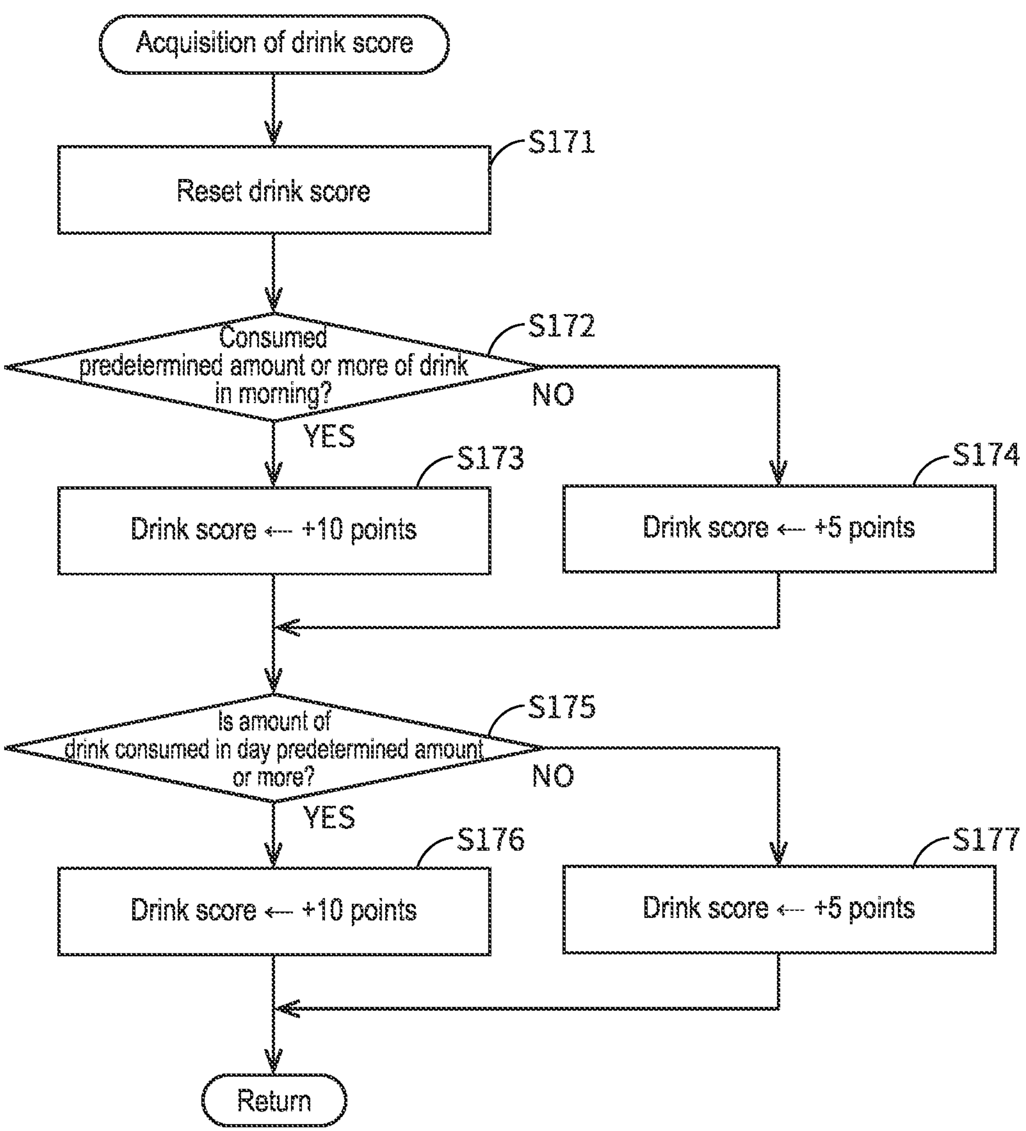
FIG. 10 is a flowchart showing an example of drink score acquiring processing of the information processing apparatus in the embodiment.

FIG. 10 is a flowchart showing an example of the drink score acquiring processing of the information processing apparatus 100 in the embodiment.

(Step S171) The eating-and-drinking score acquiring unit 1513 resets the drink score to an initial value (e.g., zero).

(Step S172) The eating-and-drinking score acquiring unit 1513 determines whether or not the user has consumed a predetermined amount or more of drink in the morning. For example, this determination can be made based on an input value contained in the drink information and indicating the amount of water consumed by the user during a predetermined timeframe or the like. For example, the predetermined amount can be set to, but is not limited to, 300 milliliters. An upper limit may be set. If it is determined that the user has consumed the predetermined amount or more of drink in the morning, the procedure advances to step S173, or otherwise the procedure advances to step S174.

(Step S173) The eating-and-drinking score acquiring unit 1513 adds points to the drink score. The procedure advances to step S175.

(Step S174) The eating-and-drinking score acquiring unit 1513 adds 5 points to the drink score. The procedure advances to step S175.

(Step S175) The eating-and-drinking score acquiring unit 1513 determines whether or not the amount of drink consumed by the user in a day is a predetermined amount or more. For example, this determination can be made based on an input value contained in the drink information and indicating the amount of water consumed by the user in a day or the like. For example, the predetermined amount can be set to, but is not limited to, 2000 milliliters. An upper limit may be set. If it is determined that the amount of drink consumed in a day is the predetermined amount or more, the procedure advances to step S176, or otherwise the procedure advances to step S177.

(Step S176) The eating-and-drinking score acquiring unit 1513 adds points to the drink score.

(Step S177) The eating-and-drinking score acquiring unit 1513 adds 5 points to the drink score.

When step S176 or step S177 is ended, the eating-and-drinking score acquiring unit 1513 acquires a drink score as a result of the above-described processing, and the procedure returns to FIG. 5.

Figure 11:
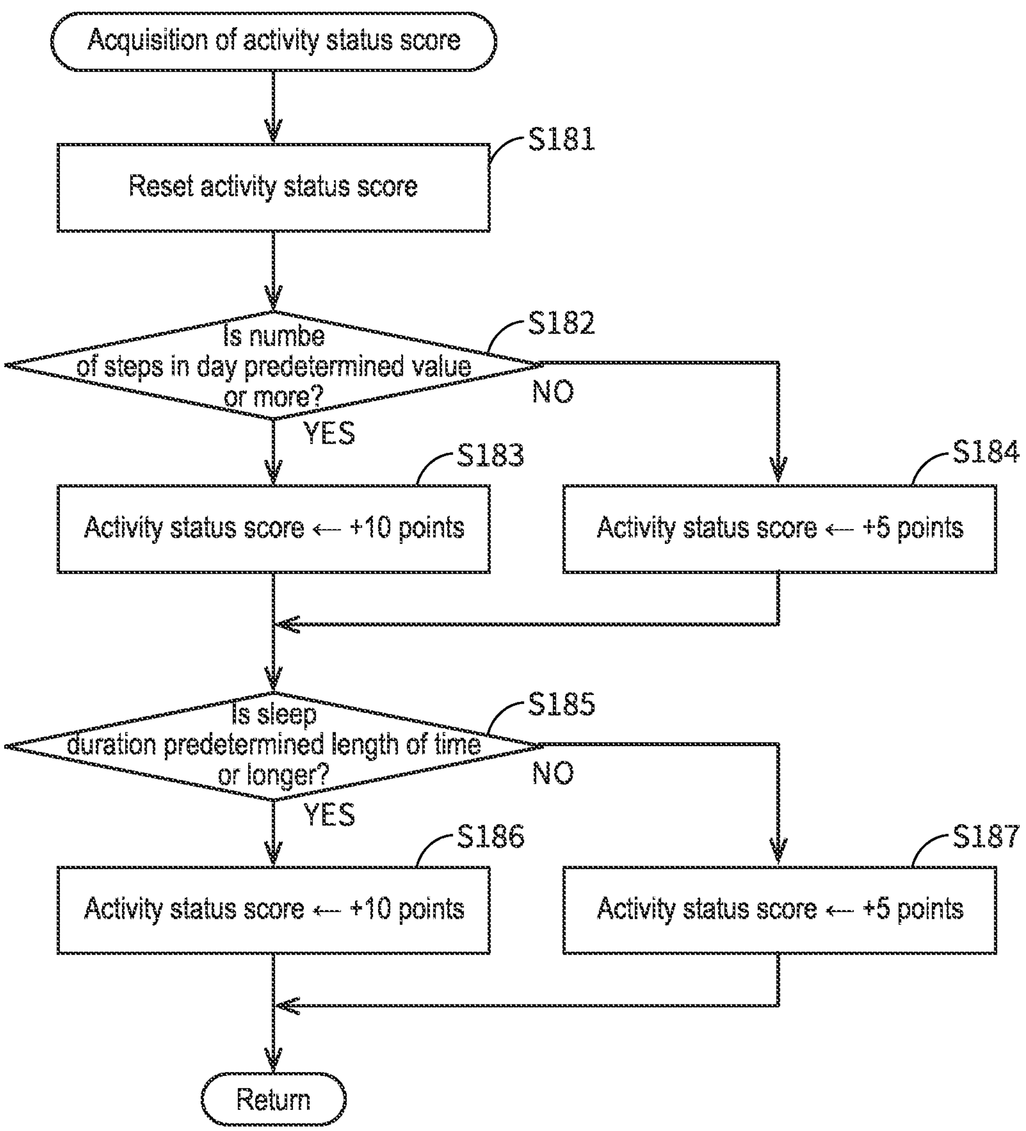
FIG. 11 is a flowchart showing an example of activity status score acquiring processing of the information processing apparatus in the embodiment.

FIG. 11 is a flowchart showing an example of the activity status score acquiring processing of the information processing apparatus 100 in the embodiment.

(Step S181) The activity status score acquiring unit 1514 resets the activity status score to an initial value (e.g., zero).

(Step S182) The activity status score acquiring unit 1514 determines whether or not the number of steps in a day is a predetermined value or more. For example, this determination can be made based on an accumulated value contained in the activity status information and indicating the number of steps taken by the user in a day or the like. For example, the predetermined value can be set to, but is not limited to, 7000 steps. An upper limit may be set. If it is determined that the number of steps in a day is the predetermined value or more, the procedure advances to step S183, or otherwise the procedure advances to step S184.

(Step S183) The activity status score acquiring unit 1514 adds 10 points to the activity status score. The procedure advances to step S185.

(Step S184) The activity status score acquiring unit 1514 adds 5 points to the activity status score. The procedure advances to step S185.

(Step S185) The activity status score acquiring unit 1614 determines whether or not the user's sleep duration is a predetermined length of time or longer. For example, this determination can be made based on an input value contained in the activity status information and indicating the user's sleep duration or the like. For example, the predetermined length of time can be set to, but is not limited to, 7 hours. An upper limit may be set. If it is determined that the sleep duration is the predetermined length of time or longer, the procedure advances to step S186, or otherwise the procedure advances to step S187.

(Step S186) The activity status score acquiring unit 1514 adds 10 points to the activity status score.

(Step S187) The activity status score acquiring unit 1514 adds 5 points to the activity status score.

When step S186 or step S187 is ended, the activity status score acquiring unit 1514 acquires an activity status score as a result of the above-described processing, and the procedure returns to FIG. 5.

Figure 12:
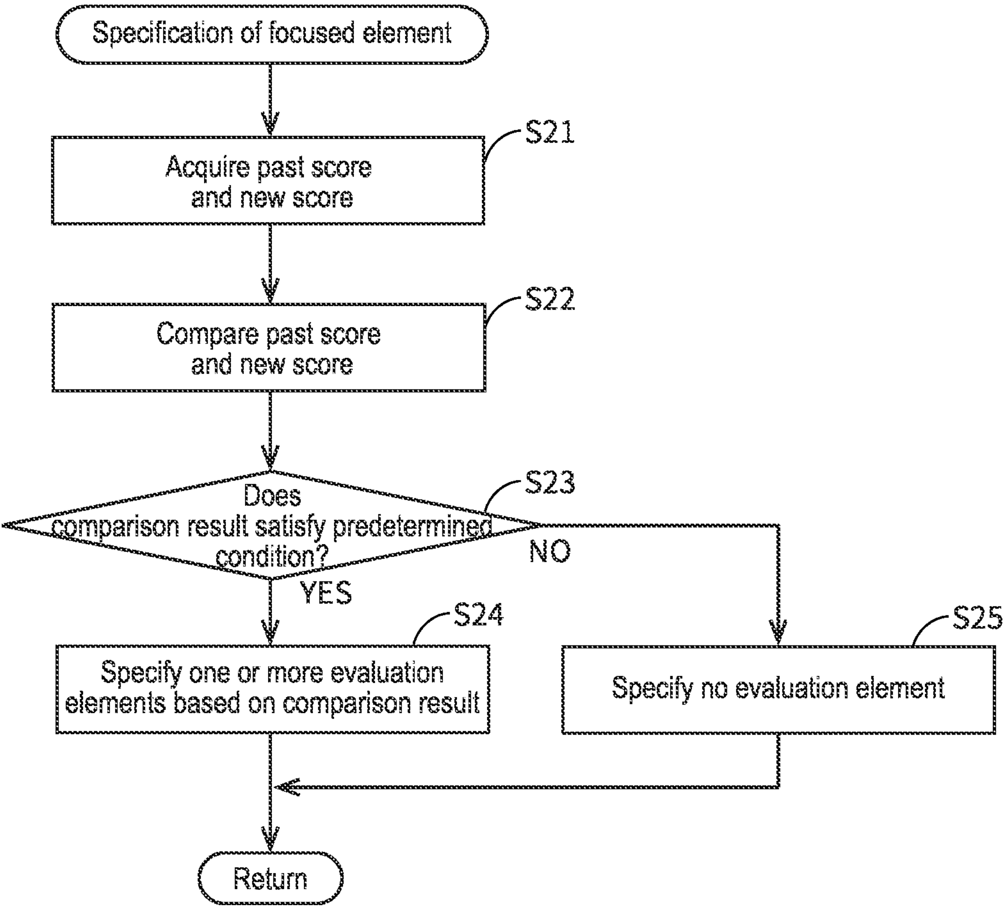
FIG. 12 is a flowchart showing an example of focused element specifying processing of the information processing apparatus in the embodiment.

FIG. 12 is a flowchart showing an example of the focused element specifying processing of the information processing apparatus 100 in the embodiment.

(Step S21) The focused element specifying unit 152 acquires, for a user, a past score stored in the user information storage unit 115 and a new score currently acquired by the score acquiring unit 149.

(Step S22) The focused element specifying unit 152 compares the past score and the new score. In this embodiment, the focused element specifying unit 152 obtains the difference between the focused element scores for the evaluation element specified by the focused element specifying unit 152, for example.

(Step S23) The focused element specifying unit 152 determines whether or not a predetermined condition regarding the result of the comparison between the scores is satisfied. If the predetermined condition is satisfied, the procedure advances to step S24, or otherwise the procedure advances to step S25.

(Step S24) The focused element specifying unit 152 specifies one or more evaluation elements based on the result of the comparison between the scores. In this embodiment, evaluation elements are specified such that a condition regarding the relationship between the size of the difference between the element scores and the predetermined value is satisfied. The focused element specifying unit 152 stores flag information in which an identifier for identifying each specified evaluation element is flagged, in the storage unit 110, for example.

(Step S26) The focused element specifying unit 152 does not specify any evaluation element. In this case, the focused element specifying unit 152 stores flag information indicating that it is determined that there is no specified evaluation element, in the storage unit 110, but there is no limitation to this. If no flag is set for any of the evaluation elements, it can be taken to mean that it has been determined that there is no specified evaluation element.

When step S24 or step S25 is ended, the procedure returns to the processing in FIG. 4.

Figure 13:
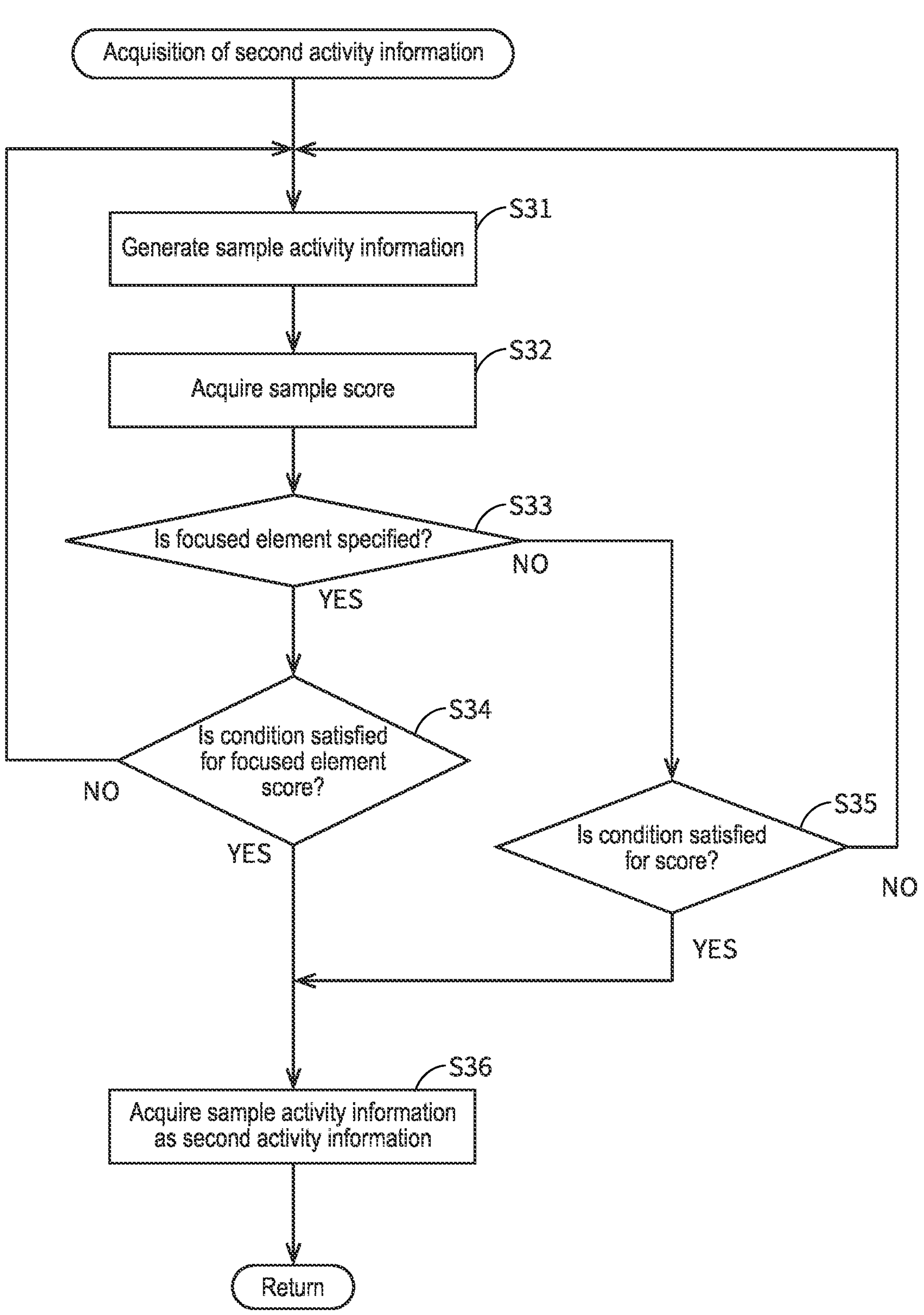
FIG. 13 is a flowchart showing an example of processing for acquiring second activity information, of the information processing apparatus in the embodiment.

FIG. 13 is a flowchart showing an example of the processing for acquiring second activity information, of the information processing apparatus 100 in the embodiment.

(Step S31) The second activity information acquiring unit 153 causes the sample generating unit 154 to generate sample activity information from first activity information.

(Step S32) The second activity information acquiring unit 153 causes the sample score acquiring unit 155 to acquires a sample score.

(Step S33) The second activity information acquiring unit 153 causes the focused element specifying unit 152 to determine whether or not any of the focused elements has been specified. If any of the focused elements has been specified, the procedure advances to step S34, or otherwise the procedure advances to step S3.

(Step S34) The second activity information acquiring unit 153 compares, for the focused element score, the sample score and the score acquired by the score acquiring unit 149, and determines whether or not a condition regarding the relationship between the change in the focused element score and the predetermined value is satisfied. If the condition is satisfied, the procedure advances to step S436, or otherwise the procedure returns to step S31.

(Step S35) The second activity information acquiring unit 153 compares the sample score and the score acquired by the score acquiring unit 149, and determines whether or not, a condition regarding the relationship between the change in the score and the predetermined value is satisfied. If the condition is satisfied, the procedure advances to step S36, or otherwise the procedure returns to step S31.

(Step S36) The second activity information acquiring unit 153 acquires the sample activity information as the second activity information. The second activity information acquiring unit 153 accumulates the acquired second activity information in the user information storage unit 115 in association with a user identifier of the target user, for example. Subsequently, the procedure returns to the processing in FIG. 4.

Figure 14:
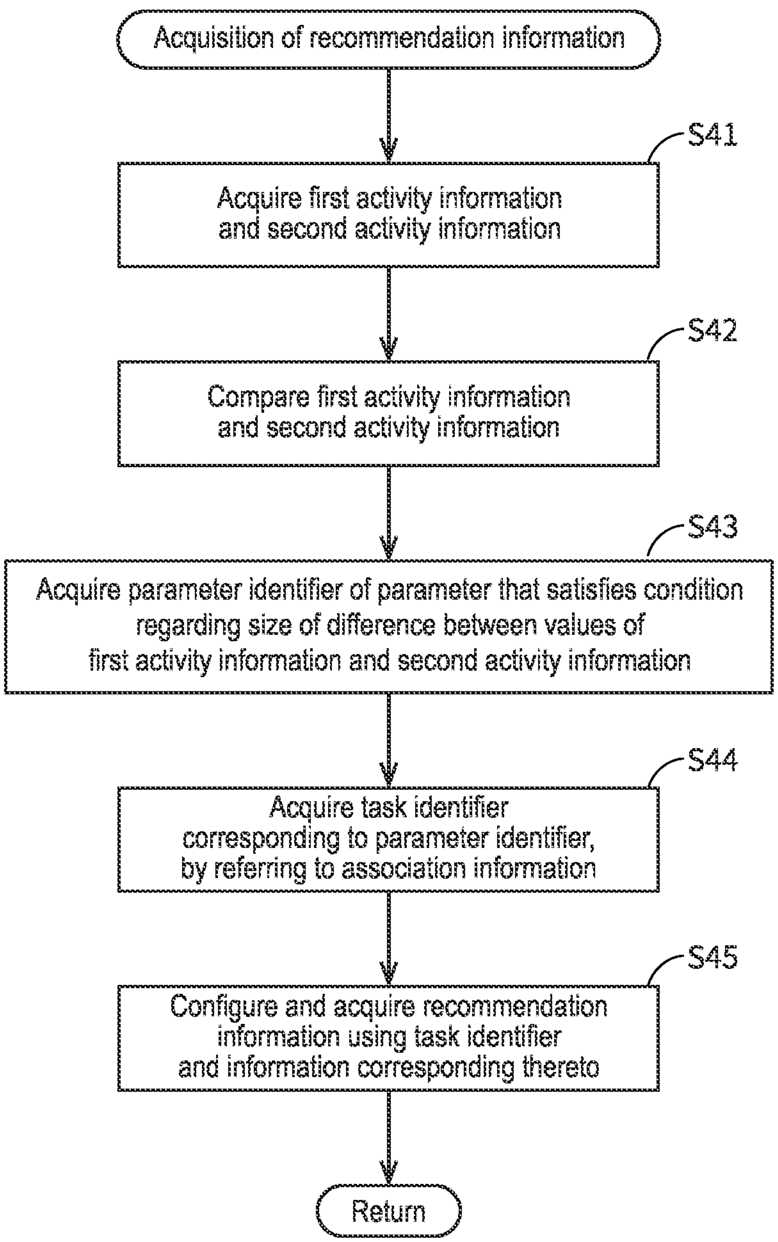
FIG. 14 is a flowchart showing an example of recommendation information acquiring processing of the information processing apparatus in the embodiment.

FIG. 14 is a flowchart showing an example of the recommendation information acquiring processing of the information processing apparatus 100 in the embodiment.

(Step S41) The recommendation information acquiring unit 157 acquires first activity information and second activity information from the user information storage unit 115.

(Step S42) The recommendation information acquiring unit 157 causes the activity information comparing unit 158 to compare the first activity information and the second activity information.

(Step S43) The activity information comparing unit 158 acquires a parameter identifier of a parameter that satisfies a condition regarding the size of the difference between the values of the first activity information and the second activity information.

(Step S44) The recommendation information acquiring unit 157 acquires a task identifier corresponding to the parameter identifier acquired by the activity information comparing unit 158, by referring to the association information stored in the recommendation information storage unit 117.

(Step S45) The recommendation information acquiring unit 157 configures and acquires recommendation information, using the acquired task identifier and information corresponding thereto. The recommendation information acquiring unit 157 accumulates the acquired recommendation information in the user information storage unit 115 in association with a user identifier. Subsequently, the procedure returns to the processing in FIG. 4.

Next, specific examples of an operation of the information processing system 1 in this embodiment will be described with reference to the screen transition of the terminal apparatus 600 that is used by the user.

In the following specific examples, a case is assumed in which the information processing system 1 provides a health support application to assist a user to lead a healthy life. The health support application accepts input operations related to activity information of a user and provides the user with information useful for maintaining good health. The health support application is realized when the user executes a predetermined application on the terminal apparatus 600 and communication is performed between the terminal apparatus 600 and the information processing apparatus 100. The following screen examples of the health support application are displayed by the terminal output unit 660 based on the control by the terminal processing unit 640. When the user gives an instruction to acquire a score by having the functions of the health support application executed, the information processing apparatus 100 outputs information regarding the score and recommendation information. When the terminal apparatuses 600 receives these pieces of output information, the terminal output unit 660 displays a result display screen, for example.

FIG. 15 is a diagram showing an example of association information in a specific example of the embodiment.

It is sufficient that the association information stored in the recommendation information storage unit 117 is as shown in FIG. 15, for example. That is to say, in the association information, a parameter identifier is associated with a task identifier. As shown in the drawing, for example, information corresponding to a task identifier, such as a task name or a task description, may be stored in association with a parameter identifier, for example. The task name or the task description may be used as a task identifier. As shown in the drawing, for example, a product identifier for a product related to the task may be associated with the parameter identifier. Other information on the product related to the task, such as a product name, a product image, or a price, may be stored in association with the parameter identifier, for example. If these various types of information corresponding to the task identifier are output, it is possible to make the user more aware of information regarding the task to be executed and to effectively motivate the user to purchase related products.

Figure 16:
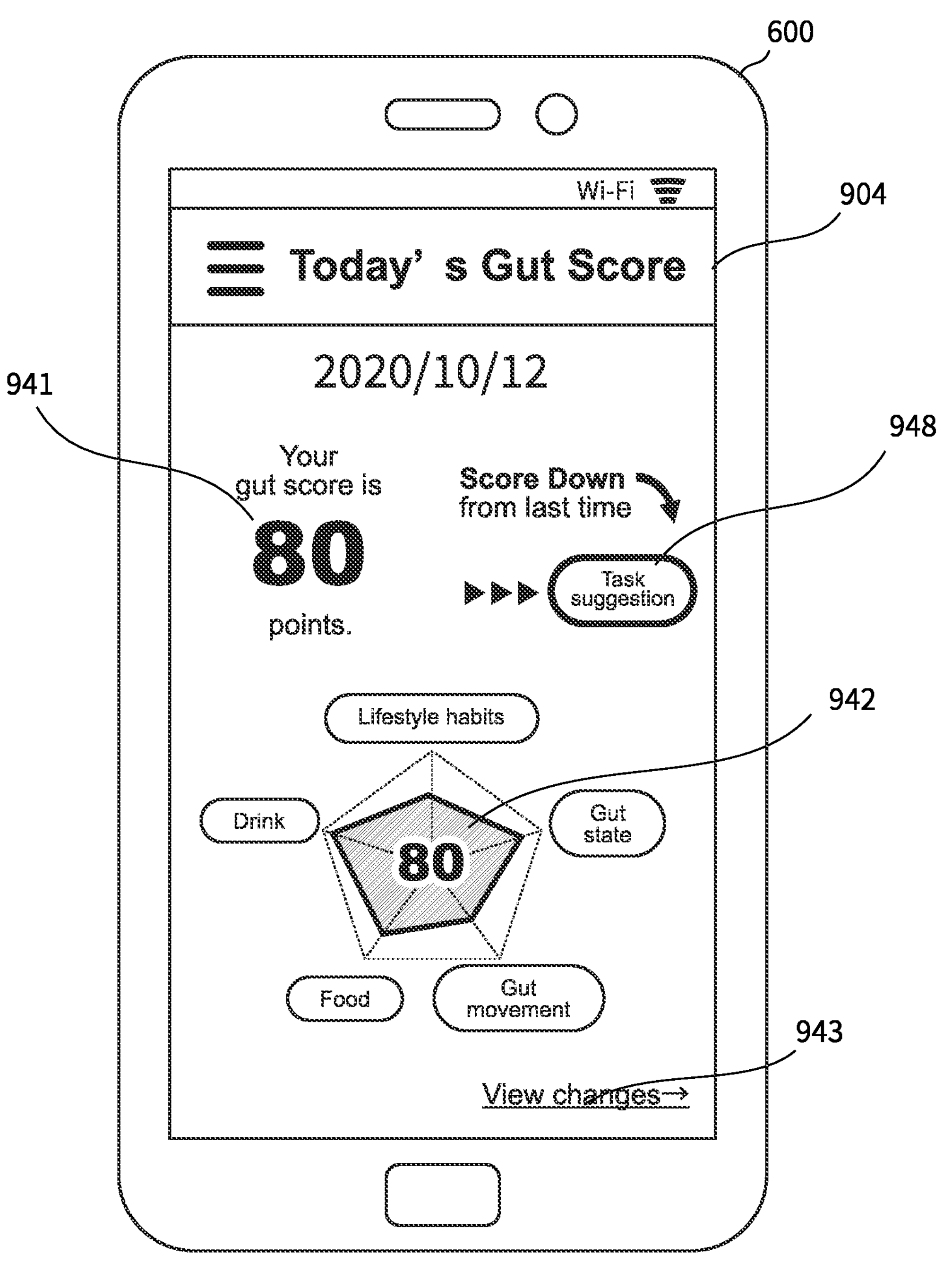
FIG. 16 is a first diagram showing a specific example of a result display screen displayed on the terminal apparatus in the embodiment.
Figure 17:
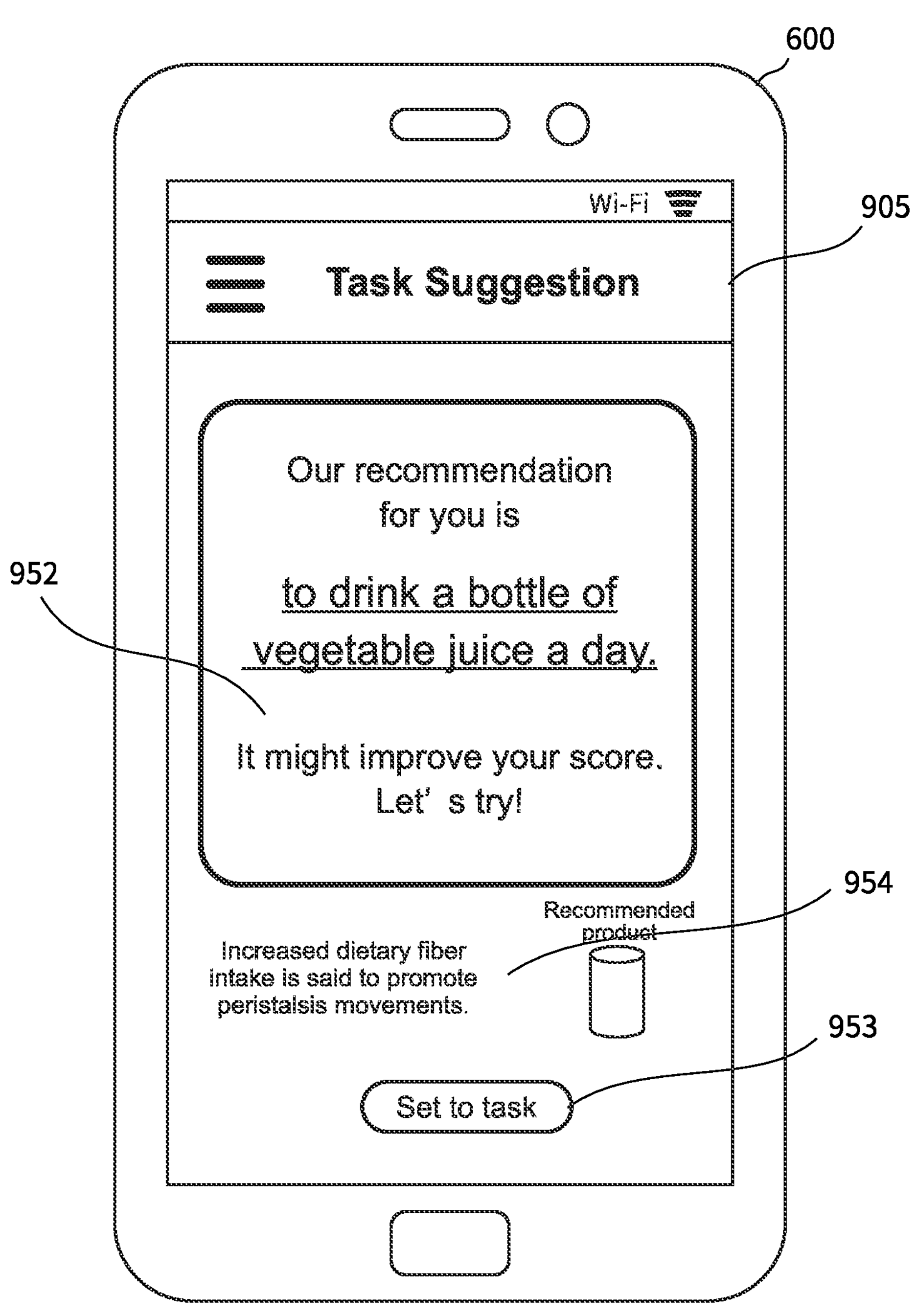
FIG. 17 is a second diagram showing a specific example of a result display screen displayed on the terminal apparatus in the embodiment.

FIG. 16 is a first diagram showing a specific example of a result display screen displayed on the terminal apparatuses 600 in the embodiment. FIG. 17 is a second diagram showing a specific example of a result display screen displayed on the terminal apparatuses 600 in the embodiment.

FIG. 16 shows a score display screen 904, which is one of the result display screens of the health support application. The score display screen 904 includes a gut score display area 941 that displays an acquired score (which may be referred to as a gut score in this specific example) and an element score display area 942 that displays element scores in the form of a radar chart, for example. The user can check the gut score and the element scores on the score display screen 904. Since the element scores are shown in the form of a radar chart, the user can intuitively know which elements may be lacking in efforts with respect to maintaining a high gut condition. In the example shown in FIG. 16, a history display button 943 is included to check the changes including past scores as well. The user can operate the history display button 943 to check changes in the gut score and the element scores.

The score display screen 904 includes a task suggestion button 948 for displaying the recommendation information. The user can display a recommendation screen 905, which is one of the result display screens of the health support application, as shown in FIG. 17 and check the recommendation information by operating the task suggestion button 948. The gut score and recommendation information may be displayed on a single result display screen.

As shown in FIG. 17, the recommendation screen 905 includes a task display area 952 that displays a task corresponding to a task identifier contained in the recommendation information, and a task setting button 953 for accepting operations to set the displayed task as a task to be executed by the user, for example. The user can recognize that the task may effectively contribute to improving his or her health state, by checking the task displayed in the task display area 952. Also, the user can easily set the displayed task as a task to be executed by the user, by operating the task setting button 953. That is to say, if such recommendation information is output to the terminal apparatuses 600 and displayed on the recommendation screen 905, the user can be easily and effectively motivated to effectively improve his or her health state.

In this specific example, the recommendation screen 905 further includes a related information display area 954. The related information display area 964 displays information related to the task contained in the recommendation information. For example, a description of a task or information on a product related to the task displayed in the task display area 952 may be included. Accordingly, it is possible to make the user more aware of information regarding the task to be executed and to effectively motivate the user to purchase related products. The information related to the task may be, but is not limited to, information based on association information, for example.

Figure 18:
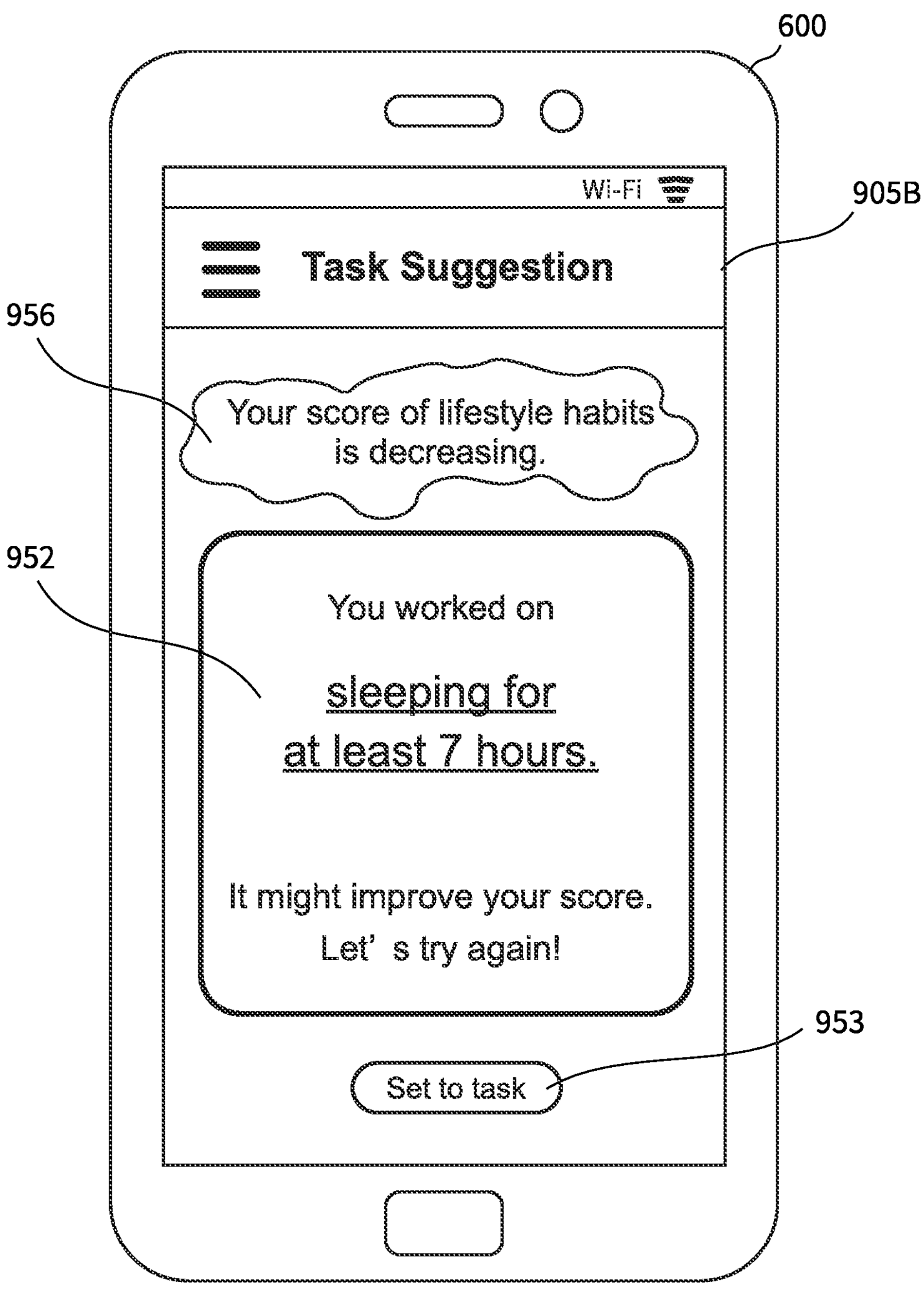
FIG. 18 is a diagram showing a recommendation screen according to a modified example of the specific example in the embodiment.

FIG. 18 is a diagram showing a recommendation screen 905B according to a modified example of the specific example.

The recommendation screen 9058 includes a focused information display area 956 that displays information regarding an evaluation element that the user is required to focus on or a parameter, in addition to the task display area 952 and the task setting button 953. The focused information display area 956 displays an evaluation element specified by the focused element specifying unit 152 or a parameter, for example. If such a display is shown in combination with the task display area 962, the user can determine whether or not to execute a task that may contribute to improvement, based on the recognition of issues regarding a health state. The task can be presented in a way that is more persuasive to the user, and the user can be more strongly motivated to perform the task.

As shown in FIG. 18, if the task display area 952 displays a task previously executed by the user, it is desirable to display the task in such a way that the user can recognize that he or she previously executed the task. This can make the user feel that the hurdle for executing the task is low, and can easily motivate the user to execute the task.

As explained above, it can be said that the information processing apparatus 100 can realize the following information processing method using the learning information and the sound information stored in the storage unit 110. That is to say, the information processing apparatus 100 causes: a learning information acquiring unit to acquire learning information configured using two or more pieces of training data having activity information containing values of two or more parameters regarding an activity state of a user and a score regarding a health state of the user, a first activity information acquiring unit to acquire first activity information containing respective values of the two or more parameters, which are values according to the activity state of the user; a score acquiring unit to acquire a score regarding the health state of the user; a second activity information acquiring unit to acquire, using the learning information, second activity information in which a value of at least one of the two or more parameters is different from that in the first activity information, and in which a score acquired by applying the learning information to the second activity information is different from the score acquired by the score acquiring unit: a recommendation information acquiring unit, to acquire recommendation information regarding at least one of the two or more parameters regarding the activity state of the user, according to a result of a comparison between the first activity information and the second activity information; and an output unit to output the recommendation information acquired by the recommendation information acquiring unit.

According to this embodiment, the information processing apparatus 100 can output information that is regarding an activity state of a user and that will change a score regarding a health state of the user. The user can be encouraged to perform activities based on recognition of the output information, which can contribute to improvement of the health state of the user. Since the health state of the user is scored and processed based on the score, the health state of the user can be evaluated objectively and information can be output. If such processing is performed using activity information containing values of two or more parameters, it is possible to output more accurate information from the viewpoint of contributing to the improvement of the health state of the user compared with a case of simply recommending a task that was performed when the previous score was good based on history information that records the correspondence between past task execution results and scores, for example.

In this embodiment, it is possible to easily obtain, based on the learning information, how a new score that is newly acquired will change (e.g., will be a better score) under what kind of activity states. Thus, it is possible to easily and effectively output information that may contribute to improvement of the health state of the user.

In this embodiment, scores are acquired using information regarding elements that are thought to be related to a gut condition. Thus, a more accurate score can be output. The score can also be output with higher accuracy when the score is acquired using the users health state information. In addition, the score is acquired using information on multiple elements. Thus, a score with even higher accuracy can be output. In this embodiment, multiple element scores are acquired and the score is acquired using them. The multiple element scores are output as a graph such as a radar chart. Thus, the user can intuitively grasp the evaluation results for each element regarding a health state.

The information processing apparatus 100 may be constituted by one server, multiple servers that operate in coordination with each other, or other built-in computers or the like. It will be appreciated that the server may be a so-called cloud server, an ASP server, or the like, and there is no limitation on the type thereof.

The processing in Embodiment 1 may be realized by software. The software may be distributed by software downloads or any other suitable method. Furthermore, the software may be distributed in a form where the software is stored in a recording medium such as a CD-ROM. The software that realizes the information processing apparatus 100 in this embodiment is the following sort of program. Specifically, this program is a program for causing a computer of the information processing apparatus 100 to function as: a learning information acquiring unit that acquires learning information configured using two or more pieces of training data having activity information containing values of two or more parameters regarding an activity state of a user and a score regarding a health state of the user, a first activity information acquiring unit that acquires first activity information containing respective values of the two or more parameters, which are values according to the activity state of the user; a score acquiring unit that acquires a score regarding the health state of the user; a second activity information acquiring unit that acquires, using the learning information, second activity information in which a value of at least one of the two or more parameters is different from that in the first activity information, and in which a score acquired by applying the learning information to the second activity information is different from the score acquired by the score acquiring unit: a recommendation information acquiring unit, that acquires recommendation information regarding at least one of the two or more parameters regarding the activity state of the user, according to a result of a comparison between the first activity information and the second activity information; and an output unit that outputs the recommendation information acquired by the recommendation information acquiring unit.

The terminal apparatuses may each have part or the whole of the configuration for realizing the functions related to the acquisition and output of gut scores as those of the information processing apparatus described above.

In the abdominal sound usage processing, the extraction of the frequency of gut sounds and the estimation of the gut state may be performed using learning information configured using mutually different pieces of input information.

Furthermore, the element scores may be acquired not only through addition of evaluation points to the element score but also subtraction and the like. The element scores may be acquired through addition to or subtraction from a base point, for example. The base point may be a predetermined point or may be set based on past history or other factors. For example, a previously acquired element store may be set as the current base point. Alternatively, a value (e.g., an average value, etc.) obtained through calculation based on information on past element scores in a predetermined period may be set as the base point. If this method is used, for each element score, a determination result for the reference and the degree to which element score is affected thereby can be easily adjusted.

It would be useful if, among several possible activity states that a user can achieve, it is possible to specify one that has a relatively large influence on improving the health state of the user from the current state. That is to say, the user will be more likely to be able to improve his or her health state by engaging in activities while being aware of the specified activity state. However, it has been conventionally difficult to know what kind of activity state of a user affects the health state of the user.

As described above, the information processing apparatus according to Embodiment 1 makes it possible to output information regarding a user's activity state that may affect, a score regarding the health, thus rendering this apparatus useful as an information processing apparatus and the like.

Aspects

It will be understood by those skilled in the art that Embodiment 1 given above as an example is a specific example of the following aspects.

A first aspect is directed to an information processing apparatus including: a learning information acquiring unit that acquires learning information configured using two or more pieces of training data having activity information containing values of two or more parameters regarding an activity state of a user and a score regarding a health state of the user; a first activity information acquiring unit that acquires first activity information containing respective values of the two or more parameters, which are values according to the activity state of the user; a score acquiring unit that acquires a score regarding the health state of the user; a second activity information acquiring unit that acquires, using the learning information, second activity information in which a value of at least one of the two or more parameters is different from that in the first activity information, and in which a score acquired by applying the learning information to the second activity information is different from the score acquired by the score acquiring unit: a recommendation information acquiring unit that acquires recommendation information regarding at least one of the two or more parameters regarding the activity state of the user, according to a result of a comparison between the first activity information and the second activity information; and an output unit that outputs the recommendation information acquired by the recommendation information acquiring unit.

By utilizing this configuration, it is possible to output information regarding a user's activity state that may affect a score regarding the health.

Furthermore, a second aspect of the present invention is directed to the information processing apparatus according to the first aspect, wherein the score acquiring unit acquires health state information regarding the health state of the user, and acquires a score regarding the health state of the user from the acquired health state information.

By utilizing this configuration, it is possible to use a score using health state information regarding the health state of the user.

Furthermore, a third aspect of the present, invention is directed to the information processing apparatus according to the second aspect, wherein the score acquiring unit acquires a score regarding the health state of the user, using the acquired health state information and first activity information acquired from the first activity information acquiring unit.

By utilizing this configuration, it is possible to use a score reflecting the health state information and the first activity information.

Furthermore, a fourth aspect of the present invention is directed to the information processing apparatus according to any one of the first to third aspects, wherein the second activity information acquiring unit acquires second activity information in which a score acquired by applying the learning information thereto is higher than the score acquired by the score acquiring unit.

By utilizing this configuration, it is possible to output information regarding a uses activity state that can result in a higher score regarding the health.

Furthermore, a fifth aspect of the present invention is directed to the information processing apparatus according to the fourth aspect, wherein the second activity information acquiring unit acquires two or more pieces of second activity information that are different from each other, and the recommendation information acquiring unit outputs, using the first activity information and the two or more pieces of second activity information, recommendation information containing information regarding an order of significance of an influence given on the score by at least two parameters of the two or more parameters regarding the activity state of the user.

By utilizing this configuration, it is possible to output information regarding an order of significance of an influence given on the score by two or more parameters.

Furthermore, a sixth aspect of the present invention is directed to the information processing apparatus according to any one of the first to fifth aspects, wherein the learning information acquiring unit acquires learning information configured for the user, using training data having activity information of the user corresponding to the score acquired by the score acquiring unit and the score.

By utilizing this configuration, it is possible to output highly accurate information regarding a user's activity state that may affect a score regarding the health, for each user.

Furthermore, a seventh aspect of the present invention is directed to the information processing apparatus according to any one of the first to sixth aspects, wherein the score acquiring unit acquires the score based on sound information from abdominal sounds of the user.

By utilizing this configuration, it is possible to output information regarding a user's activity state that may affect a score based on sound information from abdominal sounds of the user.

Furthermore, an eighth aspect of the present invention is directed to the information processing apparatus according to the seventh aspect, further including: a sound information acquiring unit that acquires sound information from abdominal sounds of a user, wherein the score acquiring unit acquires learning information for sound information configured using two or more pieces of training data having input information containing the sound information and output information regarding a predetermined output indicator regarding an activity state of guts, and acquires the score based on output information acquired by applying the learning information for sound information to input information containing the sound information acquired by the sound information acquiring unit.

By utilizing this configuration, it is possible to output information regarding a user's activity state that may affect a score reflecting an activity state of the guts of the user.

Furthermore, a ninth aspect of the present invention is directed to the information processing apparatus according to the eighth aspect, further including: a microphone for recording abdominal sounds of a user; and a display unit capable of displaying information, wherein the sound information acquiring unit acquires sound information from the abdominal sounds recorded by the microphone, and the output unit displays the recommendation information on the display unit.

By utilizing this configuration, it is possible for the user to check the recommendation information displayed based on the abdominal sounds recorded using the microphone.

Furthermore, a tenth aspect of the present invention is directed to the information processing apparatus according to any one of the first to ninth aspects, wherein the score is constituted by element scores respectively for two or more evaluation elements regarding the health state of the user, the score acquiring unit is configured to be capable of acquiring the score by acquiring the element scores, and at least one of the two or more element scores is any one of an excretion score regarding excretion by the user, a food score regarding food consumed by the user, a drink score regarding drink consumed by the user, an activity status score regarding an activity status of the user, and a gut-related score regarding an activity state of guts of the user.

By utilizing this configuration, it is possible to output information regarding a users activity state that may affect a score constituted by respective element scores of multiple evaluation elements.

Furthermore, an eleventh aspect of the present invention is directed to the information processing apparatus according to the tenth aspect, further including: a focused element specifying unit that specifies one or more evaluation elements focused out of the two or more evaluation elements according to a determination result as to whether or not a result of a comparison between a past score and a new score acquired for one user satisfies a predetermined condition, wherein the second activity information acquiring unit acquires second activity information in which a focused element score that is regarding the evaluation element specified by the focused element specifying unit and that constitutes a score acquired by applying the learning information to the second activity information is different from the focused element score that constitutes the score acquired by the score acquiring unit.

By utilizing this configuration, it is possible to output information regarding a user's activity state corresponding to the evaluation element focused on in the comparison between the past score and the new score.

Furthermore, a twelfth aspect of the present invention is directed to the information processing apparatus according to any one of the first to eleventh aspects, wherein at least one of the two or more parameters is any one of drink consumption regarding consumption of drink, food consumption regarding consumption of food, lifestyle habits regarding activities other than eating and drinking, and exercise information regarding exercise.

By utilizing this configuration, it is possible to output recommendation information regarding any one of food consumption, drink consumption, lifestyle habits, and exercise information.

Embodiment 2

In Embodiment 2, an information processing apparatus is configured to select one or more tasks using input information containing sound information regarding living body sounds of a user and learning information prepared in advance, and output information regarding the selected tasks. In this embodiment, abdominal sounds are used as the living body sounds. Hereinafter, an information processing system 2001 having an information processing apparatus 2100 configured in this way will be described.

The terms used in Embodiment 2 are generally defined as follows. The meanings of these terms do not always have to be interpreted as indicated herein, and have to be interpreted in light of individual explanations in Embodiment 2, if any, for example.

The living body sounds refer to sounds emanating from a living body of a user. Examples of the living body sounds include abdominal sounds, heart sounds, breathing sounds, neck sounds, leg sounds, joint sounds, tinnitus sounds, and swallowing sounds. The abdominal sounds refer to sounds emanating from the abdomen of a user. The abdominal sounds may include gut sounds emanating from the intestines, for example. The abdominal sounds may include sounds emanating due to blood flow in the abdomen (e.g., abdominal aortic sounds) and sounds emanating from organs such as the stomach. The heart sounds refer to sounds produced by the beating heart. The breathing sounds refer to sounds produced by the lungs when breathing. The neck sounds refer to sounds emanating from the neck. The leg sounds refer to sounds produced when blood flows in the legs. The joint sounds refer to sounds emanating from the joints. The tinnitus sounds refer to sounds produced when blood flows in the ear. The swallowing sounds refer to sounds swallowing sounds produced when food and drink flow from the pharyngeal region into the esophagus, sounds emanating from the carotid aorta, or the like.

The sound information refers to information obtained based on living body sounds. The sound information may be the recorded living body sound data itself, or data obtained by processing or editing the data.

The life information is information regarding the user's life state. The life state includes various elements such as those regarding the user's behavior, state, and the like. In the following embodiment, the life information includes excretion-related information, eating-and-drinking information, and activity status information, for example. That is to say, the life state includes the user's excretion status, the user's eating-and-drinking status, and the user's activity status, for example. Note that the life information is not limited to this, and may include information regarding other elements or information regarding only some of these elements. The information on each element of the life information (excretion-related information, eating-and-drinking information, activity status information, etc.) may include information on detailed elements.

The excretion-related information is information regarding the user's excretion status. The excretion-related information may include values of parameters from various viewpoints such as the time of excretion, amount, odor, and form (shape, color, etc.) of excrement. Mom specifically, for example, in this embodiment, the excretion-related information includes a value indicated by known Bristol Stool Form Scale (alternatively referred to as the "Bristol scale" hereinafter). The Bristol scale indicates the physiological transit time through the gastrointestinal tract and can be said to indirectly express the state of the guts. Labels corresponding to the values expressed by the Bristol scale (e.g., "banana", "sausage", "mushy" etc.) may be used as the excretion-related information. The excretion-related information may be information resulting from the evaluation of excretion by an evaluator such as a user (information involving the subjectivity of the evaluator) or information resulting from measurement or evaluation by an evaluation device or the like.

The eating-and-drinking information is information regarding the user's eating-and-drinking status. As described above, the eating-and-drinking information may include information from various viewpoints such as the amount of water consumed, the amount, of alcohol consumed, and the content of a meal. The eating-and-drinking information may be conceptually divided into food information regarding food and eating habits and drink information regarding drink consumption. More specifically, for example, in this embodiment, the eating-and-drinking information includes, but is not limited to, at least one of information regarding the amount of water consumed, information regarding whether or not alcohol was consumed or the amount of alcohol consumed, information regarding whether or not a meal was taken or the content of a meal, and information regarding whether or not a particular group of food was consumed or the amount thereof consumed. The particular group of food refers to food that belongs to a particular group among the groups classified as meat, dairy products, vegetables, and the like, for example, but the viewpoint and granularity of such "group" classification are not limited to this. One or both of the food information and the drink information may include those related to so-called supplements (health foods). The eating-and-drinking information is, but is not limited to, information that is input by an evaluator such as a user who performed evaluation of the eating-and-drinking status. For example, the eating-and-drinking information may be information resulting from measurement or evaluation by an evaluation device or the like. For example, the types and amounts of food or drink consumed may have different effects on digestive motility.

The activity status information is information regarding the user's activity status. The activity status herein refers to a status related to lifestyle habits (i.e., actions and behaviors that the user repeatedly performs in daily life) excluding the eating-and-drinking status. That is to say, the activity status information may include information regarding lifestyle habits excluding the eating-and-drinking information. In this embodiment, the activity status information includes, but is not limited to, at least one of sleep information regarding sleep (sleep duration, sleep quality, etc.) and exercise information regarding exercise (the number of steps, the amount of calories burned, whether or not a user engages in habitual exercise, intensity of exercise, frequency of exercise, etc.). For example, information regarding whether or not a user smokes, smoking history; and the like may be included. The activity status information may be information acquired by an activity tracker installed in a device (e.g., a wearable terminal or other portable terminal, etc.) that the user carries around or wears, or information input by an evaluator such as a user who performed evaluation, for example.

The basic information is information regarding the user's type and characteristics. For example, the basic information may include various types of information such as the user's height, weight, age, sex, body fat percentage, muscle mass, pulse rate, respiratory rate, blood pressure, and the like. The basic information may further include user's responses to questionnaires, information generated based on those responses, and information regarding the user's medical history. For example, responses to questionnaire items such as those used to diagnose people with intestinal disorders can objectively represent the user's physical constitution. The basic information is input by a user or the like in advance, for example, but there is no limitation to this. For example, the basic information may be information acquired by a wearable terminal or the like that the user wears, or information acquired from an external database or the like in which user information is rewarded.

The tasks can be defined as an action or behavior that the user has to work on, or a state that the user has to have achieved as a result of working on the action or behavior. Such tasks may be categorized into those regarding food, those regarding an activity status, and the like, for example. The tasks may contain elements regarding a predetermined amount (such as, but not limited to, time, number of times, frequency, and load level) that the user has to work on. For such a task, information indicating whether or not the task is set as a matter to be performed, whether or not the task has been performed, the progress status and degree of accomplishment regarding the execution of the task, or the like (called a value of a task) may be used. A value of one task can be treated as being related to a value of another value to which the task is related, and vice versa. For example, the fact that a user has executed the task of jogging a given distance may be treated as information indicating the amount of calories burned by the user in exercising, or the fact that a user has executed the task of consuming milk may be treated as information indicating the amount of calories or nutrients consumed by the user.

Figure 19:
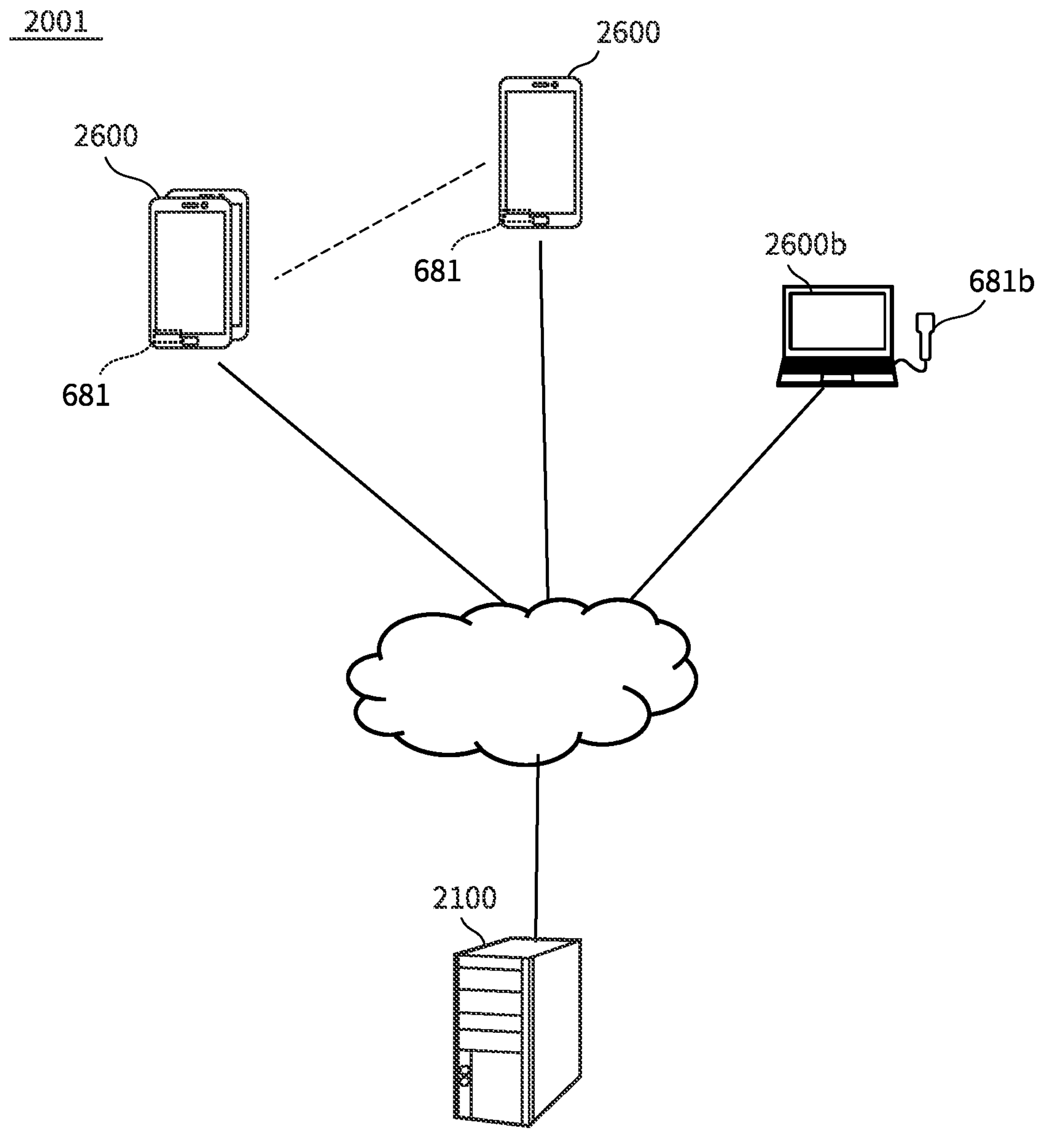
FIG. 19 is a diagram showing the outline of an information processing system according to Embodiment 2 of the present invention.

FIG. 19 is a diagram showing the outline of the information processing system 2001 according to Embodiment 2 of the present invention.

In this embodiment, the information processing system 2001 includes the information processing apparatus 2100 and terminal apparatuses 2600. The information processing apparatus 2100 and the terminal apparatuses 2600 can communicate with each other via a network such as a local area network or the Internet, for example. The configuration of the information processing system 2001 is not limited to this. There is no limitation on the number of each type of apparatuses included in the information processing system 2001, and other apparatuses may be included in the information processing system 2001.

Users of the information processing system 2001 can use the information processing system 2001 using the terminal apparatuses 2600. In FIG. 19, portable information terminal apparatuses such as so-called smartphones, each of which has a built-in microphone 681, are shown as the terminal apparatuses 2600, for example, but the terminal apparatuses 2600 are not limited to such portable information terminal apparatuses. For example, terminal apparatuses 2600*b* that are personal computers (PC) such as laptop computers may be used, or other apparatuses such as tablet-type information terminal apparatuses may be used. An external microphone 681*b* may be used as the microphone. In the following examples, it is assumed that portable information terminal apparatuses such as smartphones are used as the terminal apparatuses 200, but there is no limitation to this.

Figure 20:
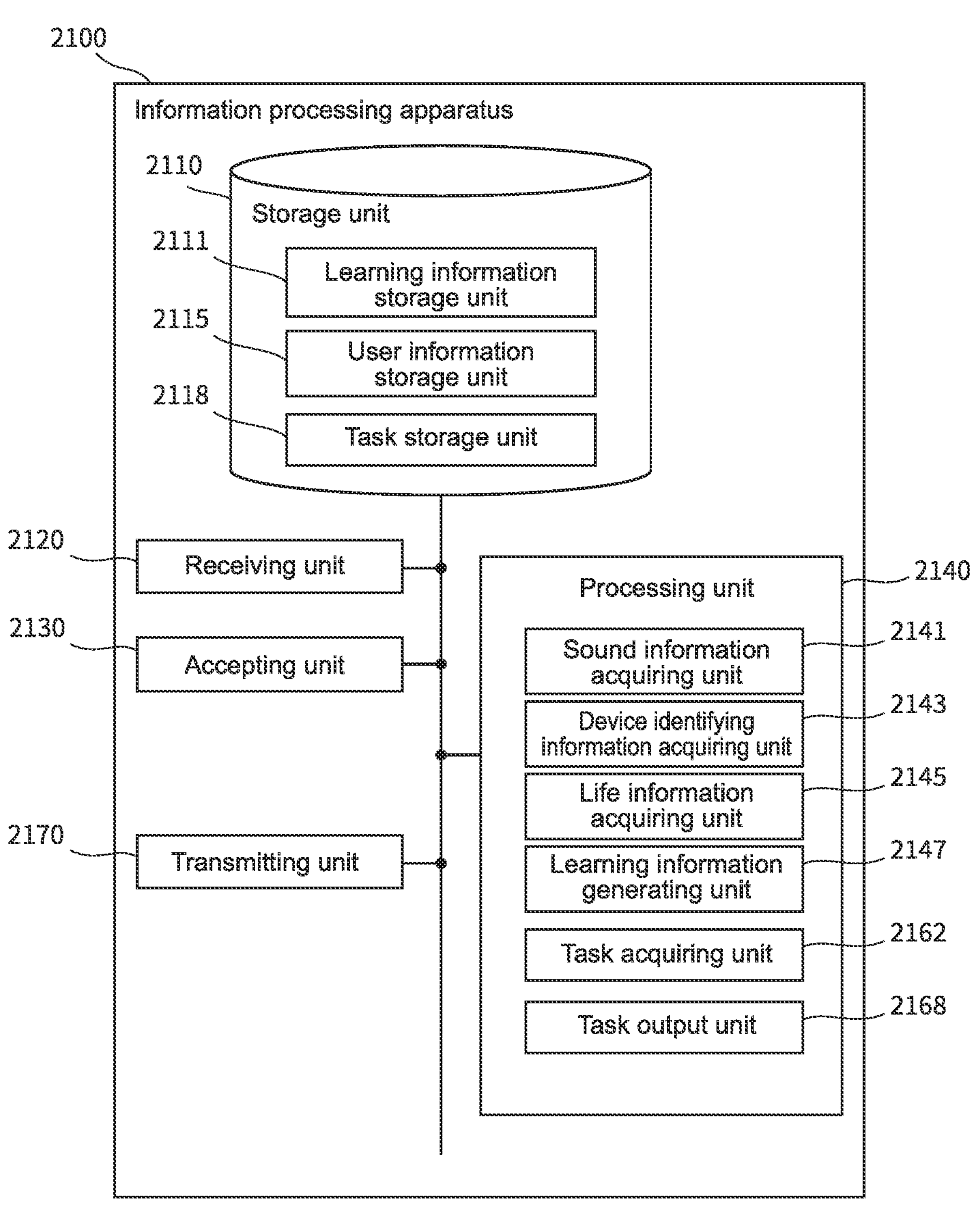
FIG. 20 is a block diagram of an information processing apparatus in the embodiment.
Figure 21:
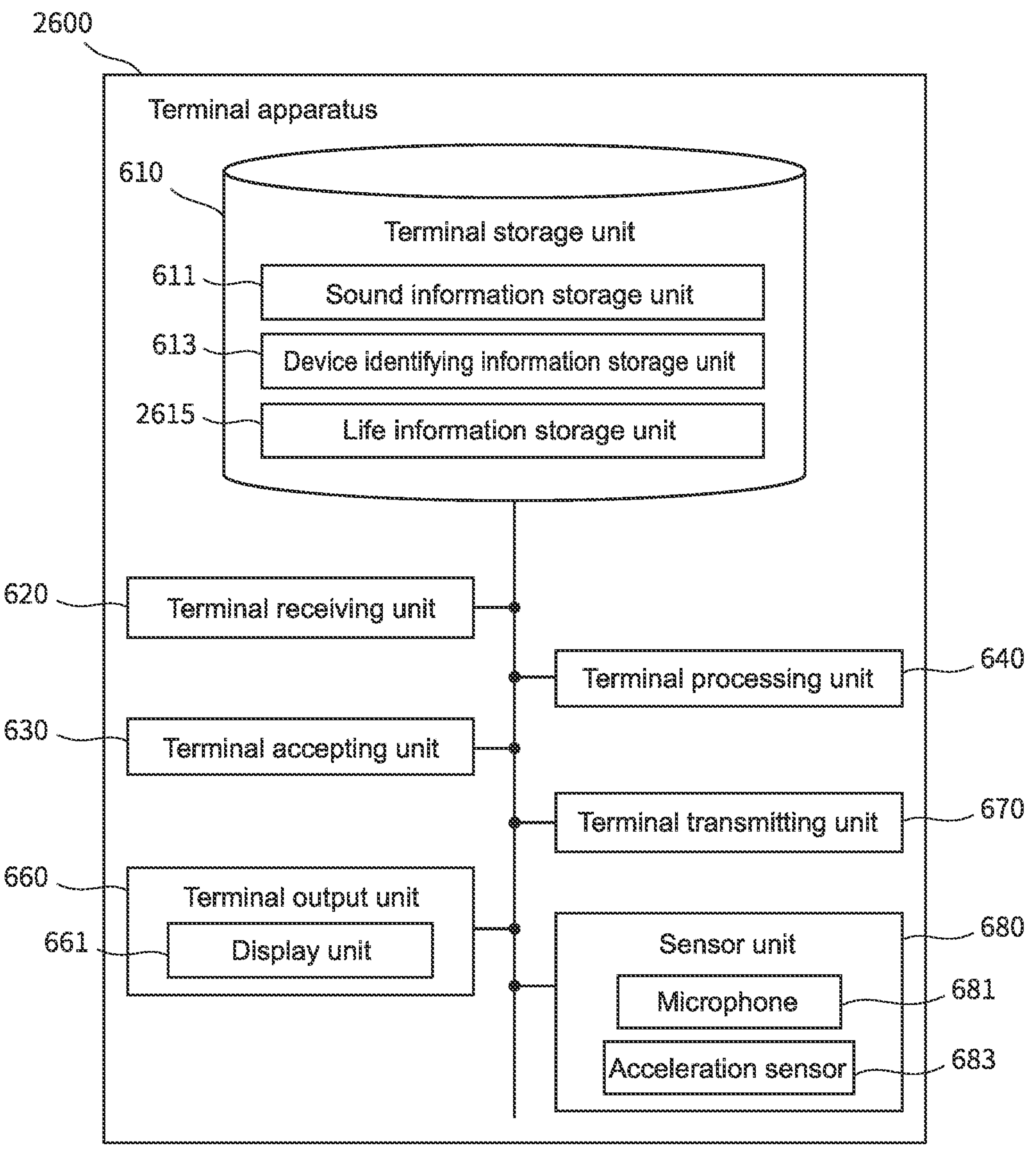
FIG. 21 is a block diagram of a terminal apparatus in the embodiment.

FIG. 20 is a block diagram of the information processing apparatus 2100 in the embodiment. FIG. 21 is a block diagram of a terminal apparatus 2600.

As shown in FIG. 20, the information processing apparatus 2100 includes a storage unit 2110, a receiving unit 2120, an accepting unit 2130, a processing unit 2140, and a transmitting unit 2170. The information processing apparatus 2100 is a server apparatus, for example.

The storage unit 2110 includes a learning information storage unit 2111, a user information storage unit 2115, and a task storage unit 2118.

Learning information that has been acquired in advance is stored in the learning information storage unit 2111. The learning information is generated by a learning information generating unit 2147 using a so-called machine learning method and stored in the learning information storage unit 2111, for example, as described later, but there is no limitation to this. That is to say, the learning information generated by an apparatus that is different from the information processing apparatus 2100 may be stored in the learning information storage unit 2111. The learning information is not limited to those generated using a machine learning method. The learning information may be a table indicating the correspondence between an input vector based on information for input or the like and information that is to be output, a function representing the relationship between an input vector based on the information for input or the like and information for generating information that is to be output, or the like, as with the above-described classifier.

In this embodiment, multiple pieces of learning information are prepared. The pieces of learning information are each stored in the learning information storage unit 2111 in association with device identifying information. The device identifying information is information corresponding to the sound information contained in the learning input used to generate the learning information, and is information for identifying the type and the like of a device used to acquire, that is, record abdominal sounds corresponding to the sound information, for example. The device identifying information may also be said to be information for identifying a method used to record abdominal sounds, for example. The device may mean a microphone used to record abdominal sounds, or an apparatus set including the microphone, for example. Specific examples of the device identifying information include, but are not limited to, a symbol for identifying the model of a device used to record abdominal sounds and a symbol for identifying the type of a device used to record abdominal sounds (e.g., whether a smartphone's built-in microphone was used or an external microphone was used), for example. Any symbol with which the origin of the learning input information, such as the recording method or the processing method of recorded abdominal sounds (e.g., whether or not a filter was applied, type, sound quality adjustment, etc.), can be identified at some granularity can be used as the device identifying information.

User information is stored in the user information storage unit 2115. In this embodiment, the user information is information for associating a user identifier, which is an identifier for identifying a user who uses the information processing system 2001, and information regarding the user.

The user information may contain various types of information. For example, the user information may contain information transmitted from the terminal apparatus 2600 that is used by the user, information on the user acquired by the information processing apparatus 2100 as described later, and the like. The information transmitted from the terminal apparatus 2600 that is used by the user corresponds to sound information, device identifying information, life information, and the like as described later, as well as the user's basic information, for example. The information on the user acquired by the information processing apparatus 2100 corresponds to an issue identifier, a task, or other information such as that regarding the frequency of gut sounds, a gut state estimation result, element scores, a gut score, and the like as described later, for example. User information transmitted from other external apparatuses and the like may be stored in the user information storage unit 2115.

Task association information containing two or more pairs each constituted by one issue identifier and one or more tasks in association with each other is stored in the task storage unit 2118. The issue identifier is for identifying an issue that the user has, for example. The issue is particularly a health-related issue, for example, regarding the activity or state of the digestive organs, such as slightly having diarrhea or constipation. For example, issues regarding a gut condition such as having diarrhea, constipation, or decreased peristalsis movements may be taken as the issue. Having decreased peristalsis movements means, for example, but not limited to, a state in which the frequency of peristalsis movements is low or the time of active peristalsis movements is relatively short. However, there is no limitation to this, and broad issues related to the state of physical and mental health may be taken as the issue. Differences from the activity state that is generally considered desirable, such as those regarding the content of the food and the like consumed or regarding the amount of exercise may be taken as the issue. In this embodiment, two or more issues are prepared in advance as those potentially related to the user. Each of them is associated with one or more tasks in the task association information.

Specifically, for example, a pair constituted by one issue identifier and one or more tasks in association with each other may be as follows. For example, tasks such as cutting back on spicy food and cutting back on alcohol may be associated with an issue of slightly having diarrhea. Tasks such as consuming dietary fibers and consuming predetermined drink may be associated with an issue of slightly having constipation. Tasks such as consuming predetermined drink and receiving a massage (massage treatment for a predetermined part of the body or the whole body, etc.) may be associated with an issue of having decreased peristalsis movements.

The receiving unit 2120 receives information transmitted from another apparatus. The receiving unit 2120 accumulates the received information in the storage unit 2110, for example. In this embodiment, the user inputs information using the terminal apparatus 2600 and transmits the information to the information processing apparatus 2100, for example. The receiving unit 2120 can accumulate each piece of transmitted information in the storage unit 2110 in association with a user identifier. In this embodiment, it is also possible to receive sound information transmitted from each terminal apparatus 2600 and accumulate the sound information in the storage unit 2110 in association with a user identifier, as will be described later. In the case of receiving these pieces of information from the terminal apparatus 2600, the receiving unit 2120 can specify a user identifier of the user pertaining to the transmission based on the transmitted information. The accepting unit 2130 accepts information input using an input part (not, shown) connected to the information processing apparatus 2100. The accepting unit 2130 accumulates the accepted information in the storage unit 2110, for example. The information may be input by any part such as a numeric keypad, a keyboard, a mouse, or a menu screen. The accepting unit 2130 may accept information input through an input operation performed using a reading apparatus (e.g., a code reader, etc.) connected to the information processing apparatus 2100 (e.g., including information read by the apparatus).

The accepting unit 2130 may be taken to accept the information received by the receiving unit 2120, as information input to the information processing apparatus 2100. That is to say, the input of information to the information processing apparatus 2100 may be interpreted to mean that these pieces of information are indirectly input to the information processing apparatus 2100 by the user via the terminal apparatus 2600 or the like, or directly input to the information processing apparatus 2100 by the user using an input part. The input of information to the information processing apparatus 2100 may also be taken to mean that the information is given to the information processing apparatus 2100 by the user executing a program that automatically generates information or giving various types of information to a program and causing the program to function.

The processing unit 2140 includes a sound information acquiring unit 2141, a device identifying information acquiring unit 2143, a life information acquiring unit 2145, a learning information generating unit 2147, a task acquiring unit 2162, and a task output unit 2168. The processing unit 2140 performs various types of processing. The various types of processing are processing that is performed by the constituent units of the processing unit 2140 as follows, for example.

The sound information acquiring unit 2141 acquires sound information on a user. In this embodiment, the sound information acquiring unit 2141 acquires sound information transmitted from the terminal apparatus 2600 of the user and received by the receiving unit 2120.

The device identifying information acquiring unit 2143 acquires device identifying information corresponding to the sound information. In this embodiment, the device identifying information is, but is not limited to, information transmitted from the terminal apparatus 2600 of the user in association with sound information. The device identifying information acquiring unit 2143 may be configured to acquire device identifying information stored in the storage unit 2110 as information for identifying the terminal apparatus 2600 of the user in advance.

The life information acquiring unit 2145 acquires life information. In this embodiment, the life information includes, but is not limited to, excretion-related information, eating-and-drinking information, and activity status information (i.e., exercise information or sleep information). The life information acquiring unit 2146 acquires the information stored in the user information storage unit 2115, for example. Furthermore, the life information acquiring unit 2145 may acquire the user's basic information.

The learning information generating unit 2147 generates learning information using a machine learning method. A machine learning method can be used as follows, for example. That is to say, a classifier in which input information containing sound information is taken as input and output information is taken as output is configured using a machine learning method. For example, two or more pairs (training data) of learning input information and output information for learning are prepared in advance, the two or more pairs of information are given to a module for configuring a machine learning classifier to configure a classifier, and the configured classifier is accumulated in the learning information storage unit 2111 as learning information. The classifier may also be said to be a learning model. There is no limitation on the machine learning method, and examples thereof include deep learning such as convolutional neural networks (CNN), random forests, and SVR. For example, functions in various machine learning frameworks and various existing libraries, such as fastText, tinySVM, random forest, and TensorFlow, can be used for the machine learning. It is sufficient that combinations of learning input information and output information for learning are prepared in advance. It is also possible to re-generate learning information at a predetermined point in time using a combination of sound information and output information newly acquired by the information processing apparatus.

In this embodiment, the learning information generating unit 2147 configures learning information, using two or more pieces of training data having learning input information containing sound information and output information containing an issue identifier for identifying an issue regarding a gut condition, for example. That is to say, information configured using two or more pieces of training data having learning input information containing sound information and output information containing an issue identifier for identifying an issue regarding a gut condition is stored as the learning information in the learning information storage unit 2111.

The task acquiring unit 2162 acquires one or more tasks corresponding to the user, using input information containing the sound information acquired by the sound information acquiring unit 2141 and learning information prepared in advance. In this embodiment, the task acquiring unit 2162 acquires the issue identifier by applying the input information containing the sound information acquired by the sound information acquiring unit 2141 to the learning information. The task acquiring unit 2162 acquires a task using the acquired issue identifier. The acquisition of the task using the task identifier is performed based on the task association information stored in the task storage unit 2118, for example. That is to say, the task acquiring unit 2162 searches the task association information for one or more tasks corresponding to an issue identifier acquired using the learning information (selects as candidates for acquisition), for example. Then, the searched one or more tasks (tasks selected as the candidates for acquisition) are acquired as the tasks corresponding to the user. In other words, the task acquiring unit 2162 acquires a task stored in the task storage unit 2118, using the acquired issue identifier.

In this embodiment, the task acquiring unit 2162 is configured to acquire the learning information corresponding to the device identifying information acquired by the device identifying information acquiring unit 2143, from the learning information storage unit 2111, and perform the above-described processing using the acquired learning information. Accordingly, the learning information corresponding to the properties and the like of the terminal apparatus 2600 used for recording the abdominal sound can be used, and thus more suitable output information can be acquired by applying the input information to the learning information.

In this embodiment, the sound information that is used by the learning information generating unit 2147 as learning input information and the sound information that is input by the task acquiring unit 2162 are spectrograms obtained by representing, in a predetermined form, results of Fourier transform analysis or fast Fourier transform analysis performed on the sound data (which may be processed) obtained by recording abdominal sounds. The sound information may be sound data (which may be processed) itself or data converted to other formats. The sound information that is used by the learning information generating unit 2147 as learning input information and the sound information that is input by the task acquiring unit 2162 may be prepared by the processing unit 2140. Sound information in the form of a spectrogram may be prepared in advance by a device other than the information processing apparatus 2100, such as a device that recorded abdominal sounds, and transmitted to the information processing apparatus 2100.

The learning information generating unit 2147 and the task acquiring unit 2162 may be configured to use learning input information containing user information such as basic information, in accordance with generation and use of the learning information. In this case, the learning information that is generated may be stored in the learning information storage unit 2111, for each type by which users can be classified according to the user information, in association with an identifier for identifying the type. It is sufficient that the task acquiring unit 2162 is configured to acquire learning information of a type corresponding to an identifier specified based on the user information, from the learning information storage unit 2111, and acquire a task using the learning information. Accordingly, more accurate output results can be obtained. Furthermore, the life information may be contained in the input information.

The task acquiring unit 2162 may acquire a task that satisfies a predetermined acquisition condition out of the tasks selected as the candidates for acquisition. Various acquisition conditions may be set.

For example, the task acquiring unit 2162 may be configured to acquire a task identifier for identifying a task currently or previously applied for a user, and acquire one or more tasks corresponding to the user based on the acquired task identifier. In this embodiment, the task acquiring unit 2162 acquires a task different from a task currently applied for a user. In this case, the acquisition condition may be expressed as being that the task is different from the task currently applied for the user. For example, the task acquiring unit 2162 is configured to preferentially acquire a task that is different from the currently applied task, out of the tasks corresponding to the issue identifier acquired using the learning information. In this embodiment, if all of the tasks corresponding to the issue identifier acquired using the learning information are currently applied tasks, the task acquiring unit 2162 acquires these tasks, but there is no limitation to this. If tasks that are different from the currently applied tasks can be acquired in this manner, tasks that are fresh for the user can be presented to the user. The task acquiring unit 2162 may be configured to acquire a task that does not correspond to tasks that have been applied not only in the present, but also in the past predetermined periods. In contrast, the task acquiring unit 212 may preferentially acquire a currently or previously applied task out of the tasks corresponding to the issue identifier. In this case, the acquisition condition may be expressed as being that the task is the same as the currently or previously applied task. Accordingly, tasks that are familiar to the user and easy to work on can be presented. In this case of acquiring the current task based on the task identifiers of previously applied tasks in this manner, the current task may be acquired based on a task that the user has completed (which can be said to be a task that has been accomplished or executed, etc.) out of the previously applied tasks. That is to say, the current task may be acquired based on a task identifier of a currently or previously applied task and execution information of the task.

The task acquiring unit 2162 accumulates the acquired task in the user information storage unit 2115 in association with a user identifier. The task acquiring unit 2162 may accumulate the acquired task as a task to be output to the user, or may accumulate the acquired task in a state in which it is applied to the user as a task to be worked on by the user.

The task acquiring unit 2162 may change such a predetermined method used with respect to the acquisition of a task as appropriate based on the user's basic information. Specifically, for example, the task acquiring unit 2162 may be configured to acquire an issue identifier using sound information or to select a task to be acquired out of the tasks corresponding to the issue identifier, according to different methods according to the user's sex, age, height, weight, medical history, results of predetermined questionnaires, and the like. That is to say, the task acquiring unit 2162 may acquire a task based on the user's basic information.

The task output unit 2168 outputs information on the tasks acquired by the task acquiring unit 2162. The outputting information on a task may be, but not limited to, transmitting the information from the transmitting unit 2170 to the user's terminal apparatus 2600 or storing the information in the storage unit 2110 of the information processing apparatus 2100 or other apparatuses (including transmitting messages such as e-mails) such that the user can acquire the information using the terminal apparatus 2600 or the like. The information that is output by the task output unit 2168 contains a task identifier for identifying a task and other information corresponding thereto (e.g., information corresponding to a task identifier in the task association information), for example, but there is no limitation to this. For example, the information may contain only a task identifier. In this case, the terminal apparatus 2600 or the like that received the task identifier may acquire other information corresponding to the task identifier.

In this embodiment, if two or more tasks are specified as candidates for acquisition, the task acquiring unit 2162 may acquire information on one task specified at random out of the two or more tasks. This may be expressed as the task output unit 2168 outputting information on one task specified at random when two or more tasks are acquired by the task acquiring unit 2162. If three or more tasks are acquired by the task acquiring unit 2162, the task output, unit 2168 may output information on two or more tasks specified at random. If two or more tasks are acquired by the task acquiring unit 2162, the task output unit 2168 may output a smaller number of tasks than the number of tasks acquired, using a method other than those described above.

The transmitting unit 2170 transmits information via a network to another apparatus constituting the information processing system 2001. The transmitting unit 2170 transmits information to the terminal apparatus 2600, for example. In other words, the transmitting unit 2170 outputs information to the terminal apparatus 2600, for example.

Next, the configuration of the terminal apparatus 2600 will be described.

The terminal apparatus 2600 has substantially the same configuration as that of the terminal apparatuses 600 according to Embodiment 1. That is to say, as shown in FIG. 21, the terminal apparatus 2600 includes a terminal storage unit 610, a terminal receiving unit 620, a terminal accepting unit 630, a terminal processing unit 640, a terminal output unit 660, a terminal transmitting unit 670, and a sensor unit 680. The terminal output unit 660 includes a display unit 661. The sensor unit 680 includes a microphone 681 and an acceleration sensor 683.

The terminal apparatus 2600 is different from the terminal apparatuses 600 in that the terminal storage unit 610 includes a life information storage unit 2615 instead of the activity information storage unit 615.

Life information is accumulated in the life information storage unit 2615. The life information, which is transmitted by the terminal transmitting unit 670 to the information processing apparatus 2100, may be deleted from the life information storage unit 2615 when the transmission is completed, retained as it is until a predetermined period elapses, or retained permanently until a deletion operation is performed by the user.

The life information that is accumulated in the life information storage unit 2616 may contain information input by the user or information based thereon. These pieces of information may be information accepted by the terminal accepting unit 630 or information acquired by the terminal processing unit 640 through calculation or the like based on the information accepted by the terminal accepting unit 630, for example.

Furthermore, the life information that is accumulated in the life information storage unit 2615 may contain a measured value or information based thereon. These pieces of information may be information measured by the sensor unit 680 or information acquired by the terminal processing unit 640 through calculation or the like based on the information measured by the sensor unit 680, for example. Also, it, may be information obtained through measurement or the like by a sensor apparatus communicably connected to the terminal apparatus 2600 and transmitted to the terminal apparatus 2600.

The storage unit 2110 described above is preferably a non-volatile recording medium, but may alternately be realized by a volatile recording medium. The pieces of information acquired by its corresponding apparatus are stored in the unit, but there is no limitation on the procedure in which information is stored therein. For example, information and the like may be stored therein via a recording medium, information and the like transmitted via a communication line or the like may be stored therein, or information and the like input via an input device may be stored therein.

Furthermore, the processing unit 2140 described above may be realized typically by an MPU, a memory, or the like. Typically, the processing procedure of the processing unit 2140 is realized by software, and the software is stored in a recording medium such as a ROM. The processing procedure may be realized by hardware (dedicated circuits).

Furthermore, information that can be accepted by the accepting unit 2130 may be input by any part such as a numeric keypad, a keyboard, a mouse, or a menu screen. The accepting unit 2130 may be realized by a device driver for an input part such as a numeric keypad or a keyboard, control software for a menu screen, or the like.

Furthermore, the receiving unit 2120 is typically realized by a wireless or wired communication part, but may also be realized by a broadcast receiving part.

Furthermore, the transmitting unit 2170 is typically realized by a wireless or wired communication part, for example, but may also be realized by a broadcasting part.

Next, an example of an operation of the information processing apparatus 2100 performed when a user uses the information processing system 2001 according to this embodiment will be described. In this embodiment, the user can use the information processing system 2001 by causing a predetermined application to work on the terminal apparatus 2600 while accessing the information processing apparatus 2100 via the terminal apparatus 2600 or receiving information transmitted from the information processing apparatus 2100, for example. The predetermined application may be a dedicated application that operates using information transmitted from the information processing apparatus 2100, a web browser on which a web application provided by the information processing apparatus 2100 is displayed in a usable manner, or the like, for example.

In this embodiment, the information processing system 2001 is typically used as follows. That is to say, the user records his or her own abdominal sounds using the terminal apparatus 2600. Then, sound information is transmitted from the terminal apparatus 2600 to the information processing apparatus 2100, and a task is acquired by the information processing apparatus 2100. The information processing apparatus 2100 transmits (outputs) the acquired task to the terminal apparatus 2600. The terminal apparatus 2600 receives the task, and the terminal output unit 660 displays information containing the task on a display device. Accordingly, the user can check information regarding the task recommended by the information processing system 2001 as a task that he or she has to execute. Since appropriate tasks are presented according to the abdominal sounds, the user can learn about and work on tasks related to his or her own health. In the case in which the information processing system 2001 operates in this manner, the information processing apparatus 2100 performs various operations as follows, for example. These operations are performed by the processing unit 2140 executing control operations and the like while using the constituent units.

Figure 22:
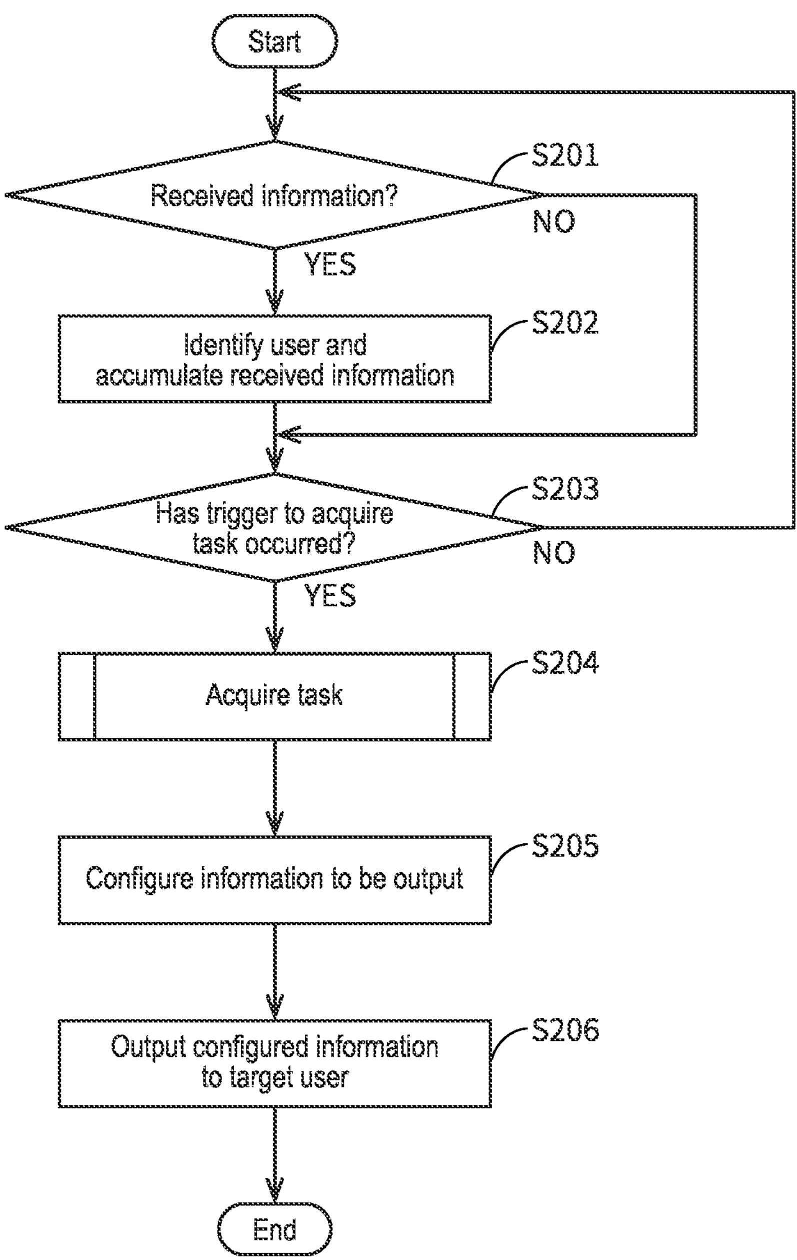
FIG. 22 is a flowchart showing an example of an operation of the information processing apparatus in the embodiment.

FIG. 22 is a flowchart showing an example of an operation of the information processing apparatus 2100 in the embodiment.

(Step S201) The processing unit 2140 determines whether or not information transmitted from the terminal apparatus 2600 or the like has been received by the receiving unit 2120. If it is determined that the information has been received, the procedure advances to step S202, or otherwise the procedure advances to step S203.

(Step S202) The processing unit 2140 identifies the user based on the received information, and accumulates the received information in the user information storage unit 2115 in association with a user identifier. For example, when life information, sound information, device identifying information, or the like is transmitted from the terminal apparatus 2600 in association with a user identifier, the processing unit 2140 accumulates the received information in the user information storage unit 2115 in association with the user identifier.

(Step S203) The processing unit 2140 determines whether or not a trigger to acquire a task has occurred (a trigger has been kicked). In other words, the processing unit 2140 determines whether or not the conditions for starting acquisition of a task have been satisfied. If it is determined that the trigger has occurred, the procedure advances to step S204. Otherwise, the procedure returns to step S201.

For example, the above-mentioned trigger may be a user's instruction to acquire a task through the terminal apparatus 2600 (transmission of predetermined information corresponding to the instruction) or the like, but the trigger is not limited to this. For example, the trigger may be fulfillment of various conditions such as arrival of a predetermined time or new receipt of sound information or other life information.

(Step S204) The processing unit 2140 causes the task acquiring unit 2162 to perform task acquiring processing. The task acquiring processing will be described later. Through the task acquiring processing, information on a task of the user is acquired and accumulated in the user information storage unit 2115.

(Step S205) The processing unit 2140 causes the task output unit 2168 to configure information that is to be output, using the acquired information on a task. In this embodiment, information for showing the task and information for showing the information on a task on the terminal apparatus 2600 is configured.

(Step S206) The processing unit 2140 causes the task output unit 2168 to output the configured information to the target user. That is to say, the processing unit 2140 causes the transmitting unit 2170 to output the information configured for the task to the terminal apparatus 2600 that is used by the user whose scores are to be calculated. Accordingly, the terminal apparatus 2600 that received the information can perform display regarding the task.

Figure 23:
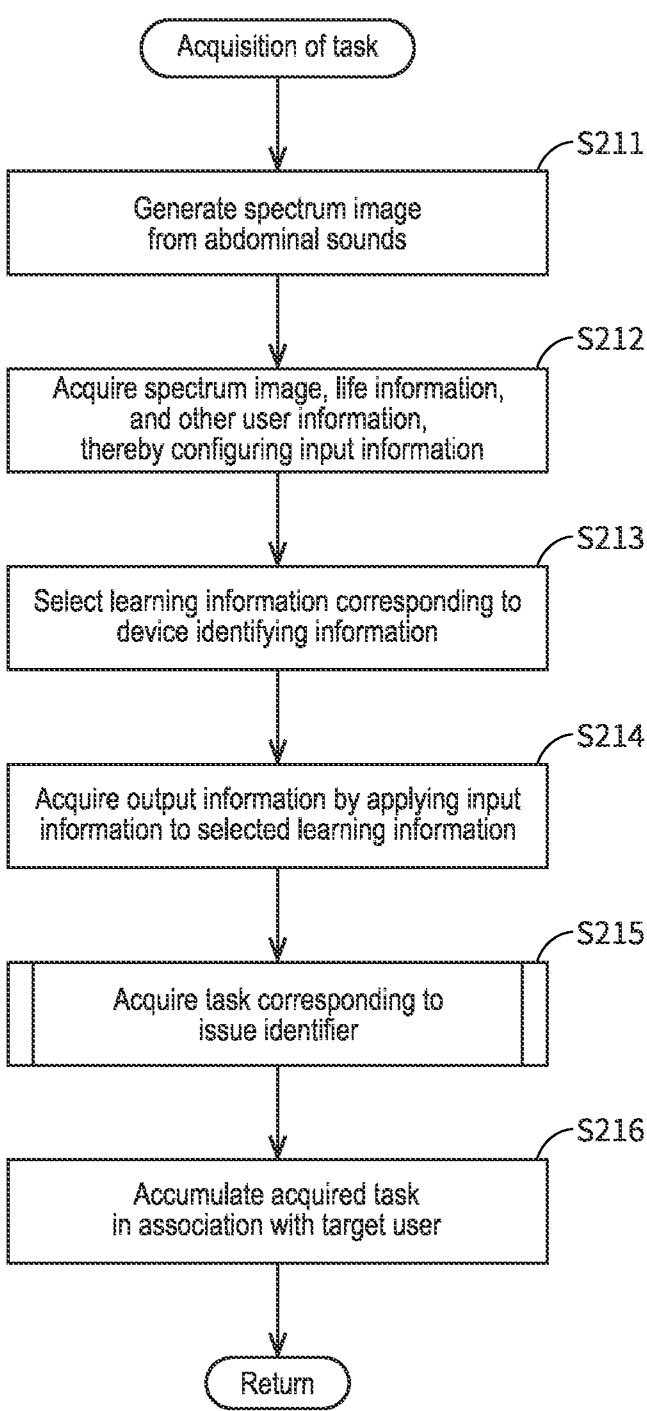
FIG. 23 is a flowchart showing an example of task acquiring processing of the information processing apparatus in the embodiment.

FIG. 23 is a flowchart showing an example of the task acquiring processing of the information processing apparatus 2100 in the embodiment.

(Step S211) The task acquiring unit 2162 generates a spectrogram from sound information, which is sound data obtained by recording abdominal sounds.

(Step S212) The task acquiring unit 2162 acquires the generated spectrogram, life information, past user information, and the like regarding a target user from the user information storage unit 2115 based on the user identifier of the user. Basic information may be acquired.

(Step S213) The task acquiring unit 2162 selects, as learning information that is to be used, learning information corresponding to the device identifying information corresponding to the sound information, out of the learning information stored in the learning information storage unit 2111.

(Step S214) The task acquiring unit 2162 acquires output information by applying input information to the selected learning information. Accordingly, in this embodiment, an issue identifier is acquired.

(Step S215) The task acquiring unit 2162 acquires a task corresponding to the acquired issue identifier (corresponding task acquiring processing). The corresponding task acquiring processing will be described later.

(Step S216) The task acquiring unit 2102 accumulates the acquired task in the user information storage unit 2115 in association with a user identifier of the target user. Subsequently, the procedure returns to the processing in FIG. 22.

In the case in which the sound information stored in the user information storage unit 2115 is a spectrogram such as the case in which the sound information transmitted from the terminal apparatus 2600 is a spectrogram, it is sufficient that the processing in step S221 is not performed. It is also possible that a spectrogram is not taken as an input image, and the recorded sound data is used as is as the sound information.

FIG. 24 is a diagram showing an example of task association information for use in the information processing apparatus 2100 in the embodiment.

As shown in FIG. 24, in the task association information, for example, an issue identifier and a task identifier for identifying a task are associated with each other. In this embodiment, the task association information further contains the name of the task, a description of the task, a product identifier for identifying a product related to the task, and the like corresponding to the task identifier. The task association information is not limited to this, and may further contain attribute values of other attributes or may not contain any of the attribute values mentioned above.

In FIG. 24, various attribute values are listed as examples. The issue identifier includes a string that uniquely identifies an issue, such as "peristalsis movements" indicating decreased peristalsis movements, "slightly having diarrhea", or "slightly having constipation". The task identifier includes a string that uniquely identifies the task, such as indicated by each attribute value in the name of the task or a description of the task. The product identifier includes a string that can uniquely identify a specific product in the case in which there is a specific product related to the execution of the task, for example. The identifiers and other attribute values are not limited to this, and may be information indicating other resources, key values used in other tables, or the like.

Figure 25:
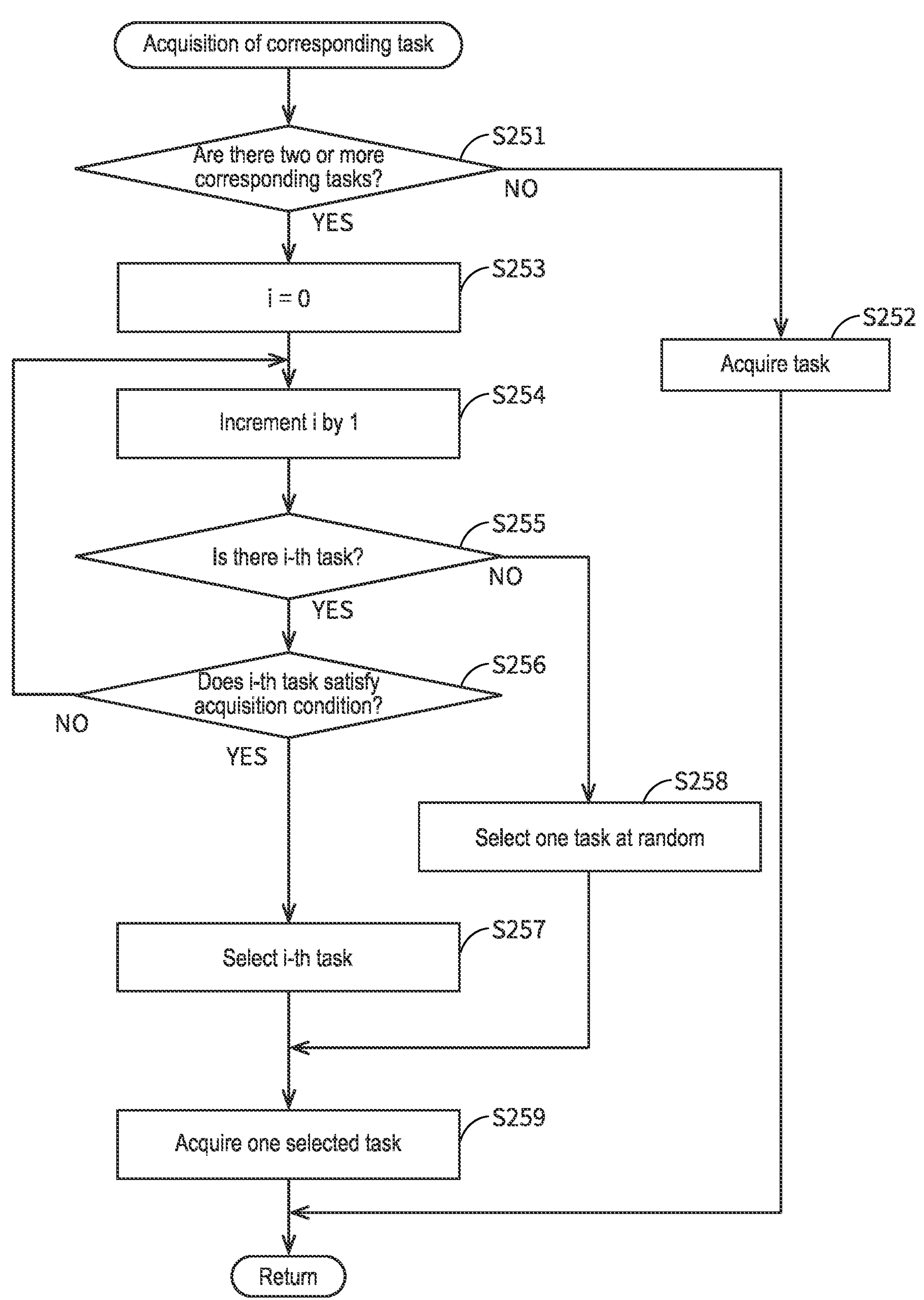
FIG. 25 is a flowchart showing an example of corresponding task acquiring processing of the information processing apparatus in the embodiment.

FIG. 25 is a flowchart showing an example of the corresponding task acquiring processing of the information processing apparatus 2100 in the embodiment.

In the example shown in FIG. 25, if there is only one task that is a candidate for acquisition, the task acquiring unit 2162 acquires that task. On the other hand, if there are two or more tasks that are candidates for acquisition, the task acquiring unit 2162 acquires one task that is different from the task that has been applied (currently or previously). If no such task is a candidate for acquisition, the task acquiring unit 2162 acquires one task selected at random out of the candidates for acquisition.

(Step S251) The task acquiring unit 2162 searches for task association information using the acquired issue identifier, and specifies tasks corresponding to the issue identifier. The task acquiring unit 2162 determines whether the number of tasks specified is two or more. If it determines that the number is two or more, the procedure advances to step S253, or otherwise the procedure advances to step S252.

(Step S262) The task acquiring unit 2162 acquires only one specified task, and the procedure returns to the processing in FIG. 23.

(Step S253) The task acquiring unit 2162 sets a counter i to zero. It may be said that the counter i is reset.

(Step S254) The task acquiring unit 2162 increments the counter i by 1. It may be said to add 1 to the value of the counter i.

(Step S255) The task acquiring unit 2162 determines whether or not, there is an in task in the specified tasks. If these is such a task, the procedure advances to step S256, or otherwise the procedure advances to step S258.

(Step S256) The task acquiring unit 2162 determines whether or not the $i^{th}$ task satisfies a predetermined acquisition condition. If it is determined that the task satisfies the acquisition condition, the procedure advances to step S257, or otherwise the procedure returns to step S254. The acquisition condition is that the task is different from the task currently or previously applied for a user, for example.

(Step S257) The task acquiring unit 2162 selects the $i^{th}$ task. Subsequently, the procedure advances to step S259.

(Step S258) The task acquiring unit 2162 selects one task at random out of the tasks that are candidates for acquisition. Subsequently, the procedure advances to step S259.

(Step S259) The task acquiring unit 2162 acquires the selected one task. Subsequently, the procedure returns to the processing in FIG. 23.

If one task is acquired through the corresponding task acquiring processing in this manner, information on the task is output. Thus, even when multiple tasks are candidates for acquisition, information on one task can be selected out of them and communicated to the user. Therefore, the user can learn information on a task and work on the task without feeling an excessive burden due to the large number of tasks. In addition, in the above-described example, tasks that are different from the current or past tasks are acquired and output to all extent possible. Thus, the user can preferentially learn about or work on tasks that are fresh for him or her.

Next, specific examples of an operation of the information processing system 2001 in this embodiment will be described with reference to the screen transition of the terminal apparatus 2600 that is used by the user.

In the following specific examples, a case is assumed in which the information processing system 2001 provides a health support application to assist a user to lead a healthy life. The health support application accepts input operations related to life information of a user and provides the user with information useful for maintaining good health. The health support application is realized when the user executes a predetermined application on the terminal apparatus 2600 and communication is performed between the terminal apparatus 2600 and the information processing apparatus 2100. The following screen examples of the health support application are displayed by the terminal output unit 660 based on the control by the terminal processing unit 640.

Figure 26:
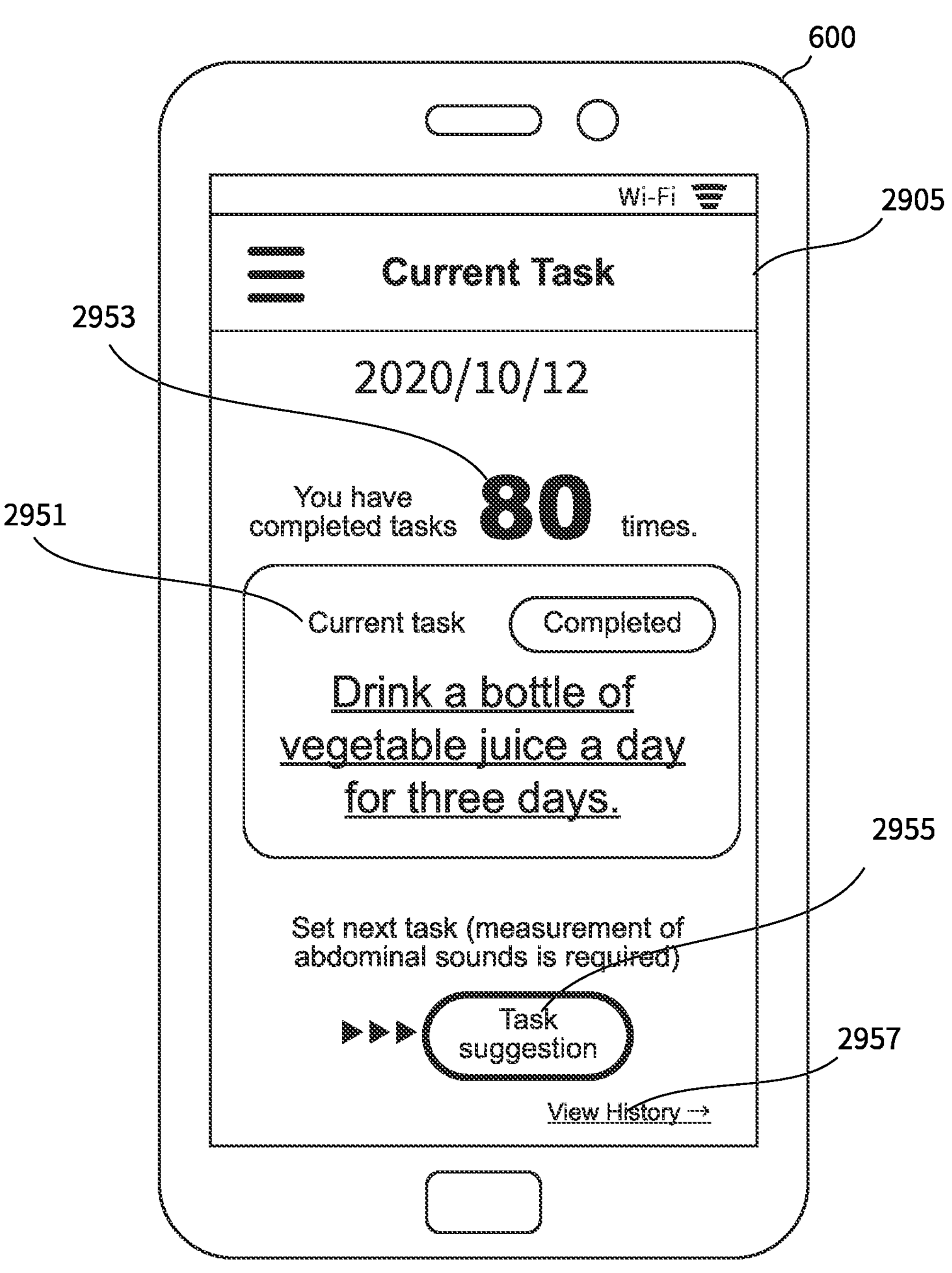
FIG. 26 is a first diagram showing a specific example of screen transition of the terminal apparatus in the embodiment.

FIG. 26 is a first diagram showing a specific example of screen transition of the terminal apparatus 2600 in the embodiment.

FIG. 26 shows a task display screen 2905 of the health support application. The task display screen 2905 includes a task display area 2951 that displays information on a score currently set for a user, an execution results display area 2953 that displays information regarding execution results such as the number of times the task has been completed, a task suggestion button 2955 for newly suggesting a task, a history display button 2957 that allows the user to check the task setting history, and the like, for example. The user can cause the terminal apparatus 2600 to record abdominal sounds and to transition the screen to a task suggestion screen 2906 by operating the task suggestion button 2955. The user can check the task setting records by operating the history display button 2957. If the task suggestion button 2955 is operated, abdominal sounds are recorded, and then the screen transitions to the task suggestion screen 2906.

The task display area 2951 contains a name of a task and a description thereof, for example. The task display area 2951 may further contain information regarding the execution status of the set task. For example, information indicating whether or not the task has been completed and the degree of execution may be contained.

Figure 27:
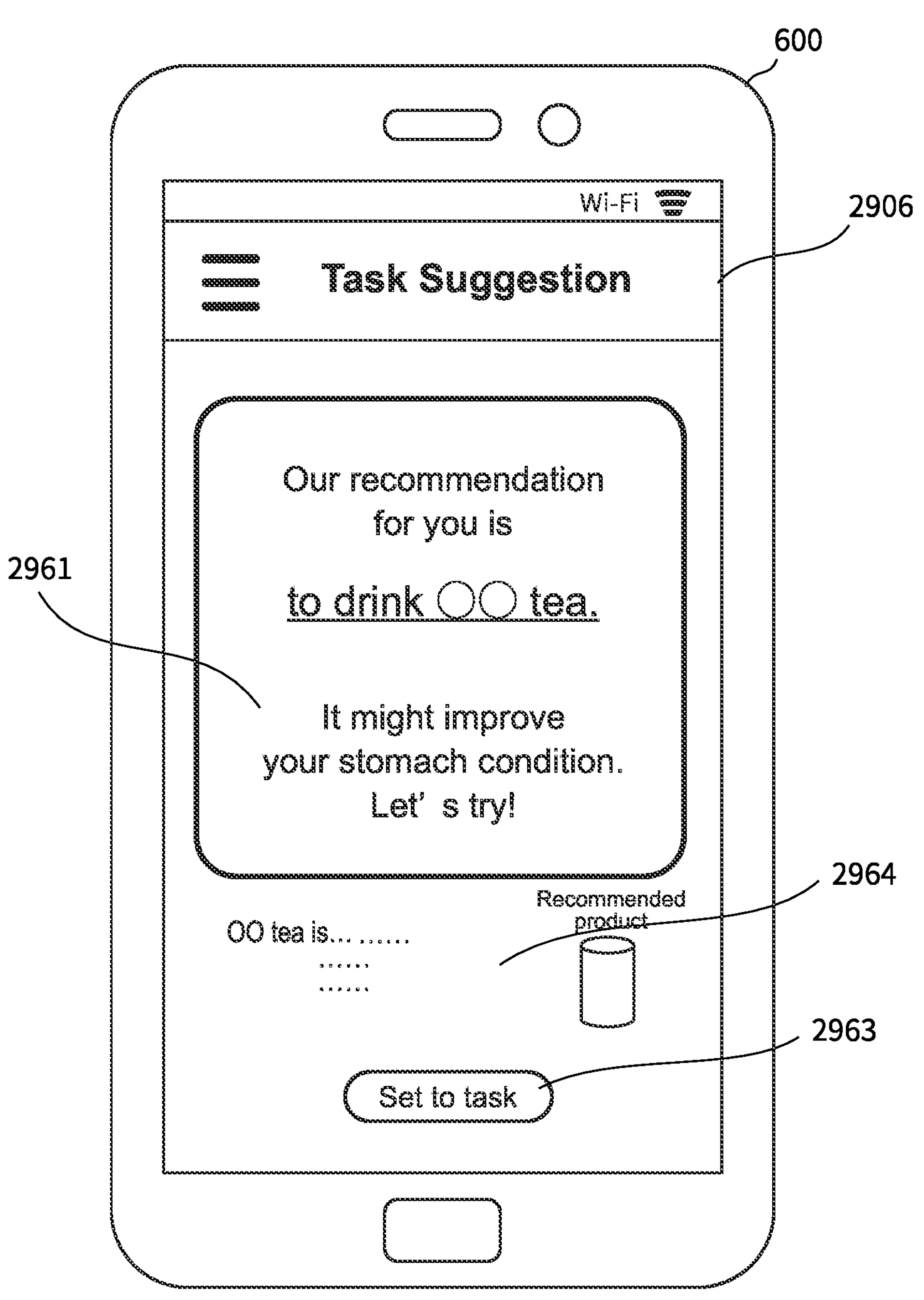
FIG. 27 is a second diagram showing a specific example of screen transition of the terminal apparatus in the embodiment.

FIG. 27 is a second diagram showing a specific example of screen transition of the terminal apparatus 2600 in the embodiment.

FIG. 27 shows the task suggestion screen 2906 of the health support application. As shown in FIG. 27, the task suggestion screen 2906 includes a task display area 2961 that displays output task, and a task setting button 2963 for accepting operations to set the displayed task as a task to be performed by the user, for example. The user can recognize that the task may effectively contribute to improving his or her health state, by checking the task displayed in the task display area 2961. Also, the user can easily set, the displayed task as a task to be performed by the user, by operating the task setting button 2963. That is to say, if the information processing apparatus 2100 outputs information on such a task to the terminal apparatus 2600 such that it is displayed on the task suggestion screen 2906, the user can be easily and effectively motivated to effectively improve his or her health state.

In this specific example, the task suggestion screen 2906 further includes a related information display area 2964. The related information display area 2964 displays information related to the task contained in the output information. For example, a description of a task or information on a product related to the task displayed in the task display area 2961 may be included. Accordingly, it is possible to make the user more aware of information regarding the task to be performed and to effectively motivate the user to purchase related products. The information related to the task may be, but is not, limited to, information based on task association information, for example.

As explained above, it can be said that the information processing apparatus 2100 can realize the following information processing method using the learning information and the sound information stored in the storage unit 2110. That is to say, the information processing apparatus 2100 acquires sound information regarding abdominal sounds, which are sounds emanating from the abdomen, of a user, acquires one or more tasks corresponding to the user, using input information containing the acquired sound information and learning information prepared in advance, and outputs information on the acquired tasks. Since the tasks acquired based on sound information are output, the user can easily learn about objectively selected tasks suitable for him or her. In this embodiment, since the tasks corresponding to the issue identifier are output, the user can easily learn about the tasks corresponding to the issue regarding the user's gut condition.

Description of Modified Examples of Embodiment 2

In Embodiment 2 above, a task corresponding to an issue identifier contained in output information of learning information is acquired and output, but the output information of learning information may contain information with which the task can be identified. That is to say, information configured using two or more pieces of training data having input information containing sound information and output information containing a task identifier for identifying a task for improving a gut condition may be used as the learning information. In this case, the task acquiring unit 2162 acquires output information containing a task identifier by applying input information containing the sound information acquired by the sound information acquiring unit 2141 to the learning information. That is to say, a task is acquired. Then, the task output unit 2168 outputs the acquired task. In this modified example, for example, it is sufficient, that the task acquiring processing is performed as described below.

Figure 28:
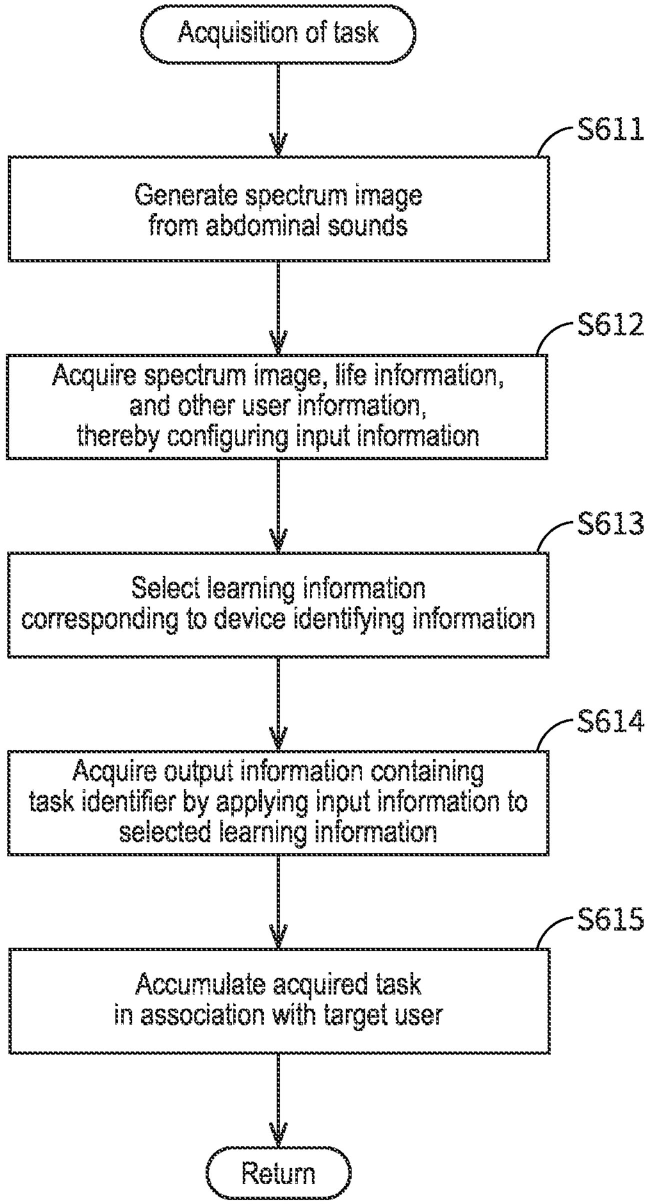
FIG. 28 is a flowchart showing an example of task acquiring processing of the information processing apparatus in the embodiment.

FIG. 28 is a flowchart showing an example of the task acquiring processing of the information processing apparatus 2100 in the embodiment.

The processing of steps S611 to S613 is similar to that of steps S211 to S213 in Embodiment 2 above. That is to say, the task acquiring unit 2162 generates a spectrogram from sound information, acquires various types of information based on a user identifier of the user, and selects learning information that is to be used.

(Step S614) The task acquiring unit 2162 acquires output information by applying input information to the selected learning information. In this embodiment, output information containing information on the task identifier is acquired. Accordingly, in this embodiment, a task identifier, that is, a task is acquired.

(Step S615) The task acquiring unit 2162 accumulates the acquired task in the user information storage unit 2115 in association with a user identifier of the target user. Subsequently, the procedure returns to the processing in FIG. 22.

In this manner, the effects similar to those described above can be obtained also in the case in which output information obtained using the learning information contains a user identifier, and task output unit 2162 is configured to acquire a task using the learning information.

Embodiment 3

Hereinafter, the outline of Embodiment 3 will be described focusing on aspects different from those in Embodiment 2 above. In Embodiment 3, the information processing system 2001 including an information processing apparatus 2200 and terminal apparatuses 2600 having a configuration similar to that of Embodiment 2 is used. This embodiment is different from Embodiment 2 in that the information processing apparatus 2200 configured to output a task using a score indicating a gut condition is used instead of the information processing apparatus 2100.

That is to say, in Embodiment 3, the learning information is generated such that information containing the sound information is taken as input information and a value of a predetermined indicator regarding an activity state of the guts is taken as output information, and the information processing apparatus 2200 selects a task using a value of the predetermined indicator acquired using the learning information. The predetermined indicator is preferably at least, one of a bowel movement, state and the number of peristalsis movements of the guts per unit time, and the frequency of abdominal sounds, for example. Tasks associated with the predetermined indicator are prepared in advance, and are output based on the acquired value of the predetermined indicator. Hereinafter, the information processing apparatus 2200 of the information processing system 2001 configured in this way will be described.

Figure 29:
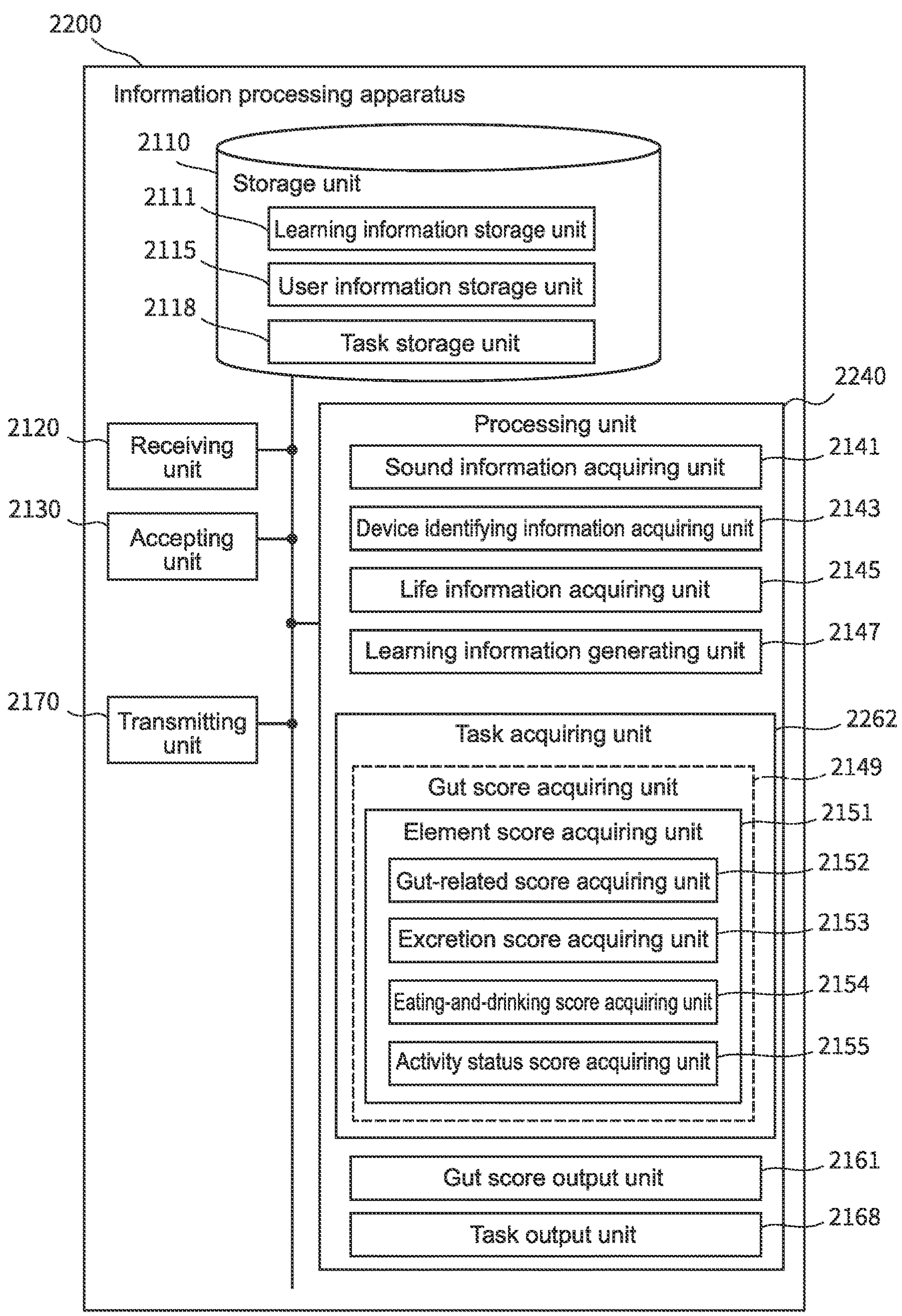
FIG. 29 is a block diagram of an information processing apparatus according to Embodiment 3 of the present invention.

FIG. 29 is a block diagram of the information processing apparatus 2200 according to Embodiment 3 of the present invention.

The information processing apparatus 2200 includes the storage unit 2110, the receiving unit 2120, the accepting unit 2130, and the transmitting unit 2170 having a configuration similar to that of Embodiment 2 above. The information processing apparatus 2200 includes a processing unit 2240 instead of the processing unit 2140.

The processing unit 2240 includes the sound information acquiring unit 2141, the device identifying information acquiring unit 2143, the life information acquiring unit 2145, the learning information generating unit 2147, and the task output unit 2168. In this embodiment, the processing unit 2240 includes a task acquiring unit 2262 and a gut score output unit 2161.

In this embodiment, the learning information generating unit 2147 generates learning information through machine learning using two or more pairs of learning input information containing sound information and output information containing a value of a predetermined indicator regarding an activity state of the guts. That is to say, learning information in which sound information is taken as input information and output information containing a value of a predetermined indicator is output is stored in the learning information storage unit 2111.

The task acquiring unit 2262 in this embodiment includes a gut score acquiring unit 2149. The task acquiring unit 2262 causes the gut score acquiring unit 2149 to acquire a value of a predetermined indicator by applying the input information containing the sound information acquired by the sound information acquiring unit 2141 to the learning information. The task acquiring unit 2262 acquires a task using the acquired value of the predetermined indicator.

The gut score acquiring unit 2149 acquires a gut score related to a gut condition of the user, using input information containing the sound information acquired by the sound information acquiring unit 2141 and learning information prepared in advance. In this embodiment, the gut score acquiring unit 2149 includes an element score acquiring unit 2151. The element score acquiring unit 2151 includes a gut-related score acquiring unit 2162, an excretion score acquiring unit 2153, an eating-and-drinking score acquiring unit 2154, and an activity status score acquiring unit 2155.

The gut score acquiring unit 2149 in this embodiment acquires a value of a predetermined indicator using the learning information stored in the learning information storage unit 2111, and acquires a gut score using the value of the output indicator. The processing for acquiring a value of a predetermined indicator is performed by the gut-related score acquiring unit 2152, which will be described later, for example. For example, at least one of the bowel movement state and the number of peristalsis movements of the guts per unit time is used as the predetermined indicator. The number of peristalsis movements of the guts may also be said to be the frequency of abdominal sounds at a predetermined level or greater (alternatively referred to simply as the "frequency of gut sounds" hereinafter). The gut score acquiring unit 2149 is configured to acquire learning information corresponding to the device identifying information acquired by the device identifying information acquiring unit 2143, from the learning information storage unit 2111, and acquire a gut score using the acquired learning information.

In this embodiment, the gut score acquiring unit 2149 acquires a gut score using the element scares acquired by the element score acquiring unit 215L The element score acquiring unit 2151 causes the constituent units to acquire element scores respectively for two or more evaluation elements based on the input information, as will be described later. The two or mom evaluation elements may be gut-related elements, such as excretion, drink, food, an activity status, and the like, for example. That is to say, in this embodiment, for example, a gut movement score, a gut state score, an excretion score, a drink score, a food score, an activity status score, and the like are used as the element scores. The scores are numerical values representing the state or degree of goodness of a matter of interest, symbols indicating a grade, or the like, and is information easily understandable for users.

The gut-related score acquiring unit 2152 acquires a gut state score regarding a bowel movement state (normal, diarrhea, constipation, etc) and a gut movement score regarding peristalsis movements (frequency, etc.) of the guts, using the sound information acquired by the sound information acquiring unit 2141 and learning information. In this embodiment, the gut-related score acquiring unit 2152 inputs the sound information acquired by the sound information acquiring unit 2141 to the learning information using a machine learning method, thereby acquiring an output indicator value. Then, the gut-related scores (a gut state score and a gut movement score) are acquired based on the output indicator value.

In this embodiment as well, the sound information used in the processing unit 2240 may be a spectrogram or other sound data or the like. The processing unit 2240 may also be configured to use learning input information containing user information such as basic information, in accordance with generation and use of the learning information. It is sufficient that the gut-related score acquiring unit 2152 is configured to acquire learning information of a type corresponding to an identifier specified based on the user information, from the learning information storage unit 2111, and acquire a gut-related score using the learning information. Accordingly, more accurate output results can be obtained.

The excretion score acquiring unit 2153 acquires an excretion score based on the excretion-related information.

The eating-and-drinking score acquiring unit 2154 acquires a drink score and a food score based on the eating-and-drinking information.

The activity status score acquiring unit 2155 acquires an activity status score based on the activity status information.

These units of the element score acquiring unit 2151 acquire element scores based on output indicator values or various types of life information, according to whether or not an output indicator value or the content of various types of life information satisfies a predetermined condition, for example. The predetermined condition may be set for each element and for each viewpoint of the element. For example, an element score can be acquired by reflecting a first predetermined point in the element score if a predetermined condition is satisfied or by reflecting a second predetermined point in the element score if the predetermined condition is not satisfied. Specifically, for example, in the case in which the frequency of gut sounds is obtained as an output, indicator value, if the frequency of the gut sounds is within a predetermined range, a first, predetermined point may be added to a gut movement score serving as the base, or otherwise a second predetermined point may be subtracted from the gut movement score serving as the base.

The constituent units of the element score acquiring unit 2151 accumulate each acquired element score in the user information storage unit 2115 in association with a user identifier.

The constituent units of the element score acquiring unit 2151 may compare an output, indicator value or the content of various types of life information with a predetermined reference, and calculate an element score by using a predetermined calculation formula according to the comparison result. Also, multiple threshold values serving as a reference may be prepared, and a predetermined point corresponding to a condition range that an output indicator value or the content of various types of life information matches may be reflected in the element score. Also, multiple evaluation viewpoints (viewpoints for comparison with a reference value, etc.) may be provided for each element such as an intestinal movement, a gut state, excretion, drink, food, or an activity status, and a predetermined point may be reflected in the element score according to a result of comparison with a reference value for each viewpoint. The corresponding point may be reflected in the element score based on information (e.g., an n-dimensional look-up table) that maps the points to be reflected, in advance, in a space composed of multiple viewpoint axes.

The constituent units of the element score acquiring unit 2151 may acquire an element score based on element scores acquired in the past for the user and stored in the user information storage unit 2115, output indicator values or various types of life information in the past, or the like. For example, it is also possible to acquire a current element score by reflecting a current point in a previously acquired element score. It is also possible to acquire an element score using an average value or the like of output indicator values or various types of life information in a past predetermined period and current output indicator values or various types of life information. It is also possible to acquire an element score using points (by adding the points, etc.) respectively specified for a predetermined number of past output indicator values or various types of life information and current output indicator values or various types of life information.

The constituent units of the element score acquiring unit 2151 may set factors such as conditions set for acquiring such element scores, a reference value for use in comparison, an element score serving as the base, a point that is to be reflected in the element score, and a method for reflecting a point in the element score (addition, subtraction, multiplication, etc.) as appropriate based on the user's basic information. That is to say, the constituent units of the element score acquiring unit 2151 may acquire an element score based on the user's basic information. Specifically, for example, the constituent units of the element score acquiring unit 2151 may be configured to acquire an element score by applying different factors according to the user's sex and age.

In this embodiment, the gut score acquiring unit 2149 acquires a gut score using the gut movement score and the gut state score acquired by the gut-related score acquiring unit 2152 in this manner, the excretion score acquired by the excretion score acquiring unit 2153, the drink score and the food score acquired by the eating-and-drinking score acquiring unit 2164, and the activity status score acquired by the activity status score acquiring unit 2155. The gut score may be acquired by applying element scores to a predetermined calculation formula and performing calculation using a predetermined method such as addition or multiplication, for example. The gut score may be acquired by using a learning model configured using a machine learning method such that element scores are taken as input and a gut score is taken as output, for example. The element scores may be normalized or otherwise used to obtain a gut score, as necessary.

The gut score acquiring unit 2149 accumulates the acquired gut score in the user information storage unit 2115 in association with a user identifier.

The gut score acquiring unit 2149 may acquire a current gut score based on gut scores acquired in the past for the user and stored in the user information storage unit 2115. For example, it is also possible to acquire a current gut score by reflecting a point according to the current element scores in a score serving as the base based on the previous gut score.

The gut score output unit 2161 outputs the gut score acquired by the gut score acquiring unit 2149. In this embodiment, the gut score output unit 2161 outputs information such as a gut score by transmitting it to the terminal apparatus 2600, for example, but there is no limitation to this. For example, the output may be performed by displaying the gut score in text or images on a display screen included in the information processing apparatus 2100.

In this embodiment, the task acquiring unit 2262 acquires a task based on the gut-related score acquired by the gut score acquiring unit 2149 using the learning information. The task acquiring unit 2262 may be configured to acquire a task based not only on the gut-related score but also on the gut score, other elements scores, or the like.

If a value (score) of a predetermined indicator acquired using the learning information satisfies a selection condition, the task acquiring unit 2162 acquires a task corresponding to the selection condition. That is to say, in this embodiment, selection conditions regarding a value of the predetermined indicator are set in advance respectively for two or more tasks. The selection conditions mean that the relationship between the threshold value and the value of an indicator is in a predetermined state, for example. The predetermined state means, but not limited to, that the relationship is indicated by a predetermined function, such as being large, small, equal, or a predetermined ratio, for example. For example, for the task of receiving a massage with a predetermined content, a condition that the number of peristalsis movements per unit time is less than or equal to a predetermined value, or the like may be set as the selection condition for peristalsis movements of the guts, for example. The correspondence between such selection conditions and tasks may be stored as the task association information in the task storage unit 2118, for example, but there is no limitation to this.

FIG. 30 is a diagram showing an example of task association information for use in the information processing apparatus 2200 in the embodiment.

As shown in FIG. 30, in the task association information, for example, a selection condition and a task identifier for identifying a task are associated with each other. As with Embodiment 2, the task association information further contains the name of the task, a description of the task, a product identifier for identifying a product related to the task, and the like corresponding to the task identifier. The task association information is not limited to this, and may further contain attribute values of other attributes or may not contain any of the attribute values mentioned above.

Conditions regarding whether or not a result of a comparison between a score and a threshold value is in a predetermined state, such as that the gut state score is less than a threshold value X1, the gut movement score is less than threshold value X2, or the like, are set as the selection condition, for example. Values different from scores, such as that the gut state is not good, the peristalsis movements of the guts are poor, or the like, may be used as the selection condition. In this case, for example, it is sufficient that the task acquiring unit 2262 acquires a determination result regarding the gut state or the peristalsis movements of the guts, and determines whether or not the determination result satisfies the selection condition.

In this embodiment, the information processing apparatus 2200 performs various operations as follows, for example. These operations are performed by the processing unit 2240 executing control operations and the like while using the constituent units.

Figure 31:
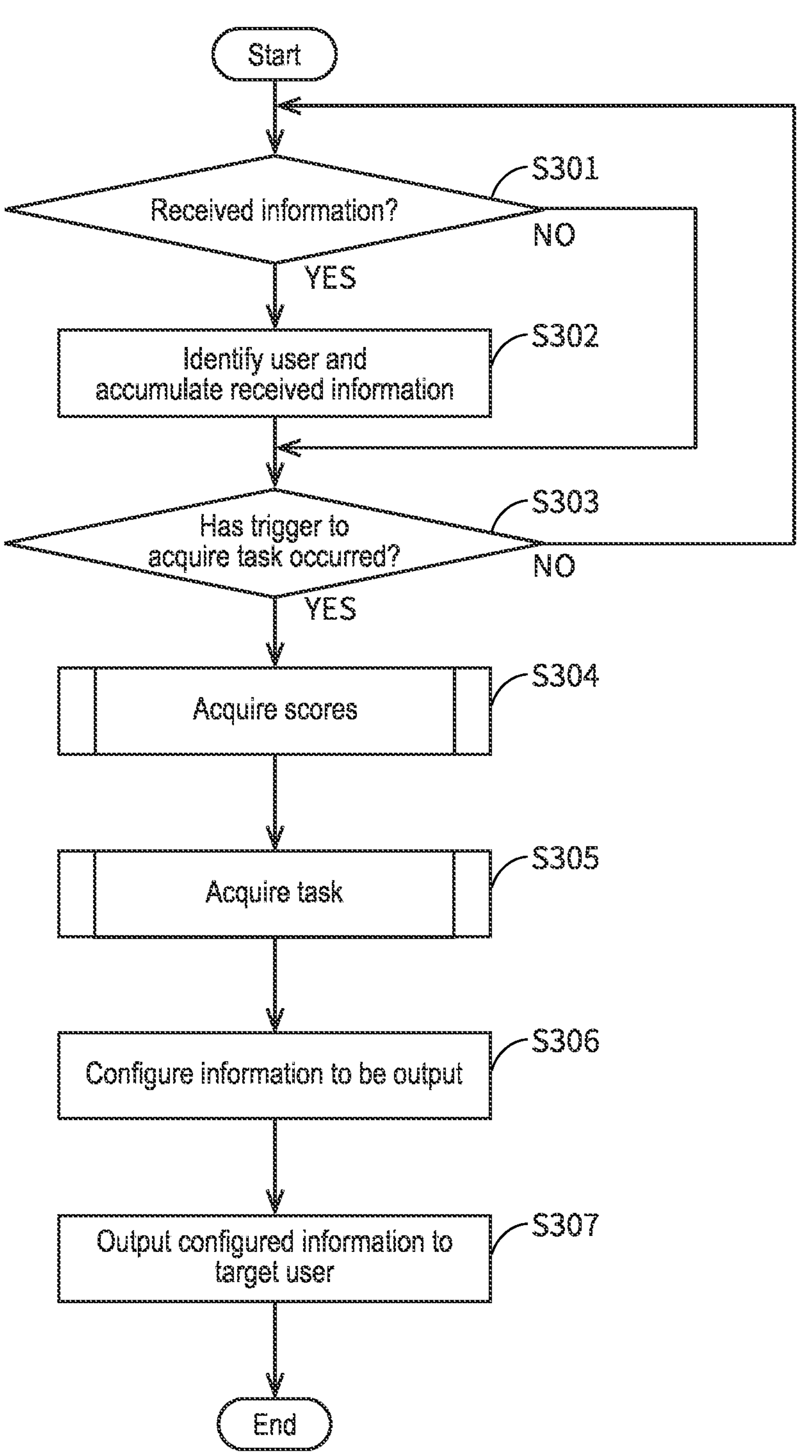
FIG. 31 is a flowchart showing an example of an operation of the information processing apparatus in the embodiment.

FIG. 31 is a flowchart showing an example of an operation of the information processing apparatus 2200 in the embodiment.

The processing of steps S301 to S303 is similar to that of steps S201 to S203 in Embodiment 2 above. The task acquiring unit 2262 accumulates various types of information in the user information storage unit 2115 or the like based on a user identifier of the user. If a trigger to acquire a task has occurred, the procedure of the task acquiring unit 2262 advances to the next processing.

(Step S304) The processing unit 2240 causes the gut score acquiring unit 2149 to perform score acquiring processing. The score acquiring processing will be described later. Through the score acquiring processing, the information on a task of the user is acquired and accumulated in the user information storage unit 2115.

(Step S306) The processing unit 2240 causes the task acquiring unit 2262 to perform task acquiring processing. The task acquiring processing will be described later.

Through the task acquiring processing, information on a task of the user is acquired and accumulated in the user information storage unit 2115.

Figure 32:
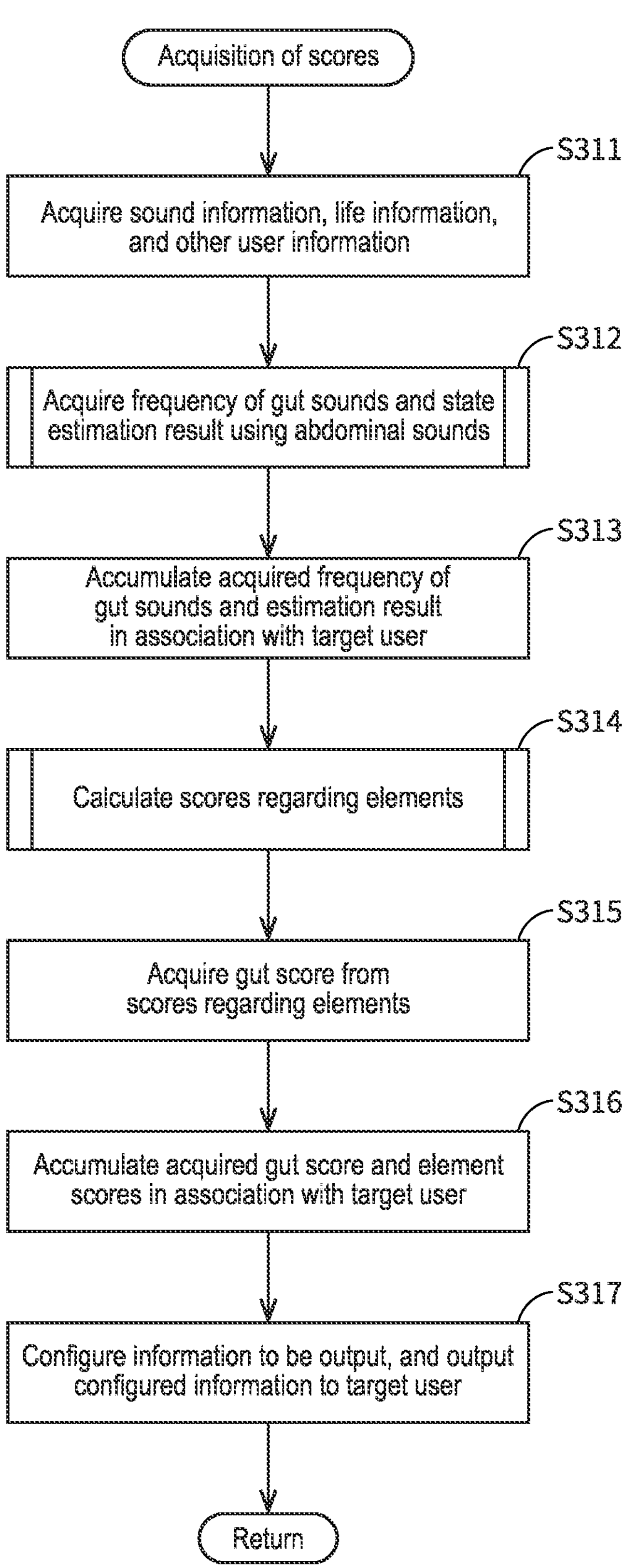
FIG. 32 is a flowchart showing an example of score acquiring processing of the information processing apparatus in the embodiment.

The processing of steps S306 and S307 is similar to that of steps S205 and S206 in Embodiment 2 above, FIG. 32 is a flowchart showing an example of the score acquiring processing of the information processing apparatus 2200 in the embodiment.

(Step S311) The gut score acquiring unit 2149 acquires sound information, life information, past user information, and the like regarding a target user from the user information storage unit 2115 based on the user identifier of the user. It is also possible to acquire basic information.

(Step S312) The gut score acquiring unit 2149 performs processing for acquiring the frequency of gut sounds and a gut state estimation result using the sound information. Hereinafter, this processing may be referred to as abdominal sound usage processing. The abdominal sound usage processing is performed in the same way to that of Embodiment 1, for example. That is to say, the processing similar to that in Embodiment 1 in which the score acquiring unit 149 outputs the value of the output indicator, using the learning information for sound information stored in from the learning information storage unit 111 is performed by the gut score acquiring unit 2149 using the learning information stored in the learning information storage unit 2111. In the case in which the sound information stored in the user information storage unit 2115 is a spectrogram such as the case in which the sound information transmitted from the terminal apparatus 2600 is a spectrogram, it is sufficient that the processing in which the gut score acquiring unit 2149 generates a spectrogram is not performed.

(Step S313) The gut score acquiring unit 2149 accumulates information such as the acquired frequency of gut sounds and gut state estimation result, in the user information storage unit 2115 in association with the user identifier of the target user.

(Step 9314) The gut score acquiring unit 2149 causes the element score acquiring unit 2151 to perform processing for acquiring a score regarding each element. Hereinafter, this processing may be referred to as element score acquiring processing. In this embodiment, gut-related score acquiring processing, excretion score acquiring processing, food score acquiring processing, drink score acquiring processing, and activity status score acquiring processing are performed as the element score acquiring processing.

Each element score acquiring processing is performed in the same way to that of Embodiment 1, for example. That is to say, as with the processing performed by the element score acquiring unit 151 in Embodiment 1, the element score acquiring unit 2151 acquires the element scores. For example, element scores may be acquired through addition of a predetermined point to or subtraction of a predetermined point from scores, according to determination results regarding the frequency of gut sounds, a gut state estimation result the shape, amount, and odor of excrement, the time, amount, and content of meals, or the like. The base point of the element scores may be a predetermined point or may be set based on past history or other factors. For example, a previously acquired element score may be set as the current base point. Alternatively, a value (e.g., an average value, etc.) obtained through calculation based on information on past element scores in a predetermined period may be set as the base point.

(Step S315) When the element scores are obtained, the gut score acquiring unit 2149 acquires a gut score from the element scores. At this time, the gut score acquiring unit 2149 acquires a gut score using a predetermined method such as addition or multiplication of the element scores as described above, for example, but there is no limitation to this.

(Step S316) The gut score acquiring unit 2149 accumulates the acquired gut score and element scores in the user information storage unit 2115 in association with the user identifier of the target user. Subsequently, the procedure returns to the processing in FIG. 31.

Figure 33:
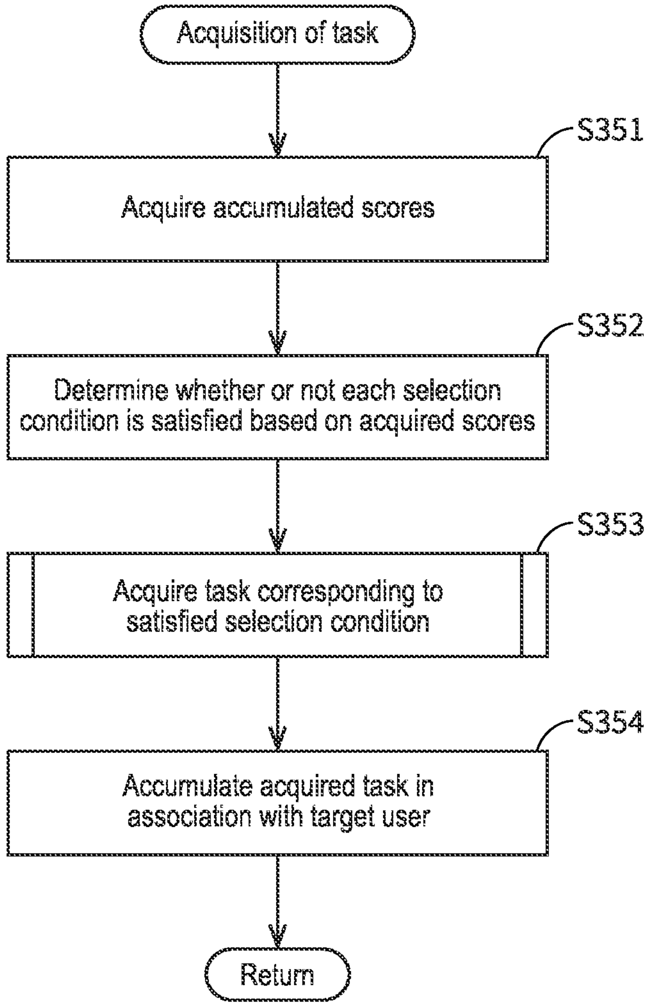
FIG. 33 is a flowchart showing an example of task acquiring processing of the information processing apparatus in the embodiment.

FIG. 33 is a flowchart showing an example of the task acquiring processing of the information processing apparatus 2200 in the embodiment.

(Step S351) The task acquiring unit 2262 acquires a gut score and element scores associated with a user identifier of the target user, from the user information storage unit 2115.

(Step S352) The task acquiring unit 2262 determines whether or not each selection condition contained in the task association information is satisfied, based on the acquired scores.

(Step S353) The task acquiring unit 2262 acquires a task corresponding to the selection condition that has been determined as being satisfied (this processing is referred to as corresponding task acquiring processing). It is sufficient that the corresponding task acquiring processing is performed in the same way as that in Embodiment 2, for example, but there is no limitation to this. For example, it is also possible that all tasks corresponding to the selection condition that has been determined as being satisfied are acquired.

(Step S354) The task acquiring unit 2262 accumulates the acquired task in the user information storage unit 2115 in association with a user identifier of the target user. Subsequently, the procedure returns to the processing in FIG. 31.

As explained above, in Embodiment 3 as well, the information processing apparatus 2200 may acquire one or more tasks corresponding to the user, using the learning information and the sound information stored in the storage unit 2110, and output information on the acquired tasks. Thus, as with Embodiment 2, the user can easily learn about objectively selected tasks suitable for him or her. In this embodiment, since the tasks corresponding to the score are output, the user can easily learn about information on the tasks corresponding to the value reflecting the activity state of the guts of the user.

In this embodiment, in accordance with the task output unit 2168 outputting a task, the gut score output unit 2161 may output, information indicating scores acquired as described above and stored in the user information storage unit 2115. The user may be able to check both the task and the score using the terminal apparatus 200, and thus the user is effectively motivated to execute the task while being aware of the score indicating the gut condition and being aware of the task.

Description of Modified Examples of Embodiment 3

The processing regarding the acquisition of a score is not limited to that described above. For example, the extraction of the frequency of gut sounds and the estimation of the gut state may be performed using learning information configured using mutually different pieces of input information. Specifically, for example, it is possible to output the frequency of gut sounds using learning information configured using a machine learning in which sound information is taken as input and sound information corresponding to the portion of abdominal sounds is taken as output, and to output a gut state estimation result using learning information configured using a machine learning in which predetermined life information (e.g., excretion information, eating-and-drinking information, etc.) in addition to the sound information is taken as input and a gut state estimation result, is taken as output. This allows each output result to be obtained with greater accuracy.

Furthermore, for example, learning information that is to be used may be selected based on life information. In this case, the learning information stored in the learning information storage unit 2111 may be associated with one or more elements and one or more viewpoints that may be contained in the life information, and, in the abdominal sound usage processing, learning information that is to be used may be selected based on the one or more elements and the one or more viewpoints in the life information. If the abdominal sound usage processing is performed in this manner, the frequency of gut sounds and the gut state estimation result can be obtained with greater accuracy.

Furthermore, for example, the gut-related score acquiring unit 2162 may acquire a gut-related score from sound information and life information, using learning information configured such that sound information and life information are taken as input and a gut-related score is taken as output. In this case, any element or viewpoint in the life information may be used as input information. It is also possible to acquire a gut-related score without using the life information. In either case, the basic information may be used as input information. The learning information that is used may be generated by the learning information generating unit 2147, using two or more pairs of learning input information containing sound information and life information and a gut-related score, through configuration of a classifier using the two or more pairs of information and a module for configuring a machine learning classifier, or may be generated by another apparatus or the like in the same manner. For example, if a sufficient number of pairs of learning input information and a gut-related score are available, a gut-related score and a gut score can be obtained easily and with high accuracy by directly outputting the gut-related score using the learning information generated using the information on these combinations.

If a large number of pairs of learning input information and a gut score are available, learning information in which a gut score is taken as output information may be configured using a machine learning method using these pieces of information. In this case, the gut score acquiring unit 2149 may input sound information and another type of input information (life information, basic information, etc.) to the learning information, thereby acquiring a gut score. Accordingly, a gut score can be obtained easily and with high accuracy.

The processing in Embodiments 2 and 3 above may be realized by software. The software may be distributed by software downloads or any other suitable method. Furthermore, the software may be distributed in a form where the software is stored in a recording medium such as a CD-ROM. The software that realizes the information processing apparatus in the foregoing embodiments is the following sort of program. Specifically, this program is a program for causing a computer to function as: a sound information acquiring unit that acquires sound information regarding abdominal sounds, which are sounds emanating from the abdomen, of a user; a task acquiring unit that acquires one or more tasks corresponding to the user, using input information containing the sound information acquired by the sound information acquiring unit and learning information prepared in advance; and a task output unit that outputs in-formation on the tasks acquired by the task acquiring unit.

The terminal apparatuses may each have part or the whole of the configuration for realizing the functions related to the acquisition and output of tasks as those of the information processing apparatus described above.

Figure 34:
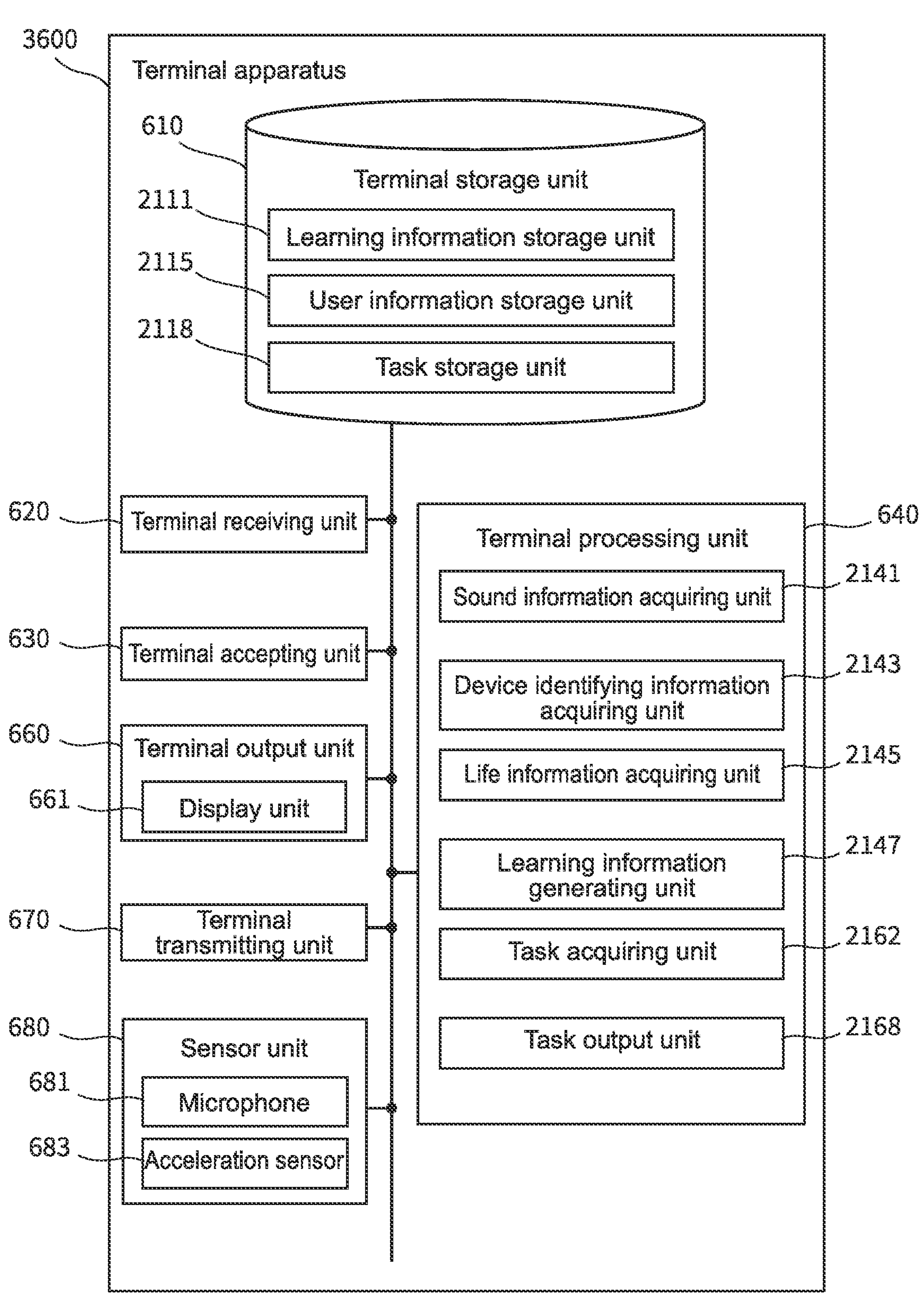
FIG. 34 is a block diagram showing the configuration of the terminal apparatus according to another modified example of Embodiment 2 above.

FIG. 34 is a block diagram showing the configuration of the terminal apparatus according to another modified example of Embodiment 2 above.

In FIG. 34, the constituent elements similar to those of the configuration in Embodiment 2 above are denoted by the same reference numerals. A terminal apparatus 3600 is configured to be capable of acquiring and outputting gut scores as with the information processing apparatus 2100 described above.

As shown in FIG. 34, in the terminal apparatus 3600, the terminal storage unit 610 includes the learning information storage unit 2111, the user information storage unit 2115, and the task storage unit 2118. The terminal processing unit 640 includes the sound information acquiring unit 2141, the device identifying information acquiring unit 2143, the life information acquiring unit 2145, the learning information generating unit 2147, the task acquiring unit 2162, and the task output unit 2168. The sound information acquiring unit 2141 can acquire sound information based on the abdominal sounds recorded using the microphone 681. The device identifying information acquiring unit 2143 acquires device identifying information on the terminal apparatus 3600. The life information acquiring unit 2145 acquires life information based on information input by the user and accepted by the terminal accepting unit 630 or information acquired using the sensor unit 680.

In this manner, the terminal apparatus 3600 may be configured to function as an information processing apparatus that acquires and outputs tasks. The same effect as described above can be obtained.

With respect to the acquisition and output of tasks, some functions and roles of the terminal apparatus 3600 may be performed or implemented by the information processing apparatus 2100 or the like. For example, it is also possible to employ a configuration in which the learning information generating unit 2147 is provided in the information processing apparatus 2100 and the generated learning information is received and used by the terminal apparatus 3600. For example, it is also possible to employ a configuration in which the learning information storage unit 2111 in which multiple pieces of learning information are stored is provided in the information processing apparatus 2100 and, out of these pieces of learning information, learning information corresponding to the device identifying information and the like of the terminal apparatus 3600 is downloaded to and used by the terminal apparatus 3600.

Conventionally, knowledge of what so-called healthy activities are and what so-called unhealthy activities are known. Then, tasks related to such activities are set, for each user, and each user is encouraged to work on such tasks in order to, for example, maintain or improve his or her health state. However, since the health state of each user varies, it is not always possible for all users to achieve the expected effect when multiple users work on a task. In other words, each user may have a different task that is suitable for him or her to perform.

As described above, the information processing apparatuses according to Embodiments 2 and 3 make it possible to output information on tasks suitable for the user, thus rendering the apparatuses useful as an information processing apparatus and the like.

Aspects

It will be understood by those skilled in the art that Embodiments 2 and 3 given above as an example is a specific example of the following aspects.

A first aspect is directed to an information processing apparatus including: a sound information acquiring unit that acquires sound information regarding living body sounds which are sounds emanating from a living body, of a user; a task acquiring unit that acquires one or more tasks corresponding to the user, using input information containing the sound information acquired by the sound information acquiring unit and learning information prepared in advance; and a task output unit that outputs information on the tasks acquired by the task acquiring unit By utilizing this configuration, it is possible to output information on one or more tasks suitable for the user.

Furthermore, a second aspect of the present invention is directed to the information processing apparatus according to the first aspect, wherein the learning information is information configured using two or more pieces of training data having input information containing the sound information and output information containing a task identifier for identifying a task for improving a body condition.

By utilizing this configuration, it is possible to output information on a task for improving a user's body condition.

Furthermore, a third aspect of the present invention is directed to the information processing apparatus according to the first aspect, wherein the learning information is information configured using two or more pieces of training data having input information containing the sound information and output information containing an issue identifier for identifying an issue regarding a body condition, and the task acquiring unit acquires the issue identifier by applying the input information containing the sound information acquired by the sound information acquiring unit to the learning information, and acquires a task using the acquired issue identifier.

By utilizing this configuration, it is possible to output information on a task corresponding to an issue regarding a user's body condition.

Furthermore, a fourth aspect of the present invention is directed to the information processing apparatus according to the third aspect, further including: a task storage unit in which two or more pairs each constituted by one issue identifier and one or more tasks in association with each other are stored, wherein the task acquiring unit acquires a task stored in the task storage unit and corresponding to an issue identifier acquired using the learning information.

By utilizing this configuration, it is possible to output information on a task corresponding to an issue regarding a user's body condition.

Furthermore, a fifth aspect of the present invention is directed to the information processing apparatus according to the first aspect, wherein the task acquiring unit acquires a value of a predetermined indicator regarding a health state based on output information acquired by applying the input information containing the sound information acquired by the sound information acquiring unit to the learning information, and acquires a task using the acquired value of the predetermined indicator.

By utilizing this configuration, it is possible to output information on a task corresponding to a value of a predetermined indicator regarding the health state of the user.

Furthermore, a sixth aspect of the present invention is directed to the information processing apparatus according to the fifth aspect, wherein the living body sounds are abdominal sounds emanating from the abdomen, and the predetermined indicator is at least one of a bowel movement state, the number of peristalsis movements of guts per unit time, and the frequency of abdominal sounds.

By utilizing this configuration, it is possible to output information on a task corresponding to a value reflecting the activity state of the guts of the user.

Furthermore, a seventh aspect of the present invention is directed to the information processing apparatus according to the fifth or sixth aspect, wherein selection conditions regarding a value of the predetermined indicator are set in advance respectively for two or more tasks, and in a case in which a value of the predetermined indicator acquired using the learning information satisfies a selection condition, the task acquiring unit acquires a task corresponding to the selection condition.

By utilizing this configuration, it is possible to output information on a task corresponding to a value of a predetermined indicator regarding the health state of the user.

Furthermore, an eighth aspect of the present invention is directed to the information processing apparatus according to any one of the first to seventh aspects, wherein, in a case in which two or more tasks are candidates for acquisition, the task acquiring unit acquires information on one task specified at random out of the two or more tasks.

By utilizing this configuration, it is possible to output information on one task to the user.

Furthermore, a ninth aspect of the present invention is directed to the information processing apparatus according to any one of the first to eighth aspects, wherein the task acquiring unit acquires a task identifier for identifying a task currently applied for a user, and acquires one or more tasks corresponding to the user based on the acquired task identifier.

By utilizing this configuration, it is possible to output information on a task based on a currently applied task.

Furthermore, a tenth aspect of the present invention is directed to the information processing apparatus according to the ninth aspect, the task acquiring unit acquires a task different from a task currently applied for a user.

By utilizing this configuration, it is possible to output information on a task different from a currently applied task.

Furthermore, an eleventh aspect of the present invention is directed to the information processing apparatus according to any one of the first to tenth aspects, further including: a device identifying information acquiring unit that acquires device identifying information for identifying the type of device used to acquire living body sounds corresponding to the sound information, wherein multiple pieces of learning information are prepared respectively in association with pieces of device identifying information, and the task acquiring unit acquires a task using the learning information corresponding to the device identifying information acquired by the device identifying information acquiring unit.

By utilizing this configuration, it is possible to acquire a suitable task according to the properties and the like of a device used for acquiring living body sounds.

Furthermore, a twelfth aspect of the present invention is directed to the information processing apparatus according to any one of the first to eleventh aspects, further including: a microphone for recording the living body sounds; and a display unit that displays the task output by the task output unit.

By utilizing this configuration, it is possible for the user to check the task displayed based on the living body sounds recorded using the microphone.

Furthermore, a thirteenth aspect of the present invention is directed to the information processing apparatus according to the twelfth aspect, further including a learning information storage unit in which the learning information is stored, wherein the task acquiring unit acquires one or more tasks by applying input information containing sound information from the living body sounds recorded by the microphone to the learning information, and the task output unit displays the tasks on the display unit.

By utilizing this configuration, it is possible for the user to check the task displayed based on the living body sounds recorded using the microphone, without communication or the like with other apparatuses.

Others

Figure 35:
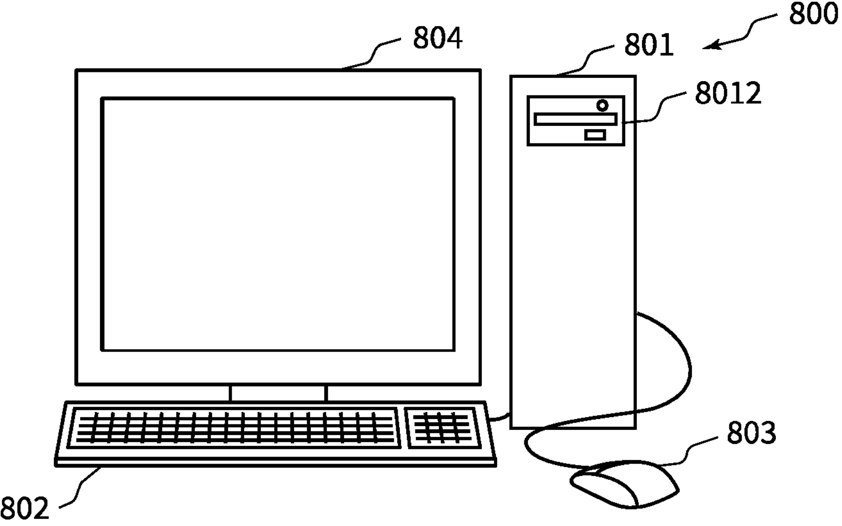
FIG. 35 is a schematic view of a computer system in the embodiments.
Figure 36:
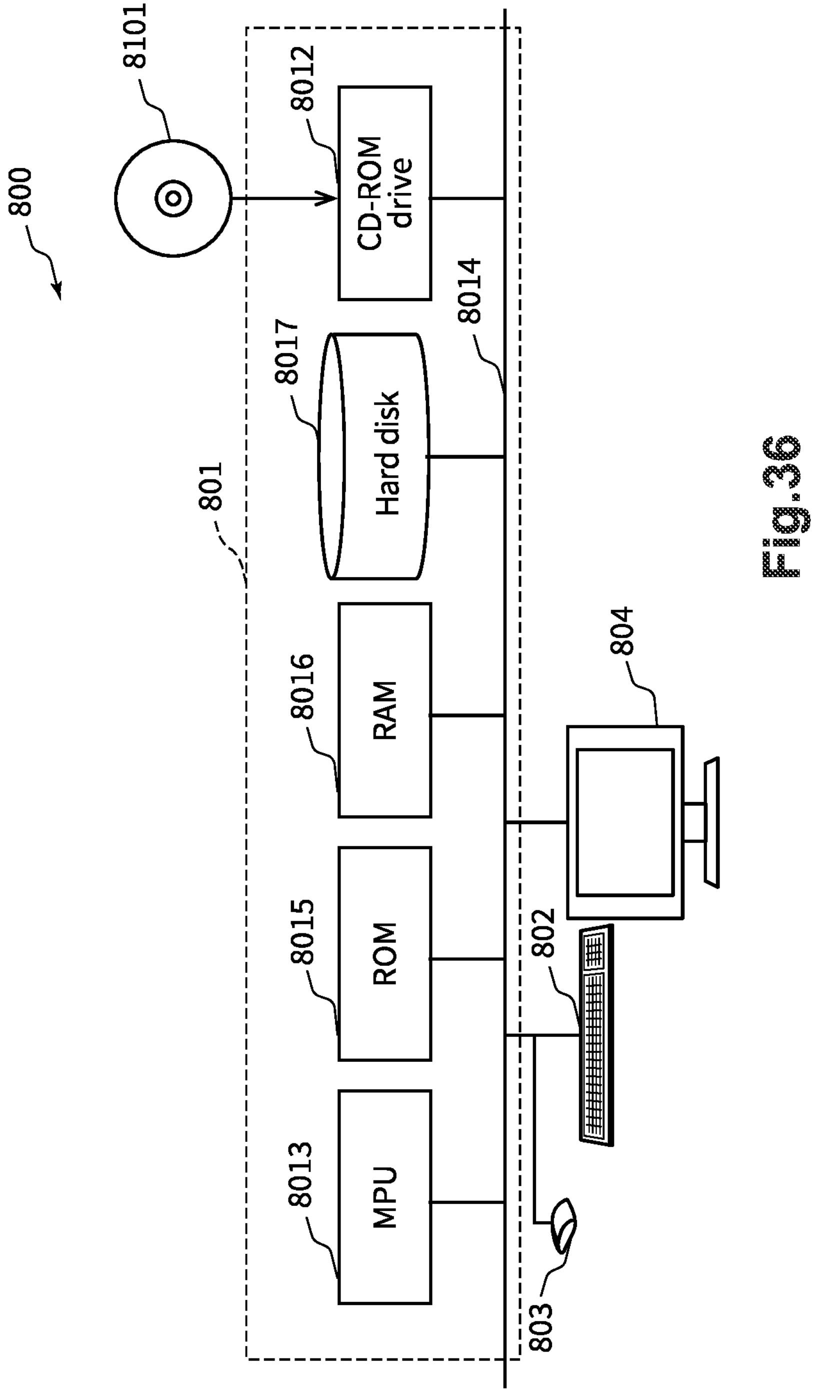
FIG. 36 is a block diagram of the computer system in the embodiments.

FIG. 35 is a schematic view of a computer system 800 in the foregoing embodiments. FIG. 36 is a block diagram of the computer system 800 in the embodiments.

These drawings show the configuration of a computer that executes the program described in this specification to realize the information processing apparatus and the like in the embodiments described above. The foregoing embodiments may be realized using computer hardware and a computer program executed thereon.

The computer system 800 includes a computer 801 including a CD-ROM drive, a keyboard 802, a mouse 803, and a monitor 804.

The computer 801 includes, in addition to the CD-ROM drive 8012, an MPU 8013, a bus 8014 connected to the CD-ROM drive 8012 or equivalent, a ROM 8015 in which a program such as a boot up program is stored, a RAM 8016 that is connected to the MPU 8013 and is a memory in which a command of an application program is temporarily stored and a temporary storage area is provided, and a hard disk 8017 in which an application program, a system program, and data are stored. Although not shown, the computer 801 may further include a network card that provides connection to a LAN.

The program for causing the computer system 800 to execute the functions of the information processing apparatus and the like in the foregoing embodiments may be stored in a CD-ROM 8101 that is inserted into the CD-ROM drive 8012, and be transmitted to the hard disk 8017. Alternatively, the program may be transmitted via a network (not shown) to the computer 801 and stored in the hard disk 8017. At the time of execution, the program is loaded into the RAM 8016. The program may be loaded from the CD-ROM 8101. Alternately, the program may be loaded directly from a network.

The program does not necessarily have to include, for example, an operating system (OS) or a third party program to cause the computer 801 to execute the functions of the information processing apparatus and the like in the foregoing embodiments. The program may only include a command portion to call an appropriate function (module) in a controlled mode and obtain desired results. The manner in which the computer system 800 operates is well known, and thus a detailed description thereof has been omitted.

It should be noted that, in the program, in a transmitting step of transmitting information, a receiving step of receiving information, or the like, processing that is performed only by hardware is not included. For example, processing performed by a modem or an interface card in the transmitting step (processing that can be performed only by hardware) is not included.

Furthermore, the computer that executes the program may constituted by a single computer, or constituted by multiple computers. That is to say, centralized processing may be performed, or distributed processing may be performed, respectively.

Furthermore, in the foregoing embodiments, two or more constituent elements in one apparatus may be physically realized by one medium.

Furthermore, in the foregoing embodiments, each constituent element may be configured by dedicated hardware, or alternatively, constituent elements that can be realized by software may be realized by executing a program. For example, each constituent element may be realized by a program execution unit such as a CPU reading and executing a software program stored in a recording medium such as a hard disk or a semiconductor memory. At the time of executing the program, the program execution unit may execute the program while accessing the storage unit or the recording medium. Furthermore, this program may be executed by downloading from a server or the like, or may be executed by reading a program stored in a predetermined recording medium (e.g., an optical disk, a magnetic disk, a semiconductor memory, etc.). Furthermore, the program may be used as a program for constituting a program product. Furthermore, a computer that executes the program may be a single computer or may be multiple computers. That is to say, centralized processing may be performed, or distributed processing may be performed.

In the foregoing embodiments, each process (function) may be realized as centralized processing using a single apparatus (system), or may be realized as distributed processing using multiple apparatuses (in this case, the entire system constituted by multiple apparatuses that perform distributed processing may be regarded as one "apparatus"). For example, some of the operations that are described in the foregoing embodiments as being performed by the information processing apparatus may be performed by another apparatus such as a terminal apparatus.

Furthermore, in the foregoing embodiments, information transmission performed between constituent elements may be such that, for example, if two constituent elements for transmitting information are physically different from each other, the transmission is performed by one of the constituent elements outputting the information and the other constituent element accepting the information, or alternatively, if two constituent elements for transmitting information are physically the same, the transmission is performed by shifting from a processing phase corresponding to one of the constituent elements to a processing phase corresponding to the other constituent element.

Furthermore, in the foregoing embodiments, information related to the processing that is performed by each constituent element, for example, information that is to be accepted, acquired, selected, generated, transmitted, or received by each constituent element, information such as a threshold value, a numerical expression, or an address used by each constituent element in the processing and the like may be retained in an unshown recording medium temporarily or for a long period of time even if not specified in the description above. Furthermore, the information may be accumulated in the unshown recording medium by each constituent element or by an unshown accumulating unit. Furthermore, the information may be read from the unshown recording medium by each constituent element or by an unshown reading unit.

Furthermore, in the foregoing embodiments, if information used by each constituent element or the like, for example, information such as a threshold value, an address, or various setting values used by each constituent element in the processing may be changed by a user, the user may be or may not be allowed to change such information as appropriate even if not specified in the description above. If the user is allowed to change such information, the change may be realized by, for example, an unshown accepting unit that accepts a change instruction from the user and an unshown changing unit that changes information according to the change instruction. The unshown accepting unit may accept the change instruction, for example, by accepting information from an input device, by receiving information transmitted via a communication line, or by accepting information read from a predetermined recording medium.

The present invention is not limited to the embodiments set forth herein. Various modifications are possible within the scope of the invention. The configuration is not limited that described in the foregoing embodiments, and some of the constituent elements and functions of the embodiments may be omitted.

In Embodiment 2 above, abdominal sounds are used as living body sounds, but other living body sounds may be used. For example, a combination of multiple living body sounds such as a combination of abdominal sounds and other living body sounds may be used. Then, a task for improving a body condition may be output. In this case, sound information may be used to acquire an issue identifier of an issue regarding the body, and the issue identifier may be used to acquire a task. Also, sound information may be used to acquire a value of a predetermined indicator regarding a health state, and the acquired value may be used to acquire a task. For example, the sound information of heart sounds may be used to output information on a task related to arrhythmia or valvular heart disease according to the sound interval, presence of noise, or the like. For example, the sound information of breath sounds may be used to output information on a task related to pneumonia, asthma, or the like according to the type of noise, or to suggest an appropriate exercise load and output information on a task corresponding thereto according to the acquired lung capacity or the like. For example, the sound information related to blood flow, such as neck sounds, leg sounds, and tinnitus sounds, may be used to suggest a task with an appropriate exercise load. Also, the sound information on swallowing sounds may be used to output a task to take appropriate thickened food from the viewpoint of preventing aspiration. For example, the sound of a drink as it passes down the throat may be used to output a task to consume a drink with an appropriate carbonation (strength of gas pressure).

INDUSTRIAL APPLICABILITY

As described above, the information processing apparatus according to the present invention makes it possible to output information regarding user's health, thus rendering this apparatus useful as an information processing apparatus and the like.

The invention claimed is:

1. An information processing apparatus comprising a processor, wherein the processor acquires sound information regarding living body sounds, which are sounds emanating from a living body, of a user;

the processor acquires one or more tasks corresponding to the user, using input information containing the sound information acquired by the processor and learning information prepared in advance;

the processor outputs information on the tasks acquired by the processor; and the processor acquires device identifying information for identifying the type of device used to acquire living body sounds corresponding to the sound information, wherein multiple pieces of learning information are prepared respectively in association with pieces of device identifying information, and the processor acquires a task using the learning information corresponding to the device identifying information acquired by the processor, wherein the information processing apparatus is configured to acquire a suitable task according to properties of a device used for acquiring the living body sounds, wherein the processor generates a spectrogram based on sound data, the sound data is obtained by recording abdominal sounds, and the spectrogram is the sound information and an input to the processor, and wherein the processor uses machine learning.

2. The information processing apparatus according to claim 1, wherein the learning information is information configured using two or more pieces of training data having input information containing the sound information and output information containing a task identifier for identifying a task for improving a body condition.

3. The information processing apparatus according to claim 1, wherein the learning information is information configured using two or more pieces of training data having input information containing the sound information and output information containing an issue identifier for identifying an issue regarding a body condition, and the processor acquires the issue identifier by applying the input information containing the sound information acquired by the processor to the learning information, and acquires a task using the acquired issue identifier.

4. The information processing apparatus according to claim 3, further comprising:

a memory in which two or more pairs each constituted by one issue identifier and one or more tasks in association with each other are stored, wherein the processor acquires a task stored in the memory and corresponding to an issue identifier acquired using the learning information.

5. The information processing apparatus according to claim 1, wherein the processor acquires a value of a predetermined indicator regarding a health state based on output information acquired by applying the input information containing the sound information acquired by the processor to the learning information, and acquires a task using the acquired value of the predetermined indicator.

6. The information processing apparatus according to claim 5, wherein the living body sounds are abdominal sounds emanating from the abdomen, and the predetermined indicator is at least one of a bowel movement state, the number of peristalsis movements of guts per unit time, and the frequency of abdominal sounds.

7. The information processing apparatus according to claim 5, wherein selection conditions regarding a value of the predetermined indicator are set in advance respectively for two or more tasks, and in a case in which a value of the predetermined indicator acquired using the learning information satisfies a selection condition, the processor acquires a task corresponding to the selection condition.

8. The information processing apparatus according to claim 1, wherein, in a case in which two or more tasks are candidates for acquisition, the processor acquires information on one task specified at random out of the two or more tasks.

9. The information processing apparatus according to claim 1, wherein the processor acquires a task identifier for identifying a task currently applied for a user, and acquires one or more tasks corresponding to the user based on the acquired task identifier.

10. The information processing apparatus according to claim 9, wherein the processor acquires a task different from a task currently applied for a user.

11. The information processing apparatus according to claim 1, further comprising:

a microphone for recording the living body sounds; and a display device that displays the task output by the processor.

12. The information processing apparatus according to claim 11, further comprising a learning information storage unit in which the learning information is stored, wherein the processor acquires one or more tasks by applying input information containing sound information from the living body sounds recorded by the microphone to the learning information, and the processor displays the tasks on the display device.

13. An information processing method realized using a processor of an information processing apparatus, comprising:

a sound information acquiring step of the processor acquiring sound information regarding living body sounds, which are sounds emanating from a living body, of a user;

a task acquiring step of the processor acquiring one or more tasks corresponding to the user, using input information containing the sound information acquired in the sound information acquiring step and learning information prepared in advance;

a task output step of the processor outputting information on the tasks acquired in the task acquiring step; and a device identifying information acquiring step of the processor acquiring device identifying information for identifying the type of device used to acquire living body sounds corresponding to the sound information, wherein multiple pieces of learning information are prepared respectively in association with pieces of device identifying information, and the processor acquires a task using the learning information corresponding to the device identifying information acquired by the processor, wherein the information processing apparatus is configured to acquire a suitable task according to properties of a device used for acquiring the living body sounds, wherein the processor generates a spectrogram based on sound data, the sound data is obtained by recording abdominal sounds, and the spectrogram is the sound information and an input to the processor, and wherein the processor uses machine learning.

14. A non-transitory recording medium on which a program is recorded, the program causing a computer comprising a processor, wherein the processor acquires sound information regarding living body sounds, which are sounds emanating from a living body, of a user;

the processor acquires one or more tasks corresponding to the user, using input information containing the sound information acquired by the processor and learning information prepared in advance;

the processor outputs information on the tasks acquired by the processor; and the processor acquires device identifying information for identifying the type of device used to acquire living body sounds corresponding to the sound information, wherein multiple pieces of learning information are prepared respectively in association with pieces of device identifying information, and the processor acquires a task using the learning information corresponding to the device identifying information acquired by the processor, wherein the computer is configured to acquire a suitable task according to properties of a device used for acquiring the living body sounds, wherein the processor generates a spectrogram based on sound data, the sound data is obtained by recording abdominal sounds, and the spectrogram is the sound information and an input to the processor, and wherein the processor uses machine learning.

* * * * *